United States Patent
Högberg et al.

(10) Patent No.: US 8,927,547 B2
(45) Date of Patent: Jan. 6, 2015

(54) PYRIMIDINE DERIVATIVES

(75) Inventors: Marita Högberg, Huddinge (SE);
Tommy Johansson, Huddinge (SE);
Emma Dahlstedt, Huddinge (SE); Olof Smitt, Huddinge (SE)

(73) Assignee: Noviga Research AB, Tullinge (SE)

( * ) Notice: Subject to any disclaimer, the term of this patent is extended or adjusted under 35 U.S.C. 154(b) by 65 days.

(21) Appl. No.: 13/697,954

(22) PCT Filed: May 20, 2011

(86) PCT No.: PCT/EP2011/058271
§ 371 (c)(1),
(2), (4) Date: Nov. 30, 2012

(87) PCT Pub. No.: WO2011/144742
PCT Pub. Date: Nov. 24, 2011

(65) Prior Publication Data
US 2013/0089518 A1    Apr. 11, 2013

(30) Foreign Application Priority Data

May 21, 2010    (EP) .................................... 10163597
Oct. 12, 2010    (EP) .................................... 10187289

(51) Int. Cl.
| C07D 403/14 | (2006.01) |
| C07D 413/14 | (2006.01) |
| A61K 31/506 | (2006.01) |
| A61K 31/5377 | (2006.01) |
| A61K 45/06 | (2006.01) |

(52) U.S. Cl.
CPC ............ C07D 413/14 (2013.01); C07D 403/14 (2013.01); A61K 31/506 (2013.01); A61K 31/5377 (2013.01); A61K 45/06 (2013.01)
USPC ......... 514/235.8; 514/275; 544/122; 544/324

(58) Field of Classification Search
USPC .................... 544/122, 324; 514/235.8, 275
See application file for complete search history.

(56) References Cited

U.S. PATENT DOCUMENTS

| 5,412,091 | A | 5/1995 | Boivin et al. |
| 5,455,348 | A | 10/1995 | Austel et al. |
| 5,491,234 | A | 2/1996 | Coe et al. |
| 5,616,743 | A | 4/1997 | Boivin et al. |
| 6,596,746 | B1 | 7/2003 | Das et al. |
| 6,649,608 | B2 | 11/2003 | Pease et al. |
| 6,881,737 | B2 | 4/2005 | Buchanan et al. |
| 6,897,220 | B2 | 5/2005 | Delorme et al. |
| 6,939,874 | B2 | 9/2005 | Harmange et al. |
| 6,979,694 | B2 | 12/2005 | Das et al. |
| 7,060,827 | B2 | 6/2006 | Singh et al. |
| 7,091,233 | B2 | 8/2006 | Fischer et al. |
| 7,109,335 | B2 | 9/2006 | Kath et al. |
| 7,109,337 | B2 | 9/2006 | Kath et al. |
| 7,112,587 | B2 | 9/2006 | Timmer et al. |
| 7,115,617 | B2 | 10/2006 | Buchanan et al. |
| 7,122,542 | B2 | 10/2006 | Singh et al. |
| 7,125,875 | B2 | 10/2006 | Das et al. |
| 7,132,423 | B2 | 11/2006 | Timmer et al. |
| 7,153,856 | B2 | 12/2006 | Barrish et al. |
| 7,163,943 | B2 | 1/2007 | Timmer et al. |
| 7,169,784 | B2 | 1/2007 | Timmer et al. |
| 7,169,785 | B2 | 1/2007 | Timmer et al. |
| 7,173,032 | B2 | 2/2007 | Timmer et al. |
| 7,189,854 | B2 | 3/2007 | Das et al. |
| 7,235,561 | B2 | 6/2007 | Brumby et al. |
| 7,235,562 | B2 | 6/2007 | Kath et al. |
| 7,238,692 | B2 | 7/2007 | Timmer et al. |
| 7,265,114 | B2 | 9/2007 | Timmer et al. |
| 7,268,134 | B2 | 9/2007 | Timmer et al. |
| 7,291,624 | B2 | 11/2007 | Brumby et al. |

(Continued)

FOREIGN PATENT DOCUMENTS

| AU | 2006201229 B2 | 4/2006 |
| AU | 2006201230 B8 | 4/2006 |

(Continued)

OTHER PUBLICATIONS

Pearce et al., Failure modes in anticancer drug discovery and development, Cancer Drug Design and Discovery Edited by Stephen Neidle, Chapter 18, pp. 424-435 (2008).*
Johnson et al., Relationships between drug activity in NCI preclinical in vitro and in vivo models and early clinical trials, British Journal of Cancer, 84(10):1424-1431,2001.*
Gura et al., Systems for identifying new drugs are often faulty, Science, 278:1041-1042, 1997.*
Simone, Oncology: Introduction, Cecil Textbook of Medicine, 20th Editino, vol. 1, pp. 1004-1010, 1996.*
Aliagas-Martin et al., "A Class of 2,4-Bisanilinopyrimidine Aurora A Inhibitors with Unusually High Selectivity against Aurora B," J. Med. Chem., vol. 52, 2009 (Published on Web Apr. 29, 2009), pp. 3300-3307.
Beattie et al., "Cyclin-Dependent Kinase 4 Inhibitors as a Treatment for Cancer. Part 1: Identification and Optimisation of Substituted 4,6-Bis Anilino Pyrimidines," Bioorganic & Medicinal Chemistry Letters, vol. 13, 2003, pp. 2955-2960

(Continued)

*Primary Examiner* — Deepak Rao
(74) *Attorney, Agent, or Firm* — Birch, Stewart, Kolasch & Birch, LLP

(57) ABSTRACT

The invention provides novel pyrimidine derivatives of formula I, to methods of preparing such compounds, to pharmaceutical compositions containing such compounds, and to methods for using such compounds in treatment of diseases including cancer; wherein $R^1$, $R^2$, $R^3$, $R^4$, $R^5$, L, A, D, E, Z, and Y are as defined in the specification.

23 Claims, No Drawings

(56) References Cited

U.S. PATENT DOCUMENTS

| | | | |
|---|---|---|---|
| 7,329,671 B2 | 2/2008 | Singh et al. |
| 7,329,672 B2 | 2/2008 | Singh et al. |
| 7,332,484 B2 | 2/2008 | Singh et al. |
| 7,332,488 B2 | 2/2008 | Timmer et al. |
| 7,332,489 B2 | 2/2008 | Timmer et al. |
| 7,332,490 B2 | 2/2008 | Timmer et al. |
| 7,335,656 B2 | 2/2008 | Timmer et al. |
| 7,351,712 B2 | 4/2008 | Kath et al. |
| 7,435,814 B2 | 10/2008 | Singh et al. |
| 7,449,465 B2 | 11/2008 | Freyne et al. |
| 7,452,879 B2 | 11/2008 | Singh et al. |
| 7,485,724 B2 | 2/2009 | Singh et al. |
| 7,491,732 B2 | 2/2009 | Li et al. |
| 7,498,435 B2 | 3/2009 | Singh et al. |
| 7,501,424 B2 | 3/2009 | Kim et al. |
| 7,504,410 B2 | 3/2009 | Bryant et al. |
| 7,511,137 B2 | 3/2009 | Li |
| 7,514,445 B2 | 4/2009 | Freyne et al. |
| 7,517,886 B2 | 4/2009 | Singh et al. |
| 7,521,453 B2 | 4/2009 | Barlaam et al. |
| 7,521,457 B2 | 4/2009 | Stadtmueller et al. |
| 7,528,143 B2 | 5/2009 | Noronha et al. |
| 7,550,460 B2 | 6/2009 | Singh et al. |
| 7,557,210 B2 | 7/2009 | Singh et al. |
| 7,560,458 B2 | 7/2009 | Freyne et al. |
| 7,560,464 B2 | 7/2009 | Wang et al. |
| 7,560,466 B2 | 7/2009 | Singh et al. |
| 7,582,648 B2 | 9/2009 | Singh et al. |
| 7,589,200 B2 | 9/2009 | Singh et al. |
| 7,595,343 B2 | 9/2009 | Delorme et al. |
| 7,598,260 B2 | 10/2009 | Brumby et al. |
| 7,642,351 B2 | 1/2010 | Singh et al. |
| 7,655,797 B2 | 2/2010 | Singh et al. |
| 7,674,796 B2 | 3/2010 | Kath et al. |
| 7,683,061 B2 | 3/2010 | Penney et al. |
| 7,718,653 B2 | 5/2010 | Barlaam et al. |
| 7,741,336 B2 | 6/2010 | Kath et al. |
| 7,754,714 B2 | 7/2010 | Li et al. |
| 7,767,806 B2 | 8/2010 | Hirakura et al. |
| 7,803,939 B2 | 9/2010 | Singh et al. |
| 7,812,029 B1 | 10/2010 | Singh et al. |
| 7,820,648 B2 | 10/2010 | Bhattacharya et al. |
| 7,820,819 B2 | 10/2010 | Singh et al. |
| 7,825,116 B2 | 11/2010 | Singh et al. |
| 7,825,246 B2 | 11/2010 | Noronha et al. |
| 7,834,024 B2 | 11/2010 | Li et al. |
| 7,838,520 B2 | 11/2010 | Delorme et al. |
| 7,858,633 B2 | 12/2010 | Li et al. |
| 7,858,782 B2 | 12/2010 | Tao et al. |
| 7,863,286 B2 | 1/2011 | Argade et al. |
| 7,868,013 B2 | 1/2011 | Li et al. |
| 7,868,204 B2 | 1/2011 | Delorme et al. |
| 7,884,111 B2 | 2/2011 | Argade et al. |
| 7,893,074 B2 | 2/2011 | Garcia-Echeverria et al. |
| 7,906,644 B2 | 3/2011 | Singh et al. |
| 7,915,273 B2 | 3/2011 | Argade et al. |
| 7,928,109 B2 | 4/2011 | Luzzio et al. |
| 7,943,628 B2 | 5/2011 | Bell et al. |
| 7,947,698 B2 | 5/2011 | Atuegbu et al. |
| 7,956,185 B2 | 6/2011 | Diebold et al. |
| 7,962,290 B1 | 6/2011 | Qu |
| 7,964,592 B2 | 6/2011 | Garcia-Echeverria et al. |
| 7,968,556 B2 | 6/2011 | Mortensen et al. |
| 7,971,443 B2 | 7/2011 | Nishita et al. |
| 7,982,036 B2 | 7/2011 | Singh et al. |
| 7,989,465 B2 | 8/2011 | Singh et al. |
| 8,030,483 B2 | 10/2011 | Argade et al. |
| 8,039,479 B2 | 10/2011 | Michellys et al. |
| 8,044,054 B2 | 10/2011 | Argade et al. |
| 8,101,627 B2 | 1/2012 | Argade et al. |
| 8,114,882 B2 | 2/2012 | Heinrich et al. |
| 8,133,900 B2 | 3/2012 | Hood et al. |
| 8,138,199 B2 | 3/2012 | Noronha et al. |
| 8,143,391 B2 | 3/2012 | Yasugi et al. |
| 8,148,388 B2 | 4/2012 | Freyne et al. |
| 8,148,525 B2 | 4/2012 | Singh et al. |
| 8,158,621 B2 | 4/2012 | Singh et al. |
| 8,178,671 B2 | 5/2012 | Singh et al. |
| 8,188,276 B2 | 5/2012 | Singh et al. |
| 8,211,929 B2 | 7/2012 | Chen et al. |
| 8,222,256 B2 | 7/2012 | Zhang |
| 8,227,455 B2 | 7/2012 | Masuda et al. |
| 8,246,984 B2 | 8/2012 | Parmar |
| 8,247,411 B2 | 8/2012 | Luzzio et al. |
| 8,263,590 B2 | 9/2012 | Garcia-Echeverria et al. |
| 8,268,816 B2 | 9/2012 | Gupta et al. |
| 8,299,087 B2 | 10/2012 | Li et al. |
| 8,304,422 B2 | 11/2012 | Atuegbu et al. |
| 8,304,557 B2 | 11/2012 | Oguro et al. |
| 8,329,901 B2 | 12/2012 | Singh et al. |
| 8,334,296 B2 | 12/2012 | Singh et al. |
| 8,338,439 B2 | 12/2012 | Singh et al. |
| 8,344,135 B2 | 1/2013 | Hirose et al. |
| 8,349,859 B2 | 1/2013 | Su et al. |
| 8,354,407 B2 | 1/2013 | Djung et al. |
| 2003/0004161 A1 | 1/2003 | Bebbington et al. |
| 2003/0004164 A1 | 1/2003 | Bebbington et al. |
| 2003/0022885 A1 | 1/2003 | Bebbington et al. |
| 2003/0036543 A1 | 2/2003 | Bebbington et al. |
| 2003/0055068 A1 | 3/2003 | Bebbington et al. |
| 2003/0064981 A1 | 4/2003 | Knegtel et al. |
| 2003/0069238 A1 | 4/2003 | Barrish et al. |
| 2003/0073687 A1 | 4/2003 | Bebbington et al. |
| 2003/0078166 A1 | 4/2003 | Davies et al. |
| 2003/0078275 A1 | 4/2003 | Bebbington et al. |
| 2003/0105090 A1 | 6/2003 | Bebbington et al. |
| 2003/0125346 A1 | 7/2003 | Buchanan et al. |
| 2003/0139416 A1 | 7/2003 | Buchanan et al. |
| 2003/0149266 A1 | 8/2003 | Pease et al. |
| 2003/0171359 A1 | 9/2003 | Dahmann et al. |
| 2003/0225073 A1 | 12/2003 | Bebbington et al. |
| 2004/0002496 A1 | 1/2004 | Bebbington et al. |
| 2004/0002507 A1 | 1/2004 | Nagarathnam et al. |
| 2004/0024208 A1 | 2/2004 | Das et al. |
| 2004/0029902 A1 | 2/2004 | Singh et al. |
| 2004/0054186 A1 | 3/2004 | Das et al. |
| 2004/0063705 A1 | 4/2004 | Harmange et al. |
| 2004/0072760 A1 | 4/2004 | Carboni et al. |
| 2004/0073026 A1 | 4/2004 | Das et al. |
| 2004/0077648 A1 | 4/2004 | Timmer et al. |
| 2004/0077875 A1 | 4/2004 | Das et al. |
| 2004/0097501 A1 | 5/2004 | Bebbington et al. |
| 2004/0102630 A1 | 5/2004 | Brumby et al. |
| 2004/0106599 A1 | 6/2004 | Delorme et al. |
| 2004/0106605 A1 | 6/2004 | Carboni et al. |
| 2004/0142953 A1 | 7/2004 | Delorme et al. |
| 2004/0186118 A1 | 9/2004 | Bryant et al. |
| 2004/0209930 A1 | 10/2004 | Carboni et al. |
| 2004/0214814 A1 | 10/2004 | Bebbington et al. |
| 2004/0220177 A1 | 11/2004 | Kath et al. |
| 2004/0224950 A1 | 11/2004 | Timmer et al. |
| 2004/0224966 A1 | 11/2004 | Brumby et al. |
| 2005/0004110 A1 | 1/2005 | Bebbington et al. |
| 2005/0004125 A1 | 1/2005 | Freyne et al. |
| 2005/0009853 A1 | 1/2005 | Kath et al. |
| 2005/0038023 A1 | 2/2005 | Bebbington et al. |
| 2005/0038243 A1 | 2/2005 | Singh et al. |
| 2005/0054638 A1 | 3/2005 | Barlaam et al. |
| 2005/0090493 A1 | 4/2005 | Breault et al. |
| 2005/0092224 A1 | 5/2005 | Kochi et al. |
| 2005/0107399 A1 | 5/2005 | Boman et al. |
| 2005/0113341 A1 | 5/2005 | Timmer et al. |
| 2005/0113398 A1 | 5/2005 | Argade et al. |
| 2005/0124619 A1 | 6/2005 | Timmer et al. |
| 2005/0137196 A1 | 6/2005 | Timmer et al. |
| 2005/0192301 A1 | 9/2005 | Li |
| 2005/0209230 A1 | 9/2005 | Singh et al. |
| 2005/0234049 A1 | 10/2005 | Singh et al. |
| 2005/0234083 A1 | 10/2005 | Chamberlain et al. |
| 2005/0245518 A1 | 11/2005 | Delorme et al. |
| 2005/0256111 A1 | 11/2005 | Kath et al. |
| 2005/0256145 A1 | 11/2005 | Kath et al. |
| 2005/0261305 A1 | 11/2005 | Das et al. |
| 2005/0267089 A1 | 12/2005 | Wang et al. |

(56) References Cited

U.S. PATENT DOCUMENTS

| | | |
|---|---|---|
| 2005/0288282 A1 | 12/2005 | Delorme et al. |
| 2005/0288303 A1 | 12/2005 | Barrish et al. |
| 2006/0025410 A1 | 2/2006 | Singh et al. |
| 2006/0030598 A1 | 2/2006 | Barrish et al. |
| 2006/0035891 A1 | 2/2006 | Li et al. |
| 2006/0035916 A1 | 2/2006 | Singh et al. |
| 2006/0051406 A1 | 3/2006 | Parmar |
| 2006/0058292 A1 | 3/2006 | Singh et al. |
| 2006/0058298 A1 | 3/2006 | Delorme et al. |
| 2006/0058525 A1 | 3/2006 | Singh et al. |
| 2006/0063789 A1 | 3/2006 | Freyne et al. |
| 2006/0079563 A1 | 4/2006 | Das et al. |
| 2006/0135543 A1 | 6/2006 | Singh et al. |
| 2006/0148800 A1 | 7/2006 | Stadtmueller et al. |
| 2006/0167249 A1 | 7/2006 | Argade et al. |
| 2006/0172984 A1 | 8/2006 | Timmer et al. |
| 2006/0183747 A1 | 8/2006 | Freyne et al. |
| 2006/0205721 A1 | 9/2006 | Freyne et al. |
| 2006/0205945 A1 | 9/2006 | Kath et al. |
| 2006/0247241 A1 | 11/2006 | Garcia-Echeverria et al. |
| 2006/0258641 A1 | 11/2006 | Timmer et al. |
| 2006/0276459 A1 | 12/2006 | Masuda et al. |
| 2006/0281774 A1 | 12/2006 | Kath et al. |
| 2006/0293311 A1 | 12/2006 | Li et al. |
| 2007/0004729 A1 | 1/2007 | Timmer et al. |
| 2007/0010668 A1 | 1/2007 | Davis-Ward et al. |
| 2007/0021443 A1 | 1/2007 | Ohlmeyer et al. |
| 2007/0031161 A1 | 2/2007 | Iandoli et al. |
| 2007/0031503 A1 | 2/2007 | Hirakura et al. |
| 2007/0043051 A1 | 2/2007 | Timmer et al. |
| 2007/0060603 A1 | 3/2007 | Singh et al. |
| 2007/0099874 A1 | 5/2007 | Timmer et al. |
| 2007/0105839 A1 | 5/2007 | Imbach et al. |
| 2007/0117795 A1 | 5/2007 | Timmer et al. |
| 2007/0122444 A1 | 5/2007 | Timmer et al. |
| 2007/0134334 A1 | 6/2007 | Hahn et al. |
| 2007/0141684 A1 | 6/2007 | Evans et al. |
| 2007/0149528 A1 | 6/2007 | Penney et al. |
| 2007/0167439 A1 | 7/2007 | Singh et al. |
| 2007/0179140 A1 | 8/2007 | Argade et al. |
| 2007/0185075 A1 | 8/2007 | Bell et al. |
| 2007/0191405 A1 | 8/2007 | Noronha et al. |
| 2007/0203161 A1 | 8/2007 | Argade et al. |
| 2007/0203162 A1 | 8/2007 | Li et al. |
| 2007/0225321 A1 | 9/2007 | Singh et al. |
| 2007/0225495 A1 | 9/2007 | Singh et al. |
| 2007/0259904 A1 | 11/2007 | Noronha et al. |
| 2007/0270427 A1 | 11/2007 | Boloor et al. |
| 2007/0270444 A1 | 11/2007 | Bebbington et al. |
| 2007/0293494 A1 | 12/2007 | Djung et al. |
| 2007/0293520 A1 | 12/2007 | Singh et al. |
| 2007/0293521 A1 | 12/2007 | Singh et al. |
| 2007/0293522 A1 | 12/2007 | Singh et al. |
| 2007/0293523 A1 | 12/2007 | Singh et al. |
| 2007/0293524 A1 | 12/2007 | Singh et al. |
| 2007/0299060 A1 | 12/2007 | Li et al. |
| 2007/0299095 A1 | 12/2007 | Singh et al. |
| 2008/0004302 A1 | 1/2008 | Theoclitou et al. |
| 2008/0009484 A1 | 1/2008 | Argade et al. |
| 2008/0009494 A1 | 1/2008 | Li et al. |
| 2008/0015192 A1 | 1/2008 | Diebold et al. |
| 2008/0021020 A1 | 1/2008 | Argade et al. |
| 2008/0027045 A1 | 1/2008 | Argade et al. |
| 2008/0039447 A1 | 2/2008 | Brumby et al. |
| 2008/0039622 A1 | 2/2008 | Singh et al. |
| 2008/0051404 A1 | 2/2008 | Claiborne et al. |
| 2008/0051412 A1 | 2/2008 | Argade et al. |
| 2008/0082567 A1 | 4/2008 | Bezanson |
| 2008/0096899 A1 | 4/2008 | Kim et al. |
| 2008/0096901 A1 | 4/2008 | Arnost et al. |
| 2008/0119496 A1 | 5/2008 | Ohlmeyer et al. |
| 2008/0132504 A1 | 6/2008 | Garcia-Echeverria et al. |
| 2008/0167330 A1 | 7/2008 | Luecking et al. |
| 2008/0176853 A1 | 7/2008 | Tao et al. |
| 2008/0176866 A1 | 7/2008 | Jautelat et al. |
| 2008/0176881 A1 | 7/2008 | Michellys et al. |
| 2008/0182840 A1 | 7/2008 | Kath et al. |
| 2008/0194605 A1 | 8/2008 | Heinrich et al. |
| 2008/0214558 A1 | 9/2008 | Vankayalapati et al. |
| 2008/0221089 A1 | 9/2008 | Argade et al. |
| 2008/0234303 A1 | 9/2008 | Bhattacharya et al. |
| 2008/0249079 A1 | 10/2008 | Chen et al. |
| 2008/0255172 A1 | 10/2008 | Su et al. |
| 2008/0260754 A1 | 10/2008 | Li et al. |
| 2008/0269170 A1 | 10/2008 | Bosch et al. |
| 2008/0279867 A1 | 11/2008 | Atuegbu et al. |
| 2008/0287468 A1 | 11/2008 | Ohlmeyer et al. |
| 2008/0298830 A1 | 12/2008 | Kamisuwa et al. |
| 2008/0312438 A1 | 12/2008 | Singh et al. |
| 2009/0012045 A1 | 1/2009 | Hitoshi et al. |
| 2009/0023719 A1 | 1/2009 | Barlaam et al. |
| 2009/0023738 A1 | 1/2009 | Braeuer et al. |
| 2009/0036471 A1 | 2/2009 | Edgard et al. |
| 2009/0041786 A1 | 2/2009 | Li et al. |
| 2009/0042890 A1 | 2/2009 | Mortensen et al. |
| 2009/0054395 A1 | 2/2009 | Luzzio et al. |
| 2009/0118310 A1 | 5/2009 | Nur-E-Kamal et al. |
| 2009/0124645 A1 | 5/2009 | Sorensen et al. |
| 2009/0131463 A1 | 5/2009 | Barlaam et al. |
| 2009/0137588 A1 | 5/2009 | Singh et al. |
| 2009/0137589 A1 | 5/2009 | Argade et al. |
| 2009/0148534 A1 | 6/2009 | Yasugi et al. |
| 2009/0149438 A1 | 6/2009 | Stadtmueller et al. |
| 2009/0156622 A1 | 6/2009 | Singh et al. |
| 2009/0156662 A1 | 6/2009 | Nozawa et al. |
| 2009/0163465 A1 | 6/2009 | Stadtmueller et al. |
| 2009/0163488 A1 | 6/2009 | Oguro et al. |
| 2009/0171085 A1 | 7/2009 | Singh et al. |
| 2009/0171086 A1 | 7/2009 | Singh et al. |
| 2009/0176981 A1 | 7/2009 | Argade et al. |
| 2009/0193826 A1 | 8/2009 | Yasugi et al. |
| 2009/0227586 A1 | 9/2009 | Djung et al. |
| 2009/0232838 A1 | 9/2009 | Dong et al. |
| 2009/0275582 A1 | 11/2009 | Noronha et al. |
| 2009/0281073 A1 | 11/2009 | Bhattacharya et al. |
| 2009/0286789 A1 | 11/2009 | Hood et al. |
| 2009/0291129 A1 | 11/2009 | Parmar |
| 2009/0298830 A1 | 12/2009 | Mann et al. |
| 2009/0299093 A1 | 12/2009 | Evans et al. |
| 2009/0306067 A1 | 12/2009 | Engelhardt et al. |
| 2009/0318687 A1 | 12/2009 | Singh et al. |
| 2010/0016296 A1 | 1/2010 | Singh et al. |
| 2010/0029610 A1 | 2/2010 | Singh et al. |
| 2010/0056503 A1 | 3/2010 | Gupta et al. |
| 2010/0093668 A1 | 4/2010 | Babin et al. |
| 2010/0125069 A1 | 5/2010 | Singh et al. |
| 2010/0144732 A1 | 6/2010 | Krueger et al. |
| 2010/0152218 A1 | 6/2010 | Argade et al. |
| 2010/0160310 A1 | 6/2010 | Freyne et al. |
| 2010/0197918 A1 | 8/2010 | Singh et al. |
| 2010/0249092 A1 | 9/2010 | Singh et al. |
| 2010/0279410 A1 | 11/2010 | Demko et al. |
| 2010/0298295 A1 | 11/2010 | Marsilje et al. |
| 2010/0298314 A1 | 11/2010 | Reddy et al. |
| 2010/0305099 A1 | 12/2010 | Sapountzis et al. |
| 2011/0027856 A1 | 2/2011 | Li et al. |
| 2011/0046108 A1 | 2/2011 | Kettle et al. |
| 2011/0046121 A1 | 2/2011 | Liang et al. |
| 2011/0046126 A1 | 2/2011 | Masuda et al. |
| 2011/0082146 A1 | 4/2011 | Atuegbu et al. |
| 2011/0086842 A1 | 4/2011 | Stadtmueller et al. |
| 2011/0098280 A1 | 4/2011 | Garcia-Echeverria et al. |
| 2011/0098288 A1 | 4/2011 | Major et al. |
| 2011/0112063 A1 | 5/2011 | Marsilje et al. |
| 2011/0112096 A1 | 5/2011 | Marsilje et al. |
| 2011/0144330 A1 | 6/2011 | Singh et al. |
| 2011/0150763 A1 | 6/2011 | Tao et al. |
| 2011/0152518 A1 | 6/2011 | Li et al. |
| 2011/0166120 A1 | 7/2011 | Luzzio et al. |
| 2011/0166139 A1 | 7/2011 | Barlaam et al. |
| 2011/0190259 A1 | 8/2011 | Michellys et al. |
| 2011/0190271 A1 | 8/2011 | Argade et al. |
| 2011/0201606 A1 | 8/2011 | Garcia-Echeverria et al. |
| 2011/0203768 A1 | 8/2011 | Nishita et al. |

(56) References Cited

U.S. PATENT DOCUMENTS

| | | |
|---|---|---|
| 2011/0212077 A1 | 9/2011 | Noronha et al. |
| 2011/0224217 A1 | 9/2011 | Mortensen et al. |
| 2011/0224432 A1 | 9/2011 | Singh et al. |
| 2011/0230494 A1 | 9/2011 | Singh et al. |
| 2011/0257155 A1 | 10/2011 | Michellys et al. |
| 2011/0312908 A1 | 12/2011 | Gray et al. |
| 2012/0045454 A1 | 2/2012 | Singh et al. |
| 2012/0065395 A1 | 3/2012 | Freyne et al. |
| 2012/0095011 A1 | 4/2012 | Barlaam et al. |
| 2012/0183567 A1 | 7/2012 | Yasugi et al. |
| 2012/0245127 A1 | 9/2012 | Masuda et al. |
| 2012/0249119 A1 | 10/2012 | Wada et al. |
| 2012/0253039 A1 | 10/2012 | Singh et al. |
| 2013/0005748 A1 | 1/2013 | Michellys et al. |
| 2013/0005964 A1 | 1/2013 | Luzzio et al. |

FOREIGN PATENT DOCUMENTS

| | | |
|---|---|---|
| AU | 2006201262 B2 | 4/2006 |
| AU | 2006201263 B2 | 4/2006 |
| AU | 2006201264 A1 | 4/2006 |
| AU | 2006201265 B2 | 4/2006 |
| AU | 2006252047 B2 | 1/2007 |
| CN | 101289444 A | 10/2008 |
| CN | 101684098 A | 3/2010 |
| EP | 1522540 A1 | 4/2005 |
| FR | 2919869 A1 | 2/2009 |
| WO | WO 03/026666 A1 | 4/2003 |
| WO | WO 03/030909 A1 | 4/2003 |
| WO | WO 03/040141 A1 | 5/2003 |
| WO | WO 03/063794 A2 | 8/2003 |
| WO | WO 2004/041164 A2 | 5/2004 |
| WO | WO 2004/046118 A2 | 6/2004 |
| WO | WO 2004/056786 A2 | 7/2004 |
| WO | WO 2004/056807 A1 | 7/2004 |
| WO | WO 2005/013996 A2 | 2/2005 |
| WO | WO 2006/124874 A2 | 11/2006 |
| WO | WO 2006/133426 A2 | 12/2006 |
| WO | WO 2007/085833 A2 | 8/2007 |
| WO | WO 2007/121662 A1 | 11/2007 |
| WO | WO 2008/124085 A2 | 10/2008 |
| WO | WO 2008/128231 A1 | 10/2008 |
| WO | WO 2009/017838 A2 | 2/2009 |
| WO | WO 2009/063240 A1 | 5/2009 |
| WO | WO 2009/070645 A1 | 6/2009 |
| WO | WO 2010/119050 | * 10/2010 |
| WO | WO 2011/120025 A1 | 9/2011 |
| WO | WO 2011/120026 A1 | 9/2011 |

OTHER PUBLICATIONS

Breault et al., "Cyclin-Dependent Kinase 4 Inhibitors as a Treatment for Cancer. Part 2: Identification and Optimisation of Substituted 2,4-Bis Anilino Pyrimidines," Bioorganic & Medicinal Chemistry Letters,, vol. 13, 2003, pp. 2961-2966.

Brugel et al., "Corrigendum to "Development of N-2,4-pyrimidine-N-phenyl-N'-phenyl ureas as inhibitors of tumor necrosis factor alpha (TNF-α) synthesis. Part 1,"" Bioorganic & Medicinal Chemistry Letters, vol. 16, No. 17, 2006 (Available online Jun. 27, 2006), p. 4700.

Brugel et al., "Development of N-2,4-pyrimidine-N-phenyl-N'-phenyl ureas as inhibitors of tumor necrosis factor alpha (TNF-α) synthesis. Part 1," Bioorganic & Medicinal Chemistry Letters, vol. 16, No. 13, 2006 (Available online May 2, 2006), pp. 3510-3513.

Chemical Abstracts Service, RN 1028311-39-8, CA Index Name: "1H-Benzimidazole-4,7-diamine, N4-[4-[[(4-iodophenyl)methyl]amino]-2-pyrimidinyl]-1-(1-methylethyl)-," entered STN Jun. 15, 2008.

Dev et al., "Antitumour efficacy of VEGFR2 tyrosine kinase inhibitor correlates with expression of VEGF and its receptor VEGFR2 in tumour models," British Journal of Cancer, vol. 91, 2004 (Published online Aug. 24, 2004), pp. 1391-1398.

Elderfield et al., "Synthesis of Potential Anticancer Agent. IV. Synthesis of Certain Substituted Amino- and Aziridinopyrimidines," Journal of Organic Chemistry, vol. 25, Sep. 1960, pp. 1583-1590.

Feldman et al., "Novel Small Molecule Inhibitors of 3-Phosphoinositide-dependent Kinase-1," The Journal of Biological Chemistry, vol. 280, No. 20, May 20, 2005, pp. 19867-19874.

Ghoneim et al., "Synthesis of Some Mannich Bases of 2-,4-Amino- and 2,4-Diamino-6-Methylpyrimidines as Potential Biodynamic Agents," Egypt. J. Chem., vol. 30, No. 4, 1987, pp. 295-304.

Gossage et al., "Targeting Multiple Kinase Pathways: A Change in Paradigm," Clin. Cancer Res., vol. 16, No. 7, 2010 (Published online first Mar. 9, 2010), pp. 1973-1978.

Gunther et al., "Alternative Inhibition of Androgen Receptor Signaling: Peptidomimetic Pyrimidines as Direct Androgen Receptor/Coactivator Disruptors," ASC Chemical Biology, vol. 4, No. 6, 2009 (Published online May 14, 2009), pp. 435-440.

Harris et al., "Discovery of 5-[[4-[(2,3-Dimethyl-2H-indazol-6-yl)methylamino]-2-pyrimidinyl]amino]-2-methyl-benzenesulfonamide (Pazopanib), a Novel and Potent Vascular Endothelial Growth Factor Receptor Inhibitor," J. Med. Chem., vol. 51, 2008 (Published on Web Jul. 12, 2008), pp. 4632-4640.

International Preliminary Report on Patentability and Written Opinion of the International Searching Authority for International Application No. PCT/EP2011/058271, issued Nov. 27, 2012.

Krasnykh et al., "Radiation Protection Action of Some New Purine and Pyramidon Derivatives," Farmakologiya i Toksikologiya (Moscow), vol. 24, 1961, pp. 572-577, including an English-language abstract.

Lafleur et al., "Structure-Based Optimization of Potent and Selective Inhibitors of the Tyrosine Kinase Erythropoietin Producing Human Hepatocellular Carcinoma Receptor B4 (EphB4)," J. Med. Chem., vol. 52, 2009 (Published on Web Sep. 29, 2009), pp. 6433-6446.

Lombardo et al., "Discovery of N-(2-Chloro-6-methyl-phenyl)-2-(6-(4-(2-hydroxyethyl)-piperazin-1-yl)-2-methylpyrimidin-4-ylamino)thiazole-5-carboxamide (BMS-354825), a Dual Src/Abl Kinase Inhibitor . . . ," J. Med. Chem., vol. 47, 2004 (Published on Web Dec. 7, 2004), pp. 6658-6661.

Otmar et al., "Synthesis and antiproliferative activity of 2,6-diamino-9-benzy1-9-deazapurine and related compounds," Bioorganic & Medicinal Chemistry, vol. 12, 2004 (Available online May 10, 2004), pp. 3187-3195.

Parent et al., "Blocking Estrogen Signaling After the Hormone: Pyrimidine-Core Inhibitors of Estrogen Receptor—Coactivator Binding," J. Med. Chem., vol. 51, 2008 (Published on Web Sep. 12, 2008), pp. 6512-6530.

Ugarkar et al., "Adenosine Kinase Inhibitors. 3. Synthesis, SAR, and Antiinflammatory Activity of a Series of L-Lyxofuranosyl Nucleosides," J. Med. Chem., vol. 46, 2003 (Publlished on Web Sep. 23, 2003), pp. 4750-4760.

Mashkovsky, M.D., "Medicaments", S.B. Divov, 2001, vol. 1, p. 11 (w/ English translation).

* cited by examiner

PYRIMIDINE DERIVATIVES

FIELD OF INVENTION

This invention relates to novel pyrimidine derivatives of formula I, to methods of preparing such compounds, to pharmaceutical compositions containing such compounds, and to methods for using such compounds in treatment of diseases including cancer.

BACKGROUND OF INVENTION

Cancer is a major and often fatal disease. Accordingly, the development of new therapies for cancer is an ongoing process of outmost importance. The majority of cancers are present as solid tumours, such as lung cancer, breast cancer and prostate cancer, while others represent haematological and lymphoid malignancies, such as leukaemias and lymphomas.

During the recent decade much interest has been devoted to drugs directed to specific target molecules. Molecules regulating cell proliferation and death, such as Tyrosine Kinase Receptors (RTKs) for growth factors, are among targets for this type of therapeutic approach. Two classes of compounds targeting RTKs are currently used in clinical practice: monoclonal antibodies and tyrosine kinase inhibitors. The first approved targeted therapies were trastuzumab, a monoclonal antibody against HER2, for treatment of metastatic breast cancer, and imatinib, a small tyrosine kinase inhibitor targeting BCR-Abl, in Chronic Myeloid Leukemia. Despite good treatment results many of the treated patients have developed drug resistance, often due to the activation of alternative RTKs pathways. Currently there is a general idea that molecules interfering simultaneously with multiple RTKs might be more effective than single target agents. There are a few recently approved drugs, such as sorafenib and sunitinib, that apparently target multiple pathways and could serve as representatives of this new generation of anti-cancer drugs (e.g. Gossage and Eisen, Targeting multiple kinase pathways: a change in paradigm. Clin Cancer Res (2010) vol. 16(7) pp. 1973-8).

Another example of an important target for cancer chemotherapy is tubulin. The targeting drugs in this therapy interrupt microtubule spindle-mediated chromosome segregation, arrest the dividing tumor cells in mitosis and subsequently induce apoptosis. Existing drugs are targeting microtubules via two main mechanisms, e.g. molecules of the taxane class (that stabilize the tubulins) and several vinca alkaloids (destabilizers). The potency, efficacy, and widespread clinical use of these agents of natural origin in a variety of cancers, e.g. breast, ovarian, prostate, lung, leukaemias, and lymphomas, stand testament to the importance of tubulin and its role in cancer growth. Derivatives and analogs of these plant compounds are constantly being isolated or synthesized to find more efficacious anticancer agents. For examples of novel tubulin polymerization inhibitors, see e.g. WO 2009/070645 and US 2010/0279410.

In the clinic cancer chemotherapy is used in attempts to cure or palliate the disease. In most cases this therapy is delivered in the form of combination chemotherapy, i.e. when two or more drugs having different modes of action are used together in order to optimise the effect on the cancer cells and to minimise side effects. The results obtained with chemotherapy vary according to tumour type. Some tumours are very sensitive and the treatment has a high probability of leading to beneficial treatment results including cure of the disease. Examples of this type of tumours are acute leukaemias, malignant lymphomas, testicular cancer, chorion carcinomas, and Wilms tumour. Other types of cancer chemotherapy can result in effective palliation and prolonged survival. Examples of such tumours are breast cancer, colorectal cancer, ovarian cancer, small-cell lung cancer, bladder cancer, multiple myeloma, and chronic leukaemias of both the lymphatic and myeloid type. Primary drug resistant tumours which respond poorly to classical chemotherapy include malignant glioma, melanoma, prostate cancer, sarcomas, and gastrointestinal tumours other than colorectal cancers (see e.g. DeVita, Hellman, and Rosenberg: Cancer: Principles & Practice of Oncology, Eighth Edition 978-0-7817-7207-5).

Certain pyrimidine compounds and their potential use in the treatment of cancer are disclosed in for example WO2003/030909, WO2003/063794, WO2004/056807, WO2004/056786, US2004/220177, WO2005/013996, WO2006/133426, WO2007/085833, WO2008/128231 and WO2009/063240.

What is needed in the art are targeted drugs that work in a specific manner, being selective in eliminating subpopulations of cells involved in tumour survival and progression. The present invention provides novel pyrimidine compounds having a surprisingly efficient and selective antiproliferative activity. Hence, these novel compounds are useful in the treatment of proliferative diseases, such as cancer.

DESCRIPTION OF THE INVENTION

The present invention provides compounds of formula I or a pharmaceutically acceptable ester, amide, solvate or salt thereof,

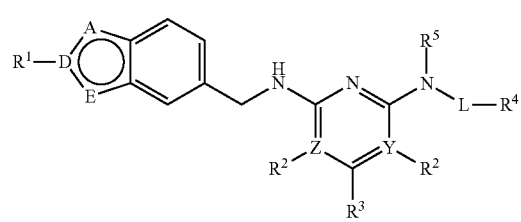

wherein
Z represents carbon or nitrogen;
Y represents carbon or nitrogen; wherein one of Z and Y represents nitrogen;
A, D and E is selected from carbon and nitrogen, wherein A represents nitrogen and
D and E represents carbon; or A and D represent nitrogen and E represents carbon; or
A and E represent nitrogen and D represents carbon; or E represents nitrogen and A and D represent carbon;
L represents a bond or $(C_1\text{-}C_2)$alkyl;
$R^1$ represents hydrogen or methyl, when D represents carbon;
$R^2$ represents hydrogen or amino, when Y or Z represents carbon;
$R^3$ represents hydrogen, $(C_1\text{-}C_3)$alkyl, amino, trifluoromethyl or $(C_0\text{-}C_1)$alkylaryl;
$R^4$ represents heteroaryl, optionally substituted with one or more substituents; and
$R^5$ represents hydrogen or methyl.

In a first aspect of the invention, there is provided a compound of formula I or a pharmaceutically acceptable ester, amide, solvate or salt thereof,

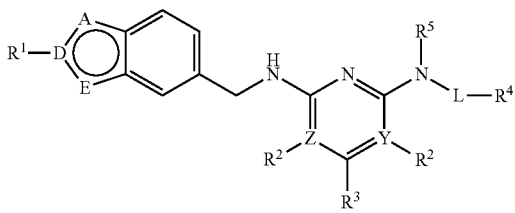

wherein

Z represents carbon or nitrogen;

Y represents carbon or nitrogen; wherein one of Z and Y represents nitrogen;

A, D and E is selected from carbon and nitrogen, wherein A represents nitrogen and D and E represents carbon; or A and D represent nitrogen and E represents carbon; or A and E represent nitrogen and D represents carbon; or E represents nitrogen and A and D represent carbon;

L represents a bond or $(C_1-C_2)$alkyl;

$R^1$ represents hydrogen or methyl, when D represents carbon;

$R^2$ represents hydrogen or amino, when Y or Z represents carbon;

$R^3$ represents hydrogen, $(C_1-C_3)$alkyl, amino, trifluoromethyl or $(C_0-C_1)$alkylaryl;

$R^4$ represents heteroaryl, optionally substituted with one or more substituents; and $R^5$ represents hydrogen or methyl;

provided that the compound $N^2,N^4$-bis(1H-indol-5-ylmethyl)pyrimidine-2,4-diamine is excluded.

In another aspect of the invention, there is provided a compound of formula I, wherein Z, D and E represent carbon; and Y and A represent nitrogen. This is illustrated by formula Ia, wherein $R^1$, $R^2$, $R^3$, $R^4$, $R^5$ and L are as defined under formula I above:

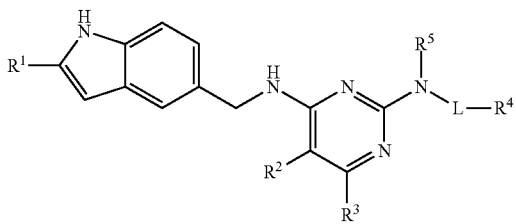

In another aspect of the invention, there is provided a compound of formula I, wherein Z and E represent carbon; and Y, D and A represent nitrogen. This is illustrated by formula Ib, wherein $R^2$, $R^3$, $R^4$, $R^5$ and L are as defined under formula I above:

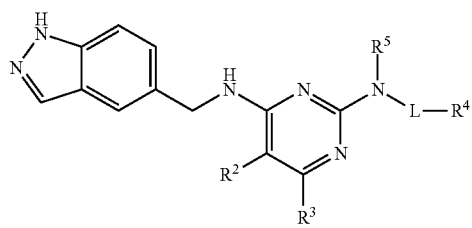

In another aspect of the invention, there is provided a compound of formula I, wherein Z and D represent carbon; and Y, E and A represent nitrogen. This is illustrated by formula Ic, wherein $R^1$, $R^2$, $R^3$, $R^4$, $R^5$ and L are as defined under formula I above:

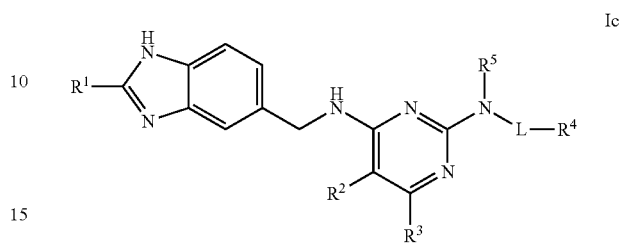

In another aspect of the invention, there is provided a compound of formula I, wherein Z, A and D represent carbon; and Y and E represent nitrogen. This is illustrated by formula Id, wherein $R^1$, $R^2$, $R^3$, $R^4$, $R^5$ and L are as defined under formula I above:

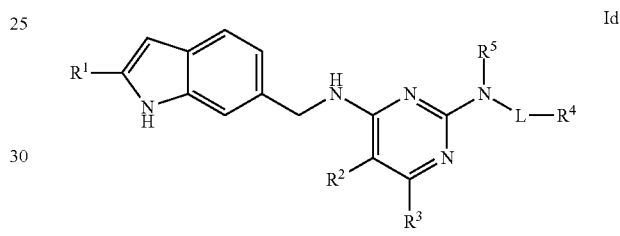

In another aspect of the invention, there is provided a compound of formula I, wherein Y, D and E represent carbon; and Z and A represent nitrogen. This is illustrated by formula Ie, wherein $R^1$, $R^2$, $R^3$, $R^4$, $R^5$ and L are as defined under formula I above:

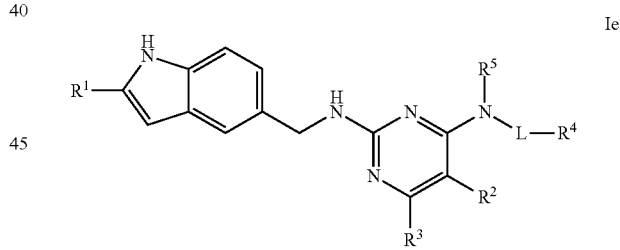

In another aspect of the invention, there is provided a compound of formula I, wherein Y and E represent carbon; and Z, D and A represent nitrogen. This is illustrated by formula If, wherein $R^2$, $R^3$, $R^4$, $R^5$ and L are as defined under formula I above:

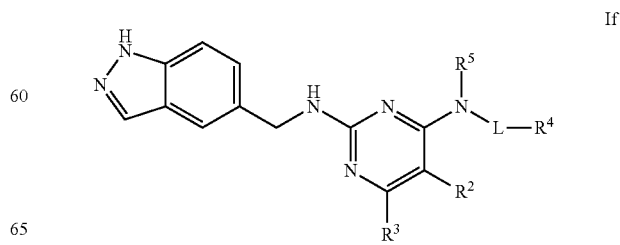

In another aspect of the invention, there is provided a compound of formula I, wherein Y and D represent carbon; and Z, E and A represent nitrogen. This is illustrated by formula Ig, wherein $R^1$, $R^2$, $R^3$, $R^4$, $R^5$ and L are as defined under formula I above:

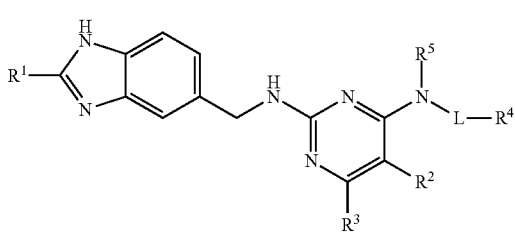

Ig

In another aspect of the invention, there is provided a compound of formula I, wherein Y, A and D represent carbon; and Z and E represent nitrogen. This is illustrated by formula Ih, wherein $R^1$, $R^2$, $R^3$, $R^4$, $R^5$ and L are as defined under formula I above:

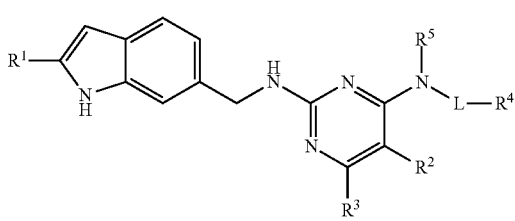

Ih

In another aspect of the invention, $R^4$ represents heteroaryl that is optionally substituted with one or more substituents. Such substituents include, but are not limited to, halogen, hydroxy, amino, nitro, cyano, $(C_1-C_4)$alkyl, $(C_1-C_4)$alkyl$(C_2-C_9)$heterocyclyl, $(C_1-C_4)$alkyl(CO)OH, $(C_1-C_4)$alkyl(CO)O$(C_1-C_4)$alkyl, $(C_1-C_4)$alkyl(CO)NH$_2$, $(C_1-C_4)$alkyl(CO)NH$(C_1-C_4)$alkyl, $(C_1-C_4)$alkyl(CO)NH$(C_1-C_4)$alkyl(CO)OH, $(C_1-C_4)$alkyl-OH, $(C_1-C_4)$alkyl-O$(C_6-C_{10})$aryl, $(C_1-C_4)$alkyl-O(CO)$(C_1-C_4)$alkyl, $(C_1-C_4)$alkyl-O(CO)$(C_6-C_{10})$aryl, $(C_1-C_4)$alkyl-NH$_2$, $(C_1-C_4)$alkyl-NH$(C_1-C_4)$alkyl, $(C_1-C_4)$alkyl-N[$(C_1-C_4)$alkyl][$(C_1-C_4)$-alkyl], $(C_1-C_4)$alkyl-NH(CO)$(C_1-C_4)$alkyl, $(C_1-C_4)$alkyl(CN), $(C_1-C_4)$alkyl$(C_6-C_{10})$aryl, (CO)OH, (CO)O$(C_1-C_4)$alkyl, (CO)NH$_2$, (CO)NH$(C_1-C_4)$alkyl, (CO)$(C_1-C_4)$alkyl, $(C_6-C_{10})$aryl, $(C_6-C_{10})$aryl-halogen, $(C_6-C_{10})$aryl-OH, $(C_6-C_{10})$aryl-O$(C_1-C_4)$alkyl, $(C_1-C_9)$heteroaryl, $(C_1-C_9)$heteroaryl-halogen, $(C_1-C_9)$heteroaryl-OH, $(C_1-C_9)$heteroaryl-O$(C_1-C_4)$alkyl, $(C_2-C_9)$heterocyclyl, $(C_2-C_9)$heterocyclyl$(C_1-C_4)$alkyl, $(C_2-C_9)$heterocyclyl$(C_1-C_4)$alkyl-OH, O(EtO)$_{1-3}$H, O(EtO)$_{1-3}$$(C_1-C_4)$alkyl, O$(C_6-C_{10})$aryl, O(CO)$(C_1-C_4)$alkyl, O(CO)$(C_6-C_{10})$aryl, OSO$_2$OH, NH$(C_1-C_4)$alkyl, N[$(C_1-C_4)$alkyl][$(C_1-C_4)$alkyl], NH(CO)$(C_1-C_4)$alkyl, NH(CO)$(C_6-C_{10})$aryl, and CF$_3$.

In another aspect of the invention, $R^4$ represents heteroaryl that is optionally substituted with one or more substituents. Such substituents include, but are not limited to, halogen, hydroxy, amino, nitro, cyano, $(C_1-C_4)$alkyl, $(C_1-C_4)$alkyl$(C_2-C_9)$heterocyclyl, $(C_1-C_4)$alkyl(CO)OH, $(C_1-C_4)$alkyl(CO)O$(C_1-C_4)$alkyl, $(C_1-C_4)$alkyl(CO)NH$_2$, $(C_1-C_4)$alkyl(CO)NH$(C_1-C_4)$alkyl, $(C_1-C_4)$alkyl(CO)NH$(C_1-C_4)$alkyl(CO)OH, $(C_1-C_4)$alkyl-OH, $(C_1-C_4)$alkyl-O$(C_1-C_4)$alkyl, $(C_1-C_4)$alkyl-O$(C_6-C_{10})$aryl, $(C_1-C_4)$alkyl-O(CO)$(C_1-C_4)$alkyl, $(C_1-C_4)$alkyl-O(CO)$(C_1-C_4)$alkyl-NH$_2$, $(C_1-C_4)$alkyl-O(CO)$(C_6-C_{10})$aryl, $(C_1-C_4)$alkyl-NH$_2$, $(C_1-C_4)$alkyl-NH$(C_1-C_4)$alkyl, $(C_1-C_4)$alkyl-N[$(C_1-C_4)$alkyl][$(C_1-C_4)$-alkyl], $(C_1-C_4)$alkyl-NH(CO)$(C_1-C_4)$alkyl, $(C_1-C_4)$alkyl-NH(CO)$(C_1-C_4)$alkyl-NH$_2$, $(C_1-C_4)$alkyl-NH(CO)$(C_6-C_{10})$aryl, $(C_1-C_4)$alkyl(CN), $(C_1-C_4)$alkyl$(C_6-C_{10})$aryl, (CO)OH, (CO)O$(C_1-C_4)$alkyl, (CO)NH$_2$, (CO)NH$(C_1-C_4)$alkyl, (CO)NH$(C_1-C_4)$alkyl(CO)OH, (CO)$(C_1-C_4)$alkyl, (CO)$(C_1-C_4)$alkyl$(C_6-C_{10})$aryl, (CO)$(C_1-C_4)$alkyl$(C_1-C_9)$heteroaryl, (CO)$(C_1-C_4)$alkyl$(C_2-C_9)$heterocyclyl, (CO)$(C_2-C_9)$heterocyclyl, (CO)$(C_6-C_{10})$aryl, (CO)$(C_1-C_9)$heteroaryl, $(C_6-C_{10})$aryl, $(C_6-C_{10})$aryl-halogen, $(C_6-C_{10})$aryl-OH, $(C_6-C_{10})$aryl-NH$_2$, $(C_6-C_{10})$aryl-O$(C_1-C_4)$alkyl, $(C_1-C_9)$heteroaryl, $(C_1-C_9)$heteroaryl-halogen, $(C_1-C_9)$heteroaryl-OH, $(C_1-C_9)$heteroaryl-NH$_2$, $(C_1-C_9)$heteroaryl$(C_1-C_4)$alkyl, $(C_1-C_9)$heteroaryl-O$(C_1-C_4)$alkyl, $(C_2-C_9)$heterocyclyl, $(C_2-C_9)$heterocyclyl$(C_1-C_4)$alkyl, $(C_2-C_9)$heterocyclyl$(C_1-C_4)$alkyl-OH, $(C_2-C_9)$heterocyclyl$(C_1-C_4)$alkyl-NH$_2$, O$(C_1-C_4)$alkyl, O$(C_1-C_4)$alkyl$(C_6-C_{10})$aryl, O$(C_1-C_4)$alkyl$(C_6-C_{10})$heteroaryl, O$(C_1-C_4)$alkyl$(C_2-C_9)$heterocyclyl, O$(C_1-C_4)$alkyl$(C_2-C_9)$heterocyclyl$(C_1-C_4)$alkyl, O$(C_1-C_4)$alkyl$(C_2-C_9)$heterocyclyl$(C_1-C_4)$alkyl-OH, O(EtO)$_{1-3}$H, O(EtO)$_{1-3}$$(C_1-C_4)$alkyl, O$(C_6-C_{10})$aryl, O(CO)$(C_1-C_4)$alkyl, O(CO)$(C_1-C_4)$alkyl-NH$_2$, O(CO)$(C_6-C_{10})$aryl, OSO$_2$$(C_1-C_4)$alkyl, OSO$_2$OH, NH$(C_1-C_4)$alkyl, N[$(C_1-C_4)$alkyl][$(C_1-C_4)$alkyl], NH(CO)$(C_1-C_4)$alkyl, NH(CO)$(C_1-C_4)$alkyl-NH$_2$, NH(CO)$(C_6-C_{10})$aryl, NHSO$_2$$(C_1-C_4)$alkyl, SO$_2$NH$_2$, and CF$_3$.

In another aspect of the invention, $R^4$ represents heteroaryl that is optionally substituted with one or more substituents selected from the group consisting of halogen, hydroxy, amino, nitro, cyano, $(C_1-C_4)$alkyl, $(C_1-C_4)$alkyl$(C_2-C_9)$heterocyclyl, $(C_1-C_4)$alkyl(CO)OH, $(C_1-C_4)$alkyl(CO)O$(C_1-C_4)$alkyl, $(C_1-C_4)$alkyl(CO)NH$_2$, $(C_1-C_4)$alkyl(CO)NH$(C_1-C_4)$alkyl, $(C_1-C_4)$alkyl(CO)NH$(C_1-C_4)$alkyl(CO)OH, $(C_1-C_4)$alkyl-OH, $(C_1-C_4)$alkyl-O$(C_1-C_4)$alkyl, $(C_1-C_4)$alkyl-O$(C_6-C_{10})$aryl, $(C_1-C_4)$alkyl-O(CO)$(C_1-C_4)$alkyl, $(C_1-C_4)$alkyl-O(CO)$(C_1-C_4)$alkyl-NH$_2$, $(C_1-C_4)$alkyl-O(CO)$(C_6-C_{10})$aryl, $(C_1-C_4)$alkyl-NH$_2$, $(C_1-C_4)$alkyl-NH$(C_1-C_4)$alkyl, $(C_1-C_4)$alkyl-N[$(C_1-C_4)$alkyl][$(C_1-C_4)$-alkyl], $(C_1-C_4)$alkyl-NH(CO)$(C_1-C_4)$alkyl, $(C_1-C_4)$alkyl-NH(CO)$(C_1-C_4)$alkyl-NH$_2$, $(C_1-C_4)$alkyl-NH(CO)$(C_6-C_{10})$aryl, $(C_1-C_4)$alkyl(CN), $(C_1-C_4)$alkyl$(C_6-C_{10})$aryl, (CO)OH, (CO)O$(C_1-C_4)$alkyl, (CO)NH$_2$, (CO)NH$(C_1-C_4)$alkyl, (CO)NH$(C_1-C_4)$alkyl(CO)OH, (CO)$(C_1-C_4)$alkyl, (CO)$(C_1-C_4)$alkyl$(C_6-C_{10})$aryl, (CO)$(C_1-C_4)$alkyl$(C_1-C_9)$heteroaryl, (CO)$(C_1-C_4)$alkyl$(C_2-C_9)$heterocyclyl, (CO)$(C_2-C_9)$heterocyclyl, (CO)$(C_6-C_{10})$aryl, (CO)$(C_1-C_9)$heteroaryl, $(C_6-C_{10})$aryl, $(C_6-C_{10})$aryl-halogen, $(C_6-C_{10})$aryl-OH, $(C_6-C_{10})$aryl-NH$_2$, $(C_6-C_{10})$aryl-O$(C_1-C_4)$alkyl, $(C_1-C_9)$heteroaryl, $(C_1-C_9)$heteroaryl-halogen, $(C_1-C_9)$heteroaryl-OH, $(C_1-C_9)$heteroaryl-NH$_2$, $(C_1-C_9)$heteroaryl$(C_1-C_4)$alkyl, $(C_1-C_9)$heteroaryl-O$(C_1-C_4)$alkyl, $(C_2-C_9)$heterocyclyl, $(C_2-C_9)$heterocyclyl$(C_1-C_4)$alkyl, $(C_2-C_9)$heterocyclyl$(C_1-C_4)$alkyl-OH, $(C_2-C_9)$heterocyclyl$(C_1-C_4)$alkyl-NH$_2$, O$(C_1-C_4)$alkyl, O$(C_1-C_4)$alkyl$(C_6-C_{10})$aryl, O$(C_1-C_4)$alkyl$(C_6-C_{10})$heteroaryl, O$(C_1-C_4)$alkyl$(C_2-C_9)$heterocyclyl, O$(C_1-C_4)$alkyl$(C_2-C_9)$heterocyclyl$(C_1-C_4)$alkyl, O$(C_1-C_4)$alkyl$(C_2-C_9)$heterocyclyl$(C_1-C_4)$alkyl-OH, O(EtO)$_{1-3}$H, O(EtO)$_{1-3}$$(C_1-C_4)$alkyl, O$(C_6-C_{10})$aryl, O(CO)$(C_1-C_4)$alkyl, O(CO)$(C_1-C_4)$alkyl-NH$_2$, O(CO)$(C_6-C_{10})$aryl, OCF$_3$, OSO$_2$$(C_1-C_4)$alkyl, OSO$_2$OH, NH$(C_1-C_4)$alkyl, N[$(C_1-C_4)$alkyl][$(C_1-C_4)$alkyl], NH(CO)$(C_1-C_4)$alkyl, NH(CO)$(C_1-C_4)$alkyl-NH$_2$, NH(CO)$(C_6-C_{10})$aryl, NHSO$_2$$(C_1-C_4)$alkyl, SO$_2$NH$_2$, and CF$_3$.

In another aspect of the invention, $R^4$ represents heteroaryl that is optionally substituted with one or more substituents selected from hydroxy, methyl, and methoxy.

In another aspect of the invention, L represents a bond.

In another aspect of the invention, L represents $C_1$-alkyl (methylene).

In another aspect of the invention, L represents $C_2$-alkyl (ethylene).

In another aspect of the invention, there is provided a compound of formula I, wherein L-$R^4$ is selected from:

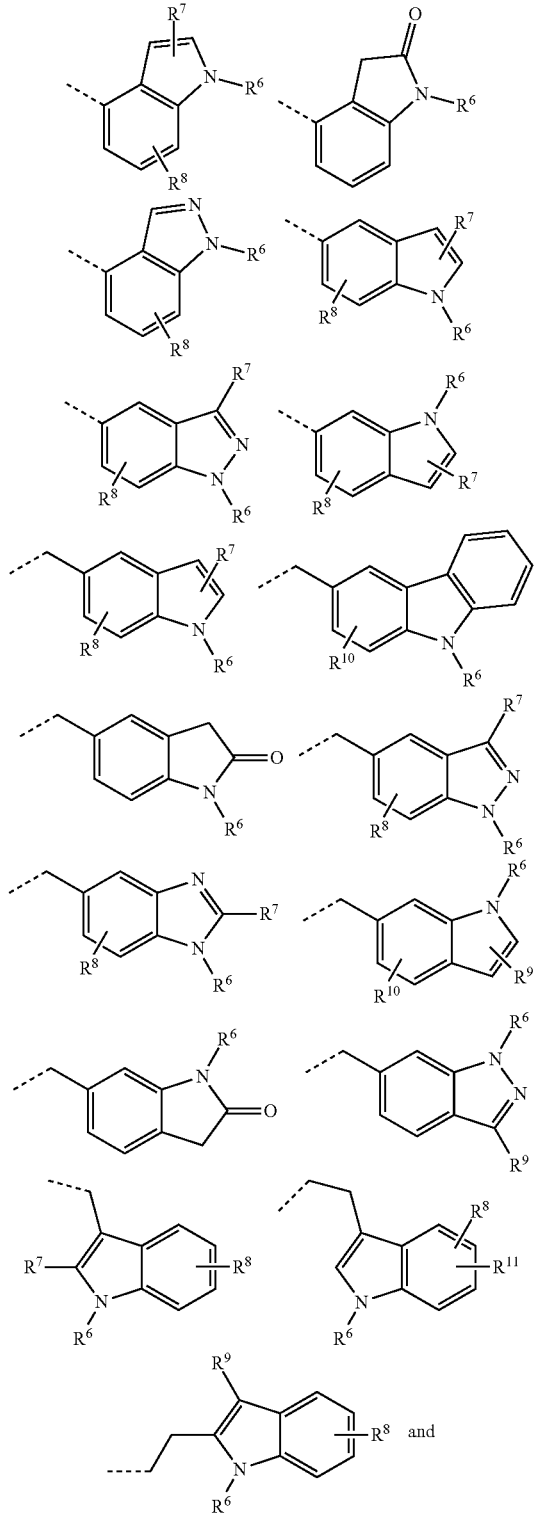

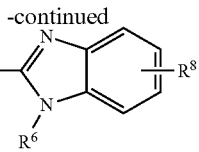

-continued wherein $R^6$ is selected from hydrogen and $(C_1-C_4)$alkyl;

$R^7$ is selected from hydrogen, halogen, nitro, cyano, $(C_1-C_4)$ alkyl, $(C_1-C_4)$alkyl(CO)OH, $(C_1-C_4)$alkyl(CO)O$(C_1-C_4)$ alkyl, $(C_1-C_4)$alkyl(CO)NH$_2$, $(C_1-C_4)$alkyl(CO)NH$(C_1-C_4)$alkyl, $(C_1-C_4)$alkyl-OH, $(C_1-C_4)$alkyl-O$(C_6-C_{10})$aryl, $(C_1-C_4)$alkyl-O(CO)$(C_1-C_4)$alkyl, $(C_1-C_4)$alkyl-O(CO)$(C_6-C_{10})$aryl, $(C_1-C_4)$alkyl-NH$_2$, $(C_1-C_4)$alkyl-NH$(C_1-C_4)$alkyl, $(C_1-C_4)$alkyl-N[$(C_1-C_4)$alkyl][$(C_1-C_4)$alkyl], $(C_1-C_4)$alkyl-NH(CO)$(C_1-C_4)$alkyl, $(C_1-C_4)$alkyl(CN), $(C_1-C_4)$alkyl$(C_6-C_{10})$aryl, $(C_1-C_4)$alkyl$(C_2-C_9)$heterocyclyl, (CO)OH, (CO)O$(C_1-C_4)$alkyl, (CO)NH$_2$, (CO)NH$(C_1-C_4)$alkyl, (CO)$(C_1-C_4)$alkyl, $(C_6-C_{10})$aryl, $(C_6-C_{10})$aryl-halogen, $(C_6-C_{10})$aryl-OH, $(C_6-C_{10})$aryl-O$(C_1-C_4)$alkyl, $(C_1-C_9)$heteroaryl, $(C_1-C_9)$heteroaryl-halogen, $(C_1-C_9)$heteroaryl-OH, $(C_1-C_9)$heteroaryl-O$(C_1-C_4)$alkyl, $(C_2-C_9)$heterocyclyl, $(C_2-C_9)$heterocyclyl$(C_1-C_4)$alkyl, and $(C_2-C_9)$heterocyclyl$(C_1-C_4)$alkyl-OH;

$R^8$ is selected from hydrogen, halogen, nitro, cyano, hydroxy, amino, $(C_1-C_4)$alkyl, $(C_1-C_4)$alkyl$(C_2-C_9)$heterocyclyl, $(C_1-C_4)$alkyl-NH$_2$, $(C_1-C_4)$alkyl-NH$(C_1-C_4)$alkyl, $(C_1-C_4)$alkyl-N[$(C_1-C_4)$alkyl][$(C_1-C_4)$-alkyl], $(C_1-C_4)$alkyl-NH(CO)$(C_1-C_4)$alkyl, $(C_1-C_4)$alkyl-NH(CO)$(C_6-C_{10})$aryl, (CO)$(C_1-C_4)$alkyl, (CO)OH, (CO)O$(C_1-C_4)$alkyl, (CO)NH$_2$, (CO)NH$(C_1-C_4)$alkyl, O$(C_1-C_4)$alkyl, O$(C_1-C_4)$alkyl$(C_6-C_{10})$aryl, O$(C_1-C_4)$alkyl$(C_1-C_9)$heteroaryl, O$(C_1-C_4)$alkyl$(C_2-C_9)$heterocyclyl, O$(C_1-C_4)$alkyl$(C_2-C_9)$heterocyclyl$(C_1-C_4)$alkyl, O$(C_1-C_4)$alkyl$(C_2-C_9)$heterocyclyl$(C_1-C_4)$alkyl-OH, O(EtO)$_{1-3}$H, O(EtO)$_{1-3}$$(C_1-C_4)$alkyl, O$(C_6-C_{10})$aryl, O(CO)$(C_1-C_4)$alkyl, O(CO)$(C_6-C_{10})$aryl, OSO$_2$OH, NH$(C_1-C_4)$alkyl, N[$(C_1-C_4)$alkyl][$(C_1-C_4)$alkyl], NH(CO)$(C_1-C_4)$alkyl, NH(CO)$(C_6-C_{10})$aryl, CF$_3$, $(C_6-C_{10})$aryl, $(C_6-C_{10})$aryl-halogen, $(C_6-C_{10})$aryl-OH, $(C_6-C_{10})$aryl-O$(C_1-C_4)$alkyl, $(C_1-C_9)$heteroaryl, $(C_1-C_9)$heteroaryl-halogen, $(C_1-C_9)$heteroaryl-OH, $(C_1-C_9)$heteroaryl-O$(C_1-C_4)$alkyl, $(C_2-C_9)$heterocyclyl, $(C_2-C_9)$heterocyclyl$(C_1-C_4)$alkyl, and $(C_2-C_9)$heterocyclyl $(C_1-C_4)$alkyl-OH;

$R^9$ is selected from hydrogen, halogen, $(C_1-C_4)$alkyl, $(C_1-C_4)$alkyl-OH, $(C_1-C_4)$alkyl-O$(C_1-C_4)$alkyl, (CO)OH, (CO)O$(C_1-C_4)$alkyl, (CO)NH$_2$, (CO)NH$(C_1-C_4)$alkyl, and $(C_6-C_{10})$aryl;

$R^{10}$ is selected from hydrogen, halogen, hydroxy, $(C_1-C_4)$ alkyl, $(C_1-C_4)$alkyl-OH, $(C_1-C_4)$alkyl-O$(C_1-C_4)$alkyl, and O$(C_1-C_4)$alkyl; and $R^{11}$ is selected from hydrogen, hydroxy, $(C_1-C_4)$alkyl, and O$(C_1-C_4)$alkyl.

In another aspect of the invention, there is provided a compound of formula I, wherein L-$R^4$ is selected from:

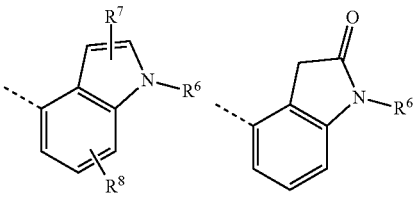

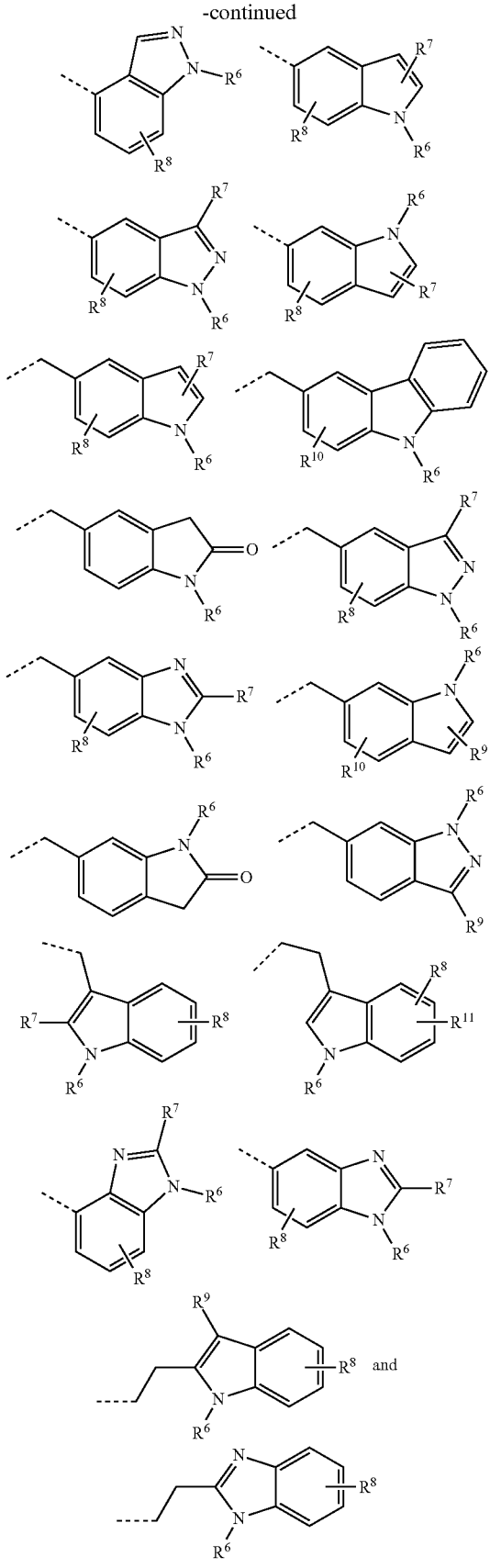

wherein $R^6$ is selected from hydrogen and $(C_1-C_4)$alkyl;

$R^7$ is selected from hydrogen, halogen, nitro, cyano, $(C_1-C_4)$alkyl, $(C_1-C_4)$alkyl(CO)OH, $(C_1-C_4)$alkyl(CO)O$(C_1-C_4)$alkyl, $(C_1-C_4)$alkyl(CO)NH$_2$, $(C_1-C_4)$alkyl(CO)NH$(C_1-C_4)$alkyl, $(C_1-C_4)$alkyl-OH, $(C_1-C_4)$alkyl-O$(C_6-C_{10})$aryl, $(C_1-C_4)$alkyl-O(CO)$(C_1-C_4)$alkyl, $(C_1-C_4)$alkyl-O(CO)$(C_6-C_{10})$aryl, $(C_1-C_4)$alkyl-NH$_2$, $(C_1-C_4)$alkyl-NH$(C_1-C_4)$alkyl, $(C_1-C_4)$alkyl-N[$(C_1-C_4)$alkyl][$(C_1-C_4)$alkyl], $(C_1-C_4)$alkyl-NH(CO)$(C_1-C_4)$alkyl, $(C_1-C_4)$alkyl(CN), $(C_1-C_4)$alkyl$(C_6-C_{10})$aryl, $(C_1-C_4)$alkyl$(C_2-C_9)$heterocyclyl, (CO)OH, (CO)O$(C_1-C_4)$alkyl, (CO)NH$_2$, (CO)NH$(C_1-C_4)$alkyl, (CO)$(C_1-C_4)$alkyl, $(C_6-C_{10})$aryl, $(C_6-C_{10})$aryl-halogen, $(C_6-C_{10})$aryl-OH, $(C_6-C_{10})$aryl-O$(C_1-C_4)$alkyl, $(C_1-C_9)$heteroaryl, $(C_1-C_9)$heteroaryl-halogen, $(C_1-C_9)$heteroaryl-OH, $(C_1-C_9)$heteroaryl-O$(C_1-C_4)$alkyl, $(C_2-C_9)$heterocyclyl, $(C_2-C_9)$heterocyclyl$(C_1-C_4)$alkyl, and $(C_2-C_9)$heterocyclyl$(C_1-C_4)$alkyl-OH;

$R^8$ is selected from hydrogen, halogen, nitro, cyano, hydroxy, amino, $(C_1-C_4)$alkyl, $(C_1-C_4)$alkyl$(C_2-C_9)$heterocyclyl, $(C_1-C_4)$alkyl-NH$_2$, $(C_1-C_4)$alkyl-NH$(C_1-C_4)$alkyl, $(C_1-C_4)$alkyl-N[$(C_1-C_4)$alkyl][$(C_1-C_4)$-alkyl], $(C_1-C_4)$alkyl-NH(CO)$(C_1-C_4)$alkyl, $(C_1-C_4)$alkyl-NH(CO)$(C_6-C_{10})$aryl, (CO)$(C_1-C_4)$alkyl, (CO)OH, (CO)O$(C_1-C_4)$alkyl, (CO)NH$_2$, (CO)NH$(C_1-C_4)$alkyl, O$(C_1-C_4)$alkyl, O$(C_1-C_4)$alkyl$(C_6-C_{10})$aryl, O$(C_1-C_4)$alkyl$(C_1-C_9)$heteroaryl, O$(C_1-C_4)$alkyl$(C_2-C_9)$heterocyclyl, O$(C_1-C_4)$alkyl$(C_2-C_9)$heterocyclyl$(C_1-C_4)$alkyl, O$(C_1-C_4)$alkyl$(C_2-C_9)$heterocyclyl$(C_1-C_4)$alkyl-OH, O(EtO)$_{1-3}$H, O(EtO)$_{1-3}$$(C_1-C_4)$alkyl, O$(C_6-C_{10})$aryl, O(CO)$(C_1-C_4)$alkyl, O(CO)$(C_6-C_{10})$aryl, OSO$_2$OH, NH$(C_1-C_4)$alkyl, N[$(C_1-C_4)$alkyl][$(C_1-C_4)$alkyl], NH(CO)$(C_1-C_4)$alkyl, NH(CO)$(C_6-C_{10})$aryl, CF$_3$, $(C_6-C_{10})$aryl, $(C_6-C_{10})$aryl-halogen, $(C_6-C_{10})$aryl-OH, $(C_6-C_{10})$aryl-O$(C_1-C_4)$alkyl, $(C_1-C_9)$heteroaryl, $(C_1-C_9)$heteroaryl-halogen, $(C_1-C_9)$heteroaryl-OH, $(C_1-C_9)$heteroaryl-O$(C_1-C_4)$alkyl, $(C_2-C_9)$heterocyclyl, $(C_2-C_9)$heterocyclyl$(C_1-C_4)$alkyl, and $(C_2-C_9)$heterocyclyl $(C_1-C_4)$alkyl-OH;

$R^9$ is selected from hydrogen, halogen, $(C_1-C_4)$alkyl, $(C_1-C_4)$alkyl-OH, $(C_1-C_4)$alkyl-O$(C_1-C_4)$alkyl, (CO)OH, (CO)O$(C_1-C_4)$alkyl, (CO)NH$_2$, (CO)NH$(C_1-C_4)$alkyl, and $(C_6-C_{10})$aryl;

$R^{10}$ is selected from hydrogen, halogen, hydroxy, $(C_1-C_4)$alkyl, $(C_1-C_4)$alkyl-OH, $(C_1-C_4)$alkyl-O$(C_1-C_4)$alkyl, and O$(C_1-C_4)$alkyl; and $R^{11}$ is selected from hydrogen, hydroxy, $(C_1-C_4)$alkyl, and O$(C_1-C_4)$alkyl.

In another aspect of the invention, there is provided a compound of formula I, wherein L-$R^4$ is selected from:

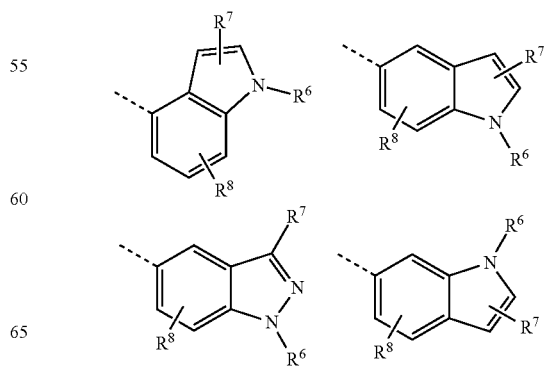

-continued

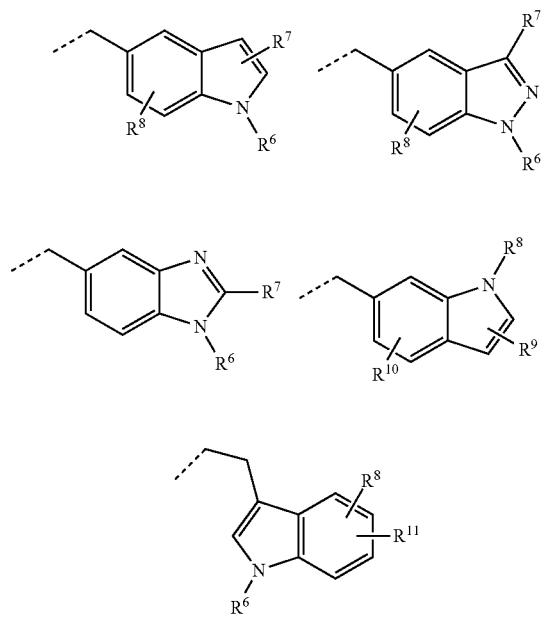

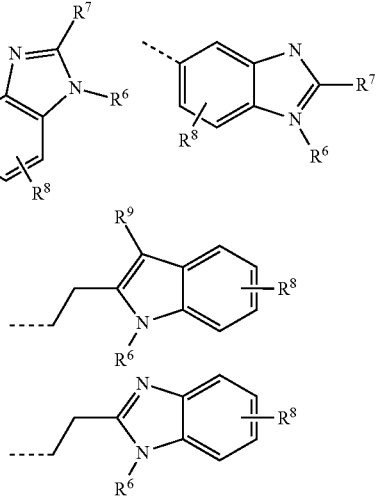

wherein
R⁶ represents hydrogen;
R⁷ is selected from hydrogen and (C₁-C₄)alkyl, preferably methyl;
R⁸, R⁹ and R¹⁰ represents hydrogen; and
R¹¹ is selected from hydrogen, hydroxy, (C₁-C₄)alkyl, preferably methyl, and O(C₁-C₄)alkyl, preferably methoxy.

In another aspect of the invention, there is provided a compound of formula I, wherein L-R⁴ is selected from:

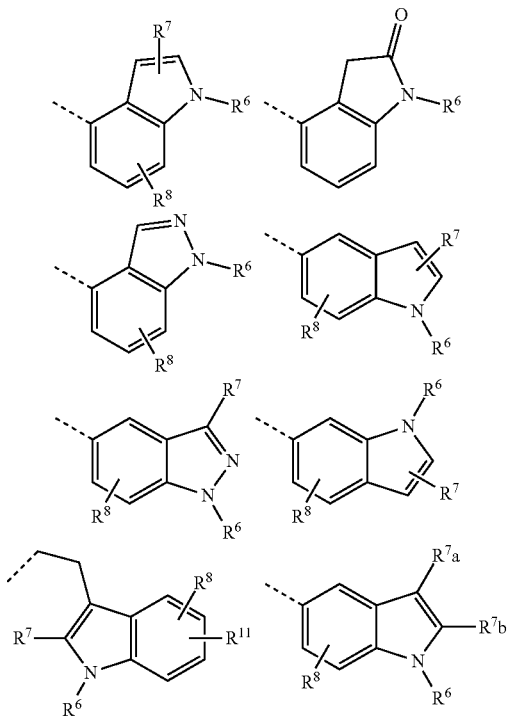

wherein R⁶ is selected from hydrogen and (C₁-C₄)alkyl;
R⁷ is selected from hydrogen, halogen, nitro, cyano, (C₁-C₄)alkyl, (C₁-C₄)alkyl(CO)OH, (C₁-C₄)alkyl(CO)O(C₁-C₄)alkyl, (C₁-C₄)alkyl(CO)NH₂, (C₁-C₄)alkyl(CO)NH(C₁-C₄)alkyl, (C₁-C₄)alkyl-OH, (C₁-C₄)alkyl-O(C₆-C₁₀)aryl, (C₁-C₄)alkyl-O(CO)(C₁-C₄)alkyl, (C₁-C₄)alkyl-O(CO)(C₆-C₁₀)aryl, (C₁-C₄)alkyl-NH₂, (C₁-C₄)alkyl-NH(C₁-C₄)alkyl, (C₁-C₄)alkyl-N[(C₁-C₄)alkyl][(C₁-C₄)alkyl], (C₁-C₄)alkyl-NH(CO)(C₁-C₄)alkyl, (C₁-C₄)alkyl(CN), (C₁-C₄)alkyl(C₆-C₁₀)aryl, (C₁-C₄)alkyl(C₂-C₉)heterocyclyl, (CO)OH, (CO)O(C₁-C₄)alkyl, (CO)NH₂, (CO)NH(C₁-C₄)alkyl, (CO)(C₁-C₄)alkyl, (C₆-C₁₀)aryl, (C₆-C₁₀)aryl-halogen, (C₆-C₁₀)aryl-OH, (C₆-C₁₀)aryl-O(C₁-C₄)alkyl, (C₁-C₉)heteroaryl, (C₁-C₉)heteroaryl-halogen, (C₁-C₉)heteroaryl-OH, (C₁-C₉)heteroaryl-O(C₁-C₄)alkyl, (C₂-C₉)heterocyclyl, (C₂-C₉)heterocyclyl(C₁-C₄)alkyl, and (C₂-C₉)heterocyclyl(C₁-C₄)alkyl-OH;
R⁷ᵃ and R⁷ᵇ are independently selected from hydrogen and (C₁-C₄)alkyl, preferably methyl;
R⁸ is selected from hydrogen, halogen, nitro, cyano, hydroxy, amino, (C₁-C₄)alkyl, (C₁-C₄)alkyl(C₂-C₉)heterocyclyl, (C₁-C₄)alkyl-NH₂, (C₁-C₄)alkyl-NH(C₁-C₄)alkyl, (C₁-C₄)alkyl-N[(C₁-C₄)alkyl][(C₁-C₄)-alkyl], (C₁-C₄)alkyl-NH(CO)(C₁-C₄)alkyl, (C₁-C₄)alkyl-NH(CO)(C₆-C₁₀)aryl, (CO)(C₁-C₄)alkyl, (CO)OH, (CO)O(C₁-C₄)alkyl, (CO)NH₂, (CO)NH(C₁-C₄)alkyl, O(C₁-C₄)alkyl, O(C₁-C₄)alkyl(C₆-C₁₀)aryl, O(C₁-C₄)alkyl(C₁-C₉)heteroaryl, O(C₁-C₄)alkyl(C₂-C₉)heterocyclyl, O(C₁-C₄)alkyl(C₂-C₉)heterocyclyl(C₁-C₄)alkyl, O(C₁-C₄)alkyl(C₂-C₉)heterocyclyl(C₁-C₄)alkyl-OH, O(EtO)₁₋₃H, O(EtO)₁₋₃(C₁-C₄)alkyl, O(C₆-C₁₀)aryl, OCF₃, O(CO)(C₁-C₄)alkyl, O(CO)(C₆-C₁₀)aryl, OSO₂OH, NH(C₁-C₄)alkyl, N[(C₁-C₄)alkyl][(C₁-C₄)alkyl], NH(CO)(C₁-C₄)alkyl, NH(CO)(C₆-C₁₀)aryl, CF₃, (C₆-C₁₀)aryl, (C₆-C₁₀)aryl-halogen, (C₆-C₁₀)aryl-OH, (C₆-C₁₀)aryl-O(C₁-C₄)alkyl, (C₁-C₉)heteroaryl, (C₁-C₉)heteroaryl-halogen, (C₁-C₉)heteroaryl-OH, (C₁-C₉)heteroaryl-O(C₁-C₄)alkyl, (C₂-C₉)heterocyclyl, (C₂-C₉)heterocyclyl(C₁-C₄)alkyl, and (C₂-C₉)heterocyclyl(C₁-C₄)alkyl-OH;
R⁹ is selected from hydrogen, halogen, (C₁-C₄)alkyl, (C₁-C₄)alkyl-OH, (C₁-C₄)alkyl-O(C₁-C₄)alkyl, (CO)OH, (CO)O(C₁-C₄)alkyl, (CO)NH₂, (CO)NH(C₁-C₄)alkyl, and (C₆-C₁₀)aryl; and
R¹¹ is selected from hydrogen, hydroxy, (C₁-C₄)alkyl, and O(C₁-C₄)alkyl.

In another aspect of the invention, there is provided a compound of formula I, wherein L-R⁴ is

[Chemical structure showing indole ring with substituents $R^{7a}$, $R^{7b}$, $R^8$, $R^6$]

wherein
$R^6$ and $R^8$ represent hydrogen;
$R^{7a}$ and $R^{7b}$ are independently selected from hydrogen and $(C_1-C_4)$alkyl, preferably methyl.

In another aspect of the invention, there is provided a compound of formula I, wherein $R^5$ represents hydrogen.

In another aspect of the invention, there is provided a compound of formula I, wherein $R^5$ represents methyl.

In another aspect of the invention, there is provided a compound of formula I, wherein $R^2$ represents amino.

In another aspect of the invention, there is provided a compound of formula I, wherein $R^2$ represents hydrogen.

In another aspect of the invention, there is provided a compound of formula I, wherein $R^2$ represents hydrogen; and $R^3$ represents hydrogen, methyl, trifluoromethyl or benzyl.

In another aspect of the invention, there is provided a compound of formula I, wherein
Z, D and E represent carbon;
Y and A represent nitrogen;
L represents a bond or $(C_1-C_2)$alkyl;
$R^1$ represents hydrogen or methyl;
$R^2$ represents hydrogen;
$R^3$ represents hydrogen or methyl;
$R^4$ represents a heteroaryl selected from indolyl, indazolyl, benzimidazolyl, and indolinonyl, said heteroaryl optionally substituted with one or two substituents selected from the group consisting of halogen, hydroxy, amino, nitro, cyano, $(C_1-C_4)$alkyl, $(C_1-C_4)$alkyl$(C_2-C_9)$heterocyclyl, $(C_1-C_4)$alkyl(CO)OH, $(C_1-C_4)$alkyl(CO)O$(C_1-C_4)$alkyl, $(C_1-C_4)$alkyl(CO)NH$_2$, $(C_1-C_4)$alkyl(CO)NH$(C_1-C_4)$alkyl, $(C_1-C_4)$alkyl(CO)NH$(C_1-C_4)$alkyl(CO)OH, $(C_1-C_4)$alkyl-OH, $(C_1-C_4)$alkyl-O$(C_1-C_4)$alkyl, $(C_1-C_4)$alkyl-O$(C_6-C_{10})$aryl, $(C_1-C_4)$alkyl-O(CO)$(C_1-C_4)$alkyl, $(C_1-C_4)$alkyl-O(CO)$(C_1-C_4)$alkyl-NH$_2$, $(C_1-C_4)$alkyl-O(CO)$(C_6-C_{10})$aryl, $(C_1-C_4)$alkyl-NH$_2$, $(C_1-C_4)$alkyl-NH$(C_1-C_4)$alkyl, $(C_1-C_4)$alkyl-N[$(C_1-C_4)$alkyl][$(C_1-C_4)$-alkyl], $(C_1-C_4)$alkyl-NH(CO)$(C_1-C_4)$alkyl, $(C_1-C_4)$alkyl-NH(CO)$(C_1-C_4)$alkyl-NH$_2$, $(C_1-C_4)$alkyl-NH(CO)$(C_6-C_{10})$aryl, $(C_1-C_4)$alkyl(CN), $(C_1-C_4)$alkyl$(C_6-C_{10})$aryl, (CO)OH, (CO)O$(C_1-C_4)$alkyl, (CO)NH$_2$, (CO)NH$(C_1-C_4)$alkyl, (CO)NH$(C_1-C_4)$alkyl(CO)OH, (CO)$(C_1-C_4)$alkyl, (CO)$(C_1-C_4)$alkyl$(C_6-C_{10})$aryl, (CO)$(C_1-C_4)$alkyl$(C_1-C_9)$heteroaryl, (CO)$(C_1-C_4)$alkyl$(C_2-C_9)$heterocyclyl, (CO)$(C_2-C_9)$heterocyclyl, (CO)$(C_6-C_{10})$aryl, (CO)$(C_1-C_9)$heteroaryl, $(C_6-C_{10})$aryl, $(C_6-C_{10})$aryl-halogen, $(C_6-C_{10})$aryl-OH, $(C_6-C_{10})$aryl-NH$_2$, $(C_6-C_{10})$aryl-O$(C_1-C_4)$alkyl, $(C_1-C_9)$heteroaryl, $(C_1-C_9)$heteroaryl-halogen, $(C_1-C_9)$heteroaryl-OH, $(C_1-C_9)$heteroaryl-NH$_2$, $(C_1-C_9)$heteroaryl$(C_1-C_4)$alkyl, $(C_1-C_9)$heteroaryl-O$(C_1-C_4)$alkyl, $(C_2-C_9)$heterocyclyl, $(C_2-C_9)$heterocyclyl$(C_1-C_4)$alkyl, $(C_2-C_9)$heterocyclyl$(C_1-C_4)$alkyl-OH, $(C_2-C_9)$heterocyclyl$(C_1-C_4)$alkyl-NH$_2$, O$(C_1-C_4)$alkyl, O$(C_1-C_4)$alkyl$(C_6-C_{10})$aryl, O$(C_1-C_4)$alkyl$(C_6-C_{10})$heteroaryl, O$(C_1-C_4)$alkyl$(C_2-C_9)$heterocyclyl, O$(C_1-C_4)$alkyl$(C_2-C_9)$heterocyclyl$(C_1-C_4)$alkyl, O$(C_1-C_4)$alkyl$(C_2-C_9)$heterocyclyl$(C_1-C_4)$alkyl-OH, O(EtO)$_{1-3}$H, O(EtO)$_{1-3}$$(C_1-C_4)$alkyl, O$(C_6-C_{10})$aryl, O(CO)$(C_1-C_4)$alkyl, O(CO)$(C_1-C_4)$alkyl-NH$_2$, O(CO)$(C_6-C_{10})$aryl, OCF$_3$, OSO$_2$$(C_1-C_4)$alkyl, OSO$_2$OH, NH$(C_1-C_4)$alkyl, N[$(C_1-C_4)$alkyl][$(C_1-C_4)$alkyl], NH(CO)$(C_1-C_4)$alkyl, NH(CO)$(C_1-C_4)$alkyl-NH$_2$, NH(CO)$(C_6-C_{10})$aryl, NHSO$_2$$(C_1-C_4)$alkyl, SO$_2$NH$_2$, and CF$_3$; and
$R^5$ represents hydrogen or methyl.

In another aspect of the invention, there is provided a compound of formula I, wherein
Z and E represent carbon;
Y, D, and A represent nitrogen;
L represents a bond or $(C_1-C_2)$alkyl;
$R^2$ represents hydrogen;
$R^3$ represents hydrogen or methyl;
$R^4$ represents a heteroaryl selected from indolyl, indazolyl, benzimidazolyl, and indolinonyl, said heteroaryl optionally substituted with one or two substituents selected from the group consisting of halogen, hydroxy, amino, nitro, cyano, $(C_1-C_4)$alkyl, $(C_1-C_4)$alkyl$(C_2-C_9)$heterocyclyl, $(C_1-C_4)$alkyl(CO)OH, $(C_1-C_4)$alkyl(CO)O$(C_1-C_4)$alkyl, $(C_1-C_4)$alkyl(CO)NH$_2$, $(C_1-C_4)$alkyl(CO)NH$(C_1-C_4)$alkyl, $(C_1-C_4)$alkyl(CO)NH$(C_1-C_4)$alkyl(CO)OH, $(C_1-C_4)$alkyl-OH, $(C_1-C_4)$alkyl-O$(C_1-C_4)$alkyl, $(C_1-C_4)$alkyl-O$(C_6-C_{10})$aryl, $(C_1-C_4)$alkyl-O(CO)$(C_1-C_4)$alkyl, $(C_1-C_4)$alkyl-O(CO)$(C_1-C_4)$alkyl-NH$_2$, $(C_1-C_4)$alkyl-O(CO)$(C_6-C_{10})$aryl, $(C_1-C_4)$alkyl-NH$_2$, $(C_1-C_4)$alkyl-NH$(C_1-C_4)$alkyl, $(C_1-C_4)$alkyl-N[$(C_1-C_4)$alkyl][$(C_1-C_4)$-alkyl], $(C_1-C_4)$alkyl-NH(CO)$(C_1-C_4)$alkyl, $(C_1-C_4)$alkyl-NH(CO)$(C_1-C_4)$alkyl-NH$_2$, $(C_1-C_4)$alkyl-NH(CO)$(C_6-C_{10})$aryl, $(C_1-C_4)$alkyl(CN), $(C_1-C_4)$alkyl$(C_6-C_{10})$aryl, (CO)OH, (CO)O$(C_1-C_4)$alkyl, (CO)NH$_2$, (CO)NH$(C_1-C_4)$alkyl, (CO)NH$(C_1-C_4)$alkyl(CO)OH, (CO)$(C_1-C_4)$alkyl, (CO)$(C_1-C_4)$alkyl$(C_6-C_{10})$aryl, (CO)$(C_1-C_4)$alkyl$(C_1-C_9)$heteroaryl, (CO)$(C_1-C_4)$alkyl$(C_2-C_9)$heterocyclyl, (CO)$(C_2-C_9)$heterocyclyl, (CO)$(C_6-C_{10})$aryl, (CO)$(C_1-C_9)$heteroaryl, $(C_6-C_{10})$aryl, $(C_6-C_{10})$aryl-halogen, $(C_6-C_{10})$aryl-OH, $(C_6-C_{10})$aryl-NH$_2$, $(C_6-C_{10})$aryl-O$(C_1-C_4)$alkyl, $(C_1-C_9)$heteroaryl, $(C_1-C_9)$heteroaryl-halogen, $(C_1-C_9)$heteroaryl-OH, $(C_1-C_9)$heteroaryl-NH$_2$, $(C_1-C_9)$heteroaryl$(C_1-C_4)$alkyl, $(C_1-C_9)$heteroaryl-O$(C_1-C_4)$alkyl, $(C_2-C_9)$heterocyclyl, $(C_2-C_9)$heterocyclyl$(C_1-C_4)$alkyl, $(C_2-C_9)$heterocyclyl$(C_1-C_4)$alkyl-OH, $(C_2-C_9)$heterocyclyl$(C_1-C_4)$alkyl-NH$_2$, O$(C_1-C_4)$alkyl, O$(C_1-C_4)$alkyl$(C_6-C_{10})$aryl, O$(C_1-C_4)$alkyl$(C_6-C_{10})$heteroaryl, O$(C_1-C_4)$alkyl$(C_2-C_9)$heterocyclyl, O$(C_1-C_4)$alkyl$(C_2-C_9)$heterocyclyl$(C_1-C_4)$alkyl, O$(C_1-C_4)$alkyl$(C_2-C_9)$heterocyclyl$(C_1-C_4)$alkyl-OH, O(EtO)$_{1-3}$H, O(EtO)$_{1-3}$$(C_1-C_4)$alkyl, O$(C_6-C_{10})$aryl, O(CO)$(C_1-C_4)$alkyl, O(CO)$(C_1-C_4)$alkyl-NH$_2$, O(CO)$(C_6-C_{10})$aryl, OCF$_3$, OSO$_2$$(C_1-C_4)$alkyl, OSO$_2$OH, NH$(C_1-C_4)$alkyl, N[$(C_1-C_4)$alkyl][$(C_1-C_4)$alkyl], NH(CO)$(C_1-C_4)$alkyl, NH(CO)$(C_1-C_4)$alkyl-NH$_2$, NH(CO)$(C_6-C_{10})$aryl, NHSO$_2$$(C_1-C_4)$alkyl, SO$_2$NH$_2$, and CF$_3$; and
$R^5$ represents hydrogen or methyl.

In another aspect of the invention, there is provided a compound of formula I, wherein
Z and D represent carbon;
Y, E and A represent nitrogen;
L represents a bond or $(C_1-C_2)$alkyl;
$R^1$ represents hydrogen;
$R^2$ represents hydrogen;
$R^3$ represents hydrogen or methyl;
$R^4$ represents a heteroaryl selected from indolyl, indazolyl, benzimidazolyl, and indolinonyl, said heteroaryl optionally substituted with one or two substituents selected from the group consisting of halogen, hydroxy, amino, nitro, cyano, (C₁-C₄)alkyl, (C₁-C₄)alkyl(C₂-C₉)heterocyclyl, (C₁-C₄)alkyl(CO)OH, (C₁-C₄)alkyl(CO)O(C₁-C₄)alkyl, (C₁-C₄)alkyl(CO)NH₂, (C₁-C₄)alkyl(CO)NH(C₁-C₄)alkyl, (C₁-C₄)alkyl(CO)NH(C₁-C₄)alkyl(CO)OH, (C₁-C₄)alkyl-OH, (C₁-C₄)alkyl-O(C₁-C₄)alkyl, (C₁-C₄)alkyl-O(C₆-C₁₀)aryl, (C₁-C₄)alkyl-O(CO)(C₁-C₄)alkyl, (C₁-C₄)alkyl-O(CO)(C₁-C₄)alkyl-NH₂, (C₁-C₄)alkyl-O(CO)(C₆-C₁₀)aryl, (C₁-C₄)alkyl-NH₂, (C₁-C₄)alkyl-NH(C₁-C₄)alkyl, (C₁-C₄)alkyl-N[(C₁-C₄)alkyl][(C₁-C₄)-alkyl], (C₁-C₄)alkyl-NH(CO)(C₁-C₄)alkyl, (C₁-C₄)alkyl-NH(CO)(C₁-C₄)alkyl-NH₂, (C₁-C₄)alkyl-NH(CO)(C₆-C₁₀)aryl, (C₁-C₄)alkyl(CN), (C₁-C₄)alkyl(C₆-C₁₀)aryl, (CO)OH, (CO)O(C₁-C₄)alkyl, (CO)NH₂, (CO)NH(C₁-C₄)alkyl, (CO)NH(C₁-C₄)alkyl(CO)OH, (CO)(C₁-C₄)alkyl, (CO)(C₁-C₄)alkyl(C₆-C₁₀)aryl, (CO)(C₁-C₄)alkyl(C₁-C₉)heteroaryl, (CO)(C₁-C₄)alkyl(C₂-C₉)heterocyclyl, (CO)(C₂-C₉)heterocyclyl, (CO)(C₆-C₁₀)aryl, (CO)(C₁-C₉)heteroaryl, (C₆-C₁₀)aryl, (C₆-C₁₀)aryl-halogen, (C₆-C₁₀)aryl-OH, (C₆-C₁₀)aryl-NH₂, (C₆-C₁₀)aryl-O(C₁-C₄)alkyl, (C₁-C₉)heteroaryl, (C₁-C₉)heteroaryl-halogen, (C₁-C₉)heteroaryl-OH, (C₁-C₉)heteroaryl-NH₂, (C₁-C₉)heteroaryl(C₁-C₄)alkyl, (C₁-C₉)heteroaryl-O(C₁-C₄)alkyl, (C₂-C₉)heterocyclyl, (C₂-C₉)heterocyclyl(C₁-C₄)alkyl, (C₂-C₉)heterocyclyl(C₁-C₄)alkyl-OH, (C₂-C₉)heterocyclyl(C₁-C₄)alkyl-NH₂, O(C₁-C₄)alkyl, O(C₁-C₄)alkyl(C₆-C₁₀)aryl, O(C₁-C₄)alkyl(C₆-C₁₀)heteroaryl, O(C₁-C₄)alkyl(C₂-C₉)heterocyclyl, O(C₁-C₄)alkyl(C₂-C₉)heterocyclyl(C₁-C₄)alkyl, O(C₁-C₄)alkyl(C₂-C₉)heterocyclyl(C₁-C₄)alkyl-OH, O(EtO)₁₋₃H, O(EtO)₁₋₃(C₁-C₄)alkyl, O(C₆-C₁₀)aryl, O(CO)(C₁-C₄)alkyl, O(CO)(C₁-C₄)alkyl-NH₂, O(CO)(C₆-C₁₀)aryl, OCF₃, OSO₂(C₁-C₄)alkyl, OSO₂OH, NH(C₁-C₄)alkyl, N[(C₁-C₄)alkyl][(C₁-C₄)alkyl], NH(CO)(C₁-C₄)alkyl, NH(CO)(C₁-C₄)alkyl-NH₂, NH(CO)(C₆-C₁₀)aryl, NHSO₂(C₁-C₄)alkyl, SO₂NH₂, and CF₃; and R⁵ represents hydrogen or methyl.

In another aspect of the invention, there is provided a compound of formula I,
wherein Z, A and D represent carbon;
Y and E represent nitrogen;
L represents a bond or (C₁-C₂)alkyl;
R¹ represents hydrogen or methyl;
R² represents hydrogen;
R³ represents hydrogen or methyl;
R⁴ represents a heteroaryl selected from indolyl, indazolyl, benzimidazolyl, and indolinonyl, said heteroaryl optionally substituted with one or two substituents selected from the group consisting of halogen, hydroxy, amino, nitro, cyano, (C₁-C₄)alkyl, (C₁-C₄)alkyl(C₂-C₉)heterocyclyl, (C₁-C₄)alkyl(CO)OH, (C₁-C₄)alkyl(CO)O(C₁-C₄)alkyl, (C₁-C₄)alkyl(CO)NH₂, (C₁-C₄)alkyl(CO)NH(C₁-C₄)alkyl, (C₁-C₄)alkyl(CO)NH(C₁-C₄)alkyl(CO)OH, (C₁-C₄)alkyl-OH, (C₁-C₄)alkyl-O(C₁-C₄)alkyl, (C₁-C₄)alkyl-O(C₆-C₁₀)aryl, (C₁-C₄)alkyl-O(CO)(C₁-C₄)alkyl, (C₁-C₄)alkyl-O(CO)(C₁-C₄)alkyl-NH₂, (C₁-C₄)alkyl-O(CO)(C₆-C₁₀)aryl, (C₁-C₄)alkyl-NH₂, (C₁-C₄)alkyl-NH(C₁-C₄)alkyl, (C₁-C₄)alkyl-N[(C₁-C₄)alkyl][(C₁-C₄)-alkyl], (C₁-C₄)alkyl-NH(CO)(C₁-C₄)alkyl, (C₁-C₄)alkyl-NH(CO)(C₁-C₄)alkyl-NH₂, (C₁-C₄)alkyl-NH(CO)(C₆-C₁₀)aryl, (C₁-C₄)alkyl(CN), (C₁-C₄)alkyl(C₆-C₁₀)aryl, (CO)OH, (CO)O(C₁-C₄)alkyl, (CO)NH₂, (CO)NH(C₁-C₄)alkyl, (CO)NH(C₁-C₄)alkyl(CO)OH, (CO)(C₁-C₄)alkyl, (CO)(C₁-C₄)alkyl(C₆-C₁₀)aryl, (CO)(C₁-C₄)alkyl(C₁-C₉)heteroaryl, (CO)(C₁-C₄)alkyl(C₂-C₉)heterocyclyl, (CO)(C₂-C₉)heterocyclyl, (CO)(C₆-C₁₀)aryl, (CO)(C₁-C₉)heteroaryl, (C₆-C₁₀)aryl, (C₆-C₁₀)aryl-halogen, (C₆-C₁₀)aryl-OH, (C₆-C₁₀)aryl-NH₂, (C₆-C₁₀)aryl-O(C₁-C₄)alkyl, (C₁-C₉)heteroaryl, (C₁-C₉)heteroaryl-halogen, (C₁-C₉)heteroaryl-OH, (C₁-C₉)heteroaryl-NH₂, (C₁-C₉)heteroaryl(C₁-C₄)alkyl, (C₁-C₉)heteroaryl-O(C₁-C₄)alkyl, (C₂-C₉)heterocyclyl, (C₂-C₉)heterocyclyl(C₁-C₄)alkyl, (C₂-C₉)heterocyclyl(C₁-C₄)alkyl-OH, (C₂-C₉)heterocyclyl(C₁-C₄)alkyl-NH₂, O(C₁-C₄)alkyl, O(C₁-C₄)alkyl(C₆-C₁₀)aryl, O(C₁-C₄)alkyl(C₆-C₁₀)heteroaryl, O(C₁-C₄)alkyl(C₂-C₉)heterocyclyl, O(C₁-C₄)alkyl(C₂-C₉)heterocyclyl(C₁-C₄)alkyl, O(C₁-C₄)alkyl(C₂-C₉)heterocyclyl(C₁-C₄)alkyl-OH, O(EtO)₁₋₃H, O(EtO)₁₋₃(C₁-C₄)alkyl, O(C₆-C₁₀)aryl, O(CO)(C₁-C₄)alkyl, O(CO)(C₁-C₄)alkyl-NH₂, O(CO)(C₆-C₁₀)aryl, OCF₃, OSO₂(C₁-C₄)alkyl, OSO₂OH, NH(C₁-C₄)alkyl, N[(C₁-C₄)alkyl][(C₁-C₄)alkyl], NH(CO)(C₁-C₄)alkyl, NH(CO)(C₁-C₄)alkyl-NH₂, NH(CO)(C₆-C₁₀)aryl, NHSO₂(C₁-C₄)alkyl, SO₂NH₂, and CF₃; and R⁵ represents hydrogen or methyl.

In another aspect of the invention, there is provided a compound of formula I,
wherein
Y, D and E represent carbon;
Z and A represent nitrogen;
L represents a bond or (C₁-C₂)alkyl;
R¹ represents hydrogen or methyl;
R² represents hydrogen;
R³ represents hydrogen or methyl;
R⁴ represents a heteroaryl selected from indolyl, indazolyl, benzimidazolyl, and indolinonyl, said heteroaryl optionally substituted with one or two substituents selected from the group consisting of halogen, hydroxy, amino, nitro, cyano, (C₁-C₄)alkyl, (C₁-C₄)alkyl(C₂-C₉)heterocyclyl, (C₁-C₄)alkyl(CO)OH, (C₁-C₄)alkyl(CO)O(C₁-C₄)alkyl, (C₁-C₄)alkyl(CO)NH₂, (C₁-C₄)alkyl(CO)NH(C₁-C₄)alkyl, (C₁-C₄)alkyl(CO)NH(C₁-C₄)alkyl(CO)OH, (C₁-C₄)alkyl-OH, (C₁-C₄)alkyl-O(C₁-C₄)alkyl, (C₁-C₄)alkyl-O(C₆-C₁₀)aryl, (C₁-C₄)alkyl-O(CO)(C₁-C₄)alkyl, (C₁-C₄)alkyl-O(CO)(C₁-C₄)alkyl-NH₂, (C₁-C₄)alkyl-O(CO)(C₆-C₁₀)aryl, (C₁-C₄)alkyl-NH₂, (C₁-C₄)alkyl-NH(C₁-C₄)alkyl, (C₁-C₄)alkyl-N[(C₁-C₄)alkyl][(C₁-C₄)-alkyl], (C₁-C₄)alkyl-NH(CO)(C₁-C₄)alkyl, (C₁-C₄)alkyl-NH(CO)(C₁-C₄)alkyl-NH₂, (C₁-C₄)alkyl-NH(CO)(C₆-C₁₀)aryl, (C₁-C₄)alkyl(CN), (C₁-C₄)alkyl(C₆-C₁₀)aryl, (CO)OH, (CO)O(C₁-C₄)alkyl, (CO)NH₂, (CO)NH(C₁-C₄)alkyl, (CO)NH(C₁-C₄)alkyl(CO)OH, (CO)(C₁-C₄)alkyl, (CO)(C₁-C₄)alkyl(C₆-C₁₀)aryl, (CO)(C₁-C₄)alkyl(C₁-C₉)heteroaryl, (CO)(C₁-C₄)alkyl(C₂-C₉)heterocyclyl, (CO)(C₂-C₉)heterocyclyl, (CO)(C₆-C₁₀)aryl, (CO)(C₁-C₉)heteroaryl, (C₆-C₁₀)aryl, (C₆-C₁₀)aryl-halogen, (C₆-C₁₀)aryl-OH, (C₆-C₁₀)aryl-NH₂, (C₆-C₁₀)aryl-O(C₁-C₄)alkyl, (C₁-C₉)heteroaryl, (C₁-C₉)heteroaryl-halogen, (C₁-C₉)heteroaryl-OH, (C₁-C₉)heteroaryl-NH₂, (C₁-C₉)heteroaryl(C₁-C₄)alkyl, (C₁-C₉)heteroaryl-O(C₁-C₄)alkyl, (C₂-C₉)heterocyclyl, (C₂-C₉)heterocyclyl(C₁-C₄)alkyl, (C₂-C₉)heterocyclyl(C₁-C₄)alkyl-OH, (C₂-C₉)heterocyclyl(C₁-C₄)alkyl-NH₂, O(C₁-C₄)alkyl, O(C₁-C₄)alkyl(C₆-C₁₀)aryl, O(C₁-C₄)alkyl(C₆-C₁₀)heteroaryl, O(C₁-C₄)alkyl(C₂-C₉)heterocyclyl, O(C₁-C₄)alkyl(C₂-C₉)heterocyclyl(C₁-C₄)alkyl, O(C₁-C₄)alkyl(C₂-C₉)heterocyclyl(C₁-C₄)alkyl-OH, O(EtO)₁₋₃H, O(EtO)₁₋₃(C₁-C₄)alkyl, O(C₆-C₁₀)aryl, O(CO)(C₁-C₄)alkyl, O(CO)(C₁-C₄)alkyl-NH₂, O(CO)(C₆-C₁₀)aryl, OCF₃, OSO₂(C₁-C₄)alkyl, OSO₂OH, NH(C₁-C₄)alkyl, N[(C₁-C₄)alkyl][(C₁-C₄)alkyl], NH(CO)(C₁-C₄)alkyl, NH(CO)(C₁-C₄)alkyl-NH₂, NH(CO)(C₆-C₁₀)aryl, NHSO₂(C₁-C₄)alkyl, SO₂NH₂, and CF₃; and R⁵ represents hydrogen or methyl.

In another aspect of the invention, there is provided a compound of formula I,
wherein
Y and E represent carbon;
Z, D, and A represent nitrogen;
L represents a bond or $(C_1-C_2)$alkyl;
$R^2$ represents hydrogen;
$R^3$ represents hydrogen or methyl;
$R^4$ represents a heteroaryl selected from indolyl, indazolyl, benzimidazolyl, and indolinonyl, said heteroaryl optionally substituted with one or two substituents selected from the group consisting of halogen, hydroxy, amino, nitro, cyano, $(C_1-C_4)$alkyl, $(C_1-C_4)$alkyl$(C_2-C_9)$heterocyclyl, $(C_1-C_4)$alkyl(CO)OH, $(C_1-C_4)$alkyl(CO)O$(C_1-C_4)$alkyl, $(C_1-C_4)$alkyl(CO)NH$_2$, $(C_1-C_4)$alkyl(CO)NH$(C_1-C_4)$alkyl, $(C_1-C_4)$alkyl(CO)NH$(C_1-C_4)$alkyl(CO)OH, $(C_1-C_4)$alkyl-OH, $(C_1-C_4)$alkyl-O$(C_1-C_4)$alkyl, $(C_1-C_4)$alkyl-O$(C_6-C_{10})$aryl, $(C_1-C_4)$alkyl-O(CO)$(C_1-C_4)$alkyl, $(C_1-C_4)$alkyl-O(CO)$(C_1-C_4)$alkyl-NH$_2$, $(C_1-C_4)$alkyl-O(CO)$(C_6-C_{10})$aryl, $(C_1-C_4)$alkyl-NH$_2$, $(C_1-C_4)$alkyl-NH$(C_1-C_4)$alkyl, $(C_1-C_4)$alkyl-N[$(C_1-C_4)$alkyl][$(C_1-C_4)$-alkyl], $(C_1-C_4)$alkyl-NH(CO)$(C_1-C_4)$alkyl, $(C_1-C_4)$alkyl-NH(CO)$(C_1-C_4)$alkyl-NH$_2$, $(C_1-C_4)$alkyl-NH(CO)$(C_6-C_{10})$aryl, $(C_1-C_4)$alkyl(CN), $(C_1-C_4)$alkyl$(C_6-C_{10})$aryl, (CO)OH, (CO)O$(C_1-C_4)$alkyl, (CO)NH$_2$, (CO)NH$(C_1-C_4)$alkyl, (CO)NH$(C_1-C_4)$alkyl(CO)OH, (CO)$(C_1-C_4)$alkyl, (CO)$(C_1-C_4)$alkyl$(C_6-C_{10})$aryl, (CO)$(C_1-C_4)$alkyl$(C_1-C_9)$heteroaryl, (CO)$(C_1-C_4)$alkyl$(C_2-C_9)$heterocyclyl, (CO)$(C_2-C_9)$heterocyclyl, (CO)$(C_6-C_{10})$aryl, (CO)$(C_1-C_9)$heteroaryl, $(C_6-C_{10})$aryl, $(C_6-C_{10})$aryl-halogen, $(C_6-C_{10})$aryl-OH, $(C_6-C_{10})$aryl-NH$_2$, $(C_6-C_{10})$aryl-O$(C_1-C_4)$alkyl, $(C_1-C_9)$heteroaryl, $(C_1-C_9)$heteroaryl-halogen, $(C_1-C_9)$heteroaryl-OH, $(C_1-C_9)$heteroaryl-NH$_2$, $(C_1-C_9)$heteroaryl$(C_1-C_4)$alkyl, $(C_1-C_9)$heteroaryl-O$(C_1-C_4)$alkyl, $(C_2-C_9)$heterocyclyl, $(C_2-C_9)$heterocyclyl$(C_1-C_4)$alkyl, $(C_2-C_9)$heterocyclyl$(C_1-C_4)$alkyl-OH, $(C_2-C_9)$heterocyclyl$(C_1-C_4)$alkyl-NH$_2$, O$(C_1-C_4)$alkyl, O$(C_1-C_4)$alkyl$(C_6-C_{10})$aryl, O$(C_1-C_4)$alkyl$(C_6-C_{10})$heteroaryl, O$(C_1-C_4)$alkyl$(C_2-C_9)$heterocyclyl, O$(C_1-C_4)$alkyl$(C_2-C_9)$heterocyclyl$(C_1-C_4)$alkyl, O$(C_1-C_4)$alkyl$(C_2-C_9)$heterocyclyl$(C_1-C_4)$alkyl-OH, O(EtO)$_{1-3}$H, O(EtO)$_{1-3}$$(C_1-C_4)$alkyl, O$(C_6-C_{10})$aryl, O(CO)$(C_1-C_4)$alkyl, O(CO)$(C_1-C_4)$alkyl-NH$_2$, O(CO)$(C_6-C_{10})$aryl, OCF$_3$, OSO$_2$$(C_1-C_4)$alkyl, OSO$_2$OH, NH$(C_1-C_4)$alkyl, N[$(C_1-C_4)$alkyl][$(C_1-C_4)$alkyl], NH(CO)$(C_1-C_4)$alkyl, NH(CO)$(C_1-C_4)$alkyl-NH$_2$, NH(CO)$(C_6-C_{10})$aryl, NHSO$_2$$(C_1-C_4)$alkyl, SO$_2$NH$_2$, and CF$_3$; and
$R^5$ represents hydrogen or methyl.

In another aspect of the invention, there is provided a compound of formula I,
wherein
Y and D represent carbon;
Z, E and A represent nitrogen;
L represents a bond or $(C_1-C_2)$alkyl;
$R^1$ represents hydrogen;
$R^2$ represents hydrogen;
$R^3$ represents hydrogen or methyl;
$R^4$ represents a heteroaryl selected from indolyl, indazolyl, benzimidazolyl, and indolinonyl, said heteroaryl optionally substituted with one or two substituents selected from the group consisting of halogen, hydroxy, amino, nitro, cyano, $(C_1-C_4)$alkyl, $(C_1-C_4)$alkyl$(C_2-C_9)$heterocyclyl, $(C_1-C_4)$alkyl(CO)OH, $(C_1-C_4)$alkyl(CO)O$(C_1-C_4)$alkyl, $(C_1-C_4)$alkyl(CO)NH$_2$, $(C_1-C_4)$alkyl(CO)NH$(C_1-C_4)$alkyl, $(C_1-C_4)$alkyl(CO)NH$(C_1-C_4)$alkyl(CO)OH, $(C_1-C_4)$alkyl-OH, $(C_1-C_4)$alkyl-O$(C_1-C_4)$alkyl, $(C_1-C_4)$alkyl-O$(C_6-C_{10})$aryl, $(C_1-C_4)$alkyl-O(CO)$(C_1-C_4)$alkyl, $(C_1-C_4)$alkyl-O(CO)$(C_1-C_4)$alkyl-NH$_2$, $(C_1-C_4)$alkyl-O(CO)$(C_6-C_{10})$aryl, $(C_1-C_4)$alkyl-NH$_2$, $(C_1-C_4)$alkyl-NH$(C_1-C_4)$alkyl, $(C_1-C_4)$alkyl-N[$(C_1-C_4)$alkyl][$(C_1-C_4)$-alkyl], $(C_1-C_4)$alkyl-NH(CO)$(C_1-C_4)$alkyl, $(C_1-C_4)$alkyl-NH(CO)$(C_1-C_4)$alkyl-NH$_2$, $(C_1-C_4)$alkyl-NH(CO)$(C_6-C_{10})$aryl, $(C_1-C_4)$alkyl(CN), $(C_1-C_4)$alkyl$(C_6-C_{10})$aryl, (CO)OH, (CO)O$(C_1-C_4)$alkyl, (CO)NH$_2$, (CO)NH$(C_1-C_4)$alkyl, (CO)NH$(C_1-C_4)$alkyl(CO)OH, (CO)$(C_1-C_4)$alkyl, (CO)$(C_1-C_4)$alkyl$(C_6-C_{10})$aryl, (CO)$(C_1-C_4)$alkyl$(C_1-C_9)$heteroaryl, (CO)$(C_1-C_4)$alkyl$(C_2-C_9)$heterocyclyl, (CO)$(C_2-C_9)$heterocyclyl, (CO)$(C_6-C_{10})$aryl, (CO)$(C_1-C_9)$heteroaryl, $(C_6-C_{10})$aryl, $(C_6-C_{10})$aryl-halogen, $(C_6-C_{10})$aryl-OH, $(C_6-C_{10})$aryl-NH$_2$, $(C_6-C_{10})$aryl-O$(C_1-C_4)$alkyl, $(C_1-C_9)$heteroaryl, $(C_1-C_9)$heteroaryl-halogen, $(C_1-C_9)$heteroaryl-OH, $(C_1-C_9)$heteroaryl-NH$_2$, $(C_1-C_9)$heteroaryl$(C_1-C_4)$alkyl, $(C_1-C_9)$heteroaryl-O$(C_1-C_4)$alkyl, $(C_2-C_9)$heterocyclyl, $(C_2-C_9)$heterocyclyl$(C_1-C_4)$alkyl, $(C_2-C_9)$heterocyclyl$(C_1-C_4)$alkyl-OH, $(C_2-C_9)$heterocyclyl($C_1$-$C_4$)alkyl-$NH_2$, O($C_1$-$C_4$)alkyl, O($C_1$-$C_4$)alkyl($C_6$-$C_{10}$)aryl, O($C_1$-$C_4$)alkyl($C_6$-$C_{10}$)heteroaryl, O($C_1$-$C_4$)alkyl($C_2$-$C_9$)heterocyclyl, O($C_1$-$C_4$)alkyl($C_2$-$C_9$)heterocyclyl($C_1$-$C_4$)alkyl, O($C_1$-$C_4$)alkyl($C_2$-$C_9$)heterocyclyl($C_1$-$C_4$)alkyl-OH, O(EtO)$_{1-3}$H, O(EtO)$_{1-3}$($C_1$-$C_4$)alkyl, O($C_6$-$C_{10}$)aryl, O(CO)($C_1$-$C_4$)alkyl, O(CO)($C_1$-$C_4$)alkyl-$NH_2$, O(CO)($C_6$-$C_{10}$)aryl, $OCF_3$, $OSO_2$($C_1$-$C_4$)alkyl, $OSO_2$OH, NH($C_1$-$C_4$)alkyl, N[($C_1$-$C_4$)alkyl][($C_1$-$C_4$)alkyl], NH(CO)($C_1$-$C_4$)alkyl, NH(CO)($C_1$-$C_4$)alkyl-$NH_2$, NH(CO)($C_6$-$C_{10}$)aryl, $NHSO_2$($C_1$-$C_4$)alkyl, $SO_2NH_2$, and $CF_3$; and $R^5$ represents hydrogen or methyl.

In another aspect of the invention, there is provided a compound of formula I,
wherein
Z, D and E represent carbon;
Y and A represent nitrogen;
L represents a bond or ($C_1$-$C_2$)alkyl;
$R^1$ represents hydrogen or methyl;
$R^2$ represents hydrogen;
$R^3$ represents hydrogen or methyl;
$R^4$ represents a heteroaryl selected from indolyl, indazolyl, and benzimidazolyl, said heteroaryl optionally substituted with one or two substituents selected from the group consisting of hydroxy, methyl, and methoxy; and
$R^5$ represents hydrogen or methyl.

In another aspect of the invention, there is provided a compound of formula I,
wherein
Z and E represent carbon;
Y, D, and A represent nitrogen;
L represents a bond or ($C_1$-$C_2$)alkyl;
$R^2$ represents hydrogen;
$R^3$ represents hydrogen or methyl;
$R^4$ represents a heteroaryl selected from indolyl, indazolyl, and benzimidazolyl, said heteroaryl optionally substituted with one or two substituents selected from the group consisting of hydroxy, methyl, and methoxy; and
$R^5$ represents hydrogen or methyl.

In another aspect of the invention, there is provided a compound of formula I,
wherein
Z and D represent carbon;
Y, E and A represent nitrogen;
L represents a bond or ($C_1$-$C_2$)alkyl;
$R^1$ represents hydrogen;
$R^2$ represents hydrogen;
$R^3$ represents hydrogen or methyl;
$R^4$ represents a heteroaryl selected from indolyl, indazolyl, and benzimidazolyl, said heteroaryl optionally substituted with one or two substituents selected from the group consisting of hydroxy, methyl, and methoxy; and
$R^5$ represents hydrogen or methyl.

In another aspect of the invention, there is provided a compound of formula I,
wherein Z, A and D represent carbon;
Y and E represent nitrogen;
L represents a bond or ($C_1$-$C_2$)alkyl;
$R^1$ represents hydrogen or methyl;
$R^2$ represents hydrogen;
$R^3$ represents hydrogen or methyl;
$R^4$ represents a heteroaryl selected from indolyl, indazolyl, and benzimidazolyl, said heteroaryl optionally substituted with one or two substituents selected from the group consisting of hydroxy, methyl, and methoxy; and
$R^5$ represents hydrogen or methyl.

In another aspect of the invention, there is provided a compound of formula I,
wherein
Y, D and E represent carbon;
Z and A represent nitrogen;
L represents a bond or ($C_1$-$C_2$)alkyl;
$R^1$ represents hydrogen or methyl;
$R^2$ represents hydrogen;
$R^3$ represents hydrogen or methyl;
$R^4$ represents a heteroaryl selected from indolyl, indazolyl, and benzimidazolyl, said heteroaryl optionally substituted with one or two substituents selected from the group consisting of hydroxy, methyl, and methoxy; and
$R^5$ represents hydrogen or methyl.

In another aspect of the invention, there is provided a compound of formula I,
wherein
Y and E represent carbon;
Z, D, and A represent nitrogen;
L represents a bond or ($C_1$-$C_2$)alkyl;
$R^2$ represents hydrogen;
$R^3$ represents hydrogen or methyl;
$R^4$ represents a heteroaryl selected from indolyl, indazolyl, and benzimidazolyl, said heteroaryl optionally substituted with one or two substituents selected from the group consisting of hydroxy, methyl, and methoxy; and
$R^5$ represents hydrogen or methyl.

In another aspect of the invention, there is provided a compound of formula I,
wherein
Y and D represent carbon;
Z, E and A represent nitrogen;
L represents a bond or ($C_1$-$C_2$)alkyl;
$R^1$ represents hydrogen;
$R^2$ represents hydrogen;
$R^3$ represents hydrogen or methyl;
$R^4$ represents a heteroaryl selected from indolyl, indazolyl, and benzimidazolyl, said heteroaryl optionally substituted with one or two substituents selected from the group consisting of hydroxy, methyl, and methoxy; and
$R^5$ represents hydrogen or methyl.

In another aspect of the invention, there is provided a compound of formula I,
wherein
Y, A and D represent carbon;
Z and E represent nitrogen;
L represents a bond or ($C_1$-$C_2$)alkyl;
$R^1$ represents hydrogen;
$R^2$ represents hydrogen;
$R^3$ represents hydrogen or methyl;
$R^4$ represents a heteroaryl selected from indolyl, indazolyl, and benzimidazolyl, said heteroaryl optionally substituted with one or two substituents selected from the group consisting of hydroxy, methyl, and methoxy; and
$R^5$ represents hydrogen or methyl.

In another aspect of the invention, there is provided a compound of formula I,
wherein
Z, D and E represent carbon;
Y and A represent nitrogen;
$R^1$ represents hydrogen or methyl;
$R^2$ represents hydrogen;
$R^3$ represents hydrogen or methyl;

L-R⁴ is selected from:

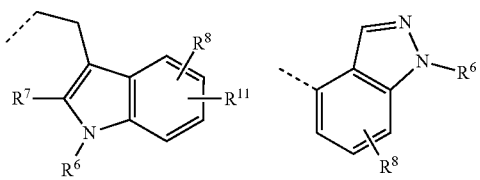

R⁷ represents hydrogen or methyl;
R⁶ represents hydrogen or methyl;
R⁸ is selected from hydrogen, methyl, fluoro, methoxy, ethoxy and $OCF_3$;
R¹¹ is selected from hydrogen, methyl, and methoxy; and
R⁵ represents hydrogen or methyl.

In another aspect of the invention, there is provided a compound of formula I,
wherein
Y, D and E represent carbon;
Z and A represent nitrogen;
R¹, R², and R³ represent hydrogen;
L-R⁴ is selected from:

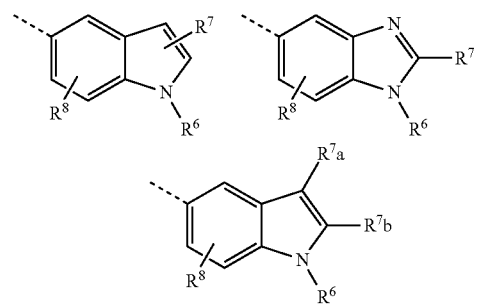

R⁶ represents hydrogen or methyl;
R⁸ represents hydrogen;
R⁷ is selected from hydrogen, methyl, $(C_1-C_4)$alkyl-OH, and $COOCH_3$;
$R^{7a}$ and $R^{7b}$ is independently selected from hydrogen and methyl; and
R⁵ represents hydrogen or methyl.

In another aspect of the invention, there is provided a compound of formula I,
wherein
Z represents carbon or nitrogen;
Y represents carbon or nitrogen, wherein one of Z and Y represents nitrogen;
A, D and E is selected from carbon and nitrogen, wherein A represents nitrogen and
D and E represents carbon; or A and D represent nitrogen and E represents carbon; or
A and E represent nitrogen and D represents carbon; or E represents nitrogen and A and D represent carbon;
R¹ represents hydrogen or methyl, when D represents carbon;
R² represents hydrogen or amino;
R³ represents hydrogen, methyl, trifluoromethyl or $(C_0-C_1)$ alkylaryl;
R⁵ represents hydrogen or methyl;

L-R⁴ is selected from:

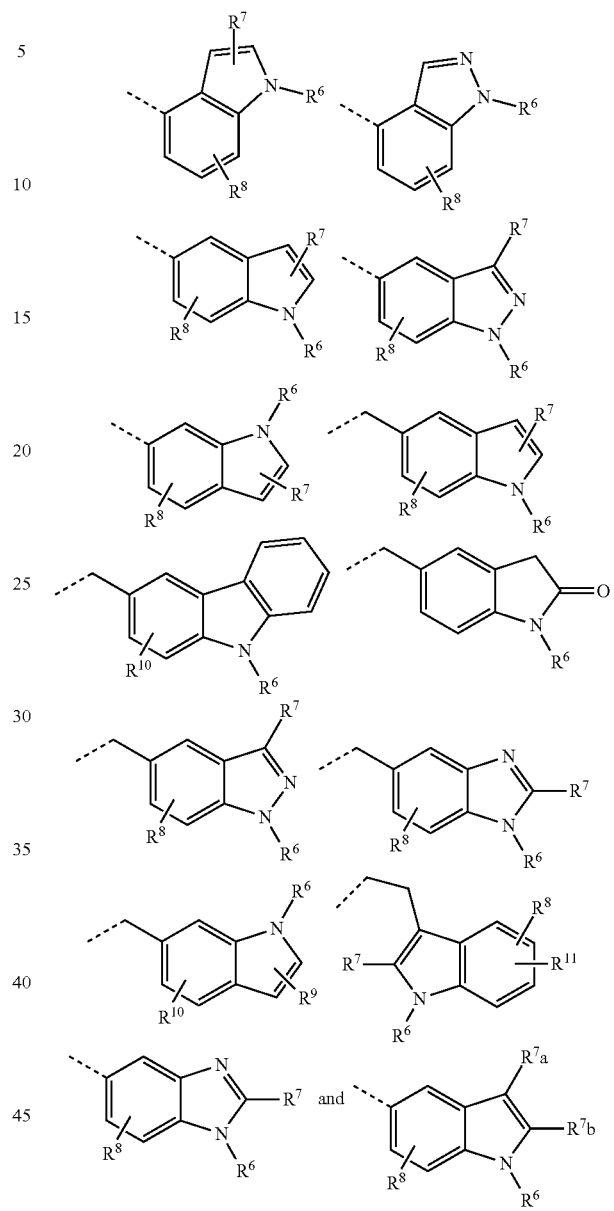

R⁶ is selected from hydrogen and methyl;
R⁷ is selected from hydrogen, methyl, $(C_1-C_4)$alkyl-OH and $(CO)OCH_3$;
$R^{7a}$ and $R^{7b}$ are independently selected from hydrogen, and methyl;
R⁸ is selected from halogen, hydrogen, hydroxy, (CO)OH, $(CO)OCH_3$, $O(C_1-C_4)$alkyl, $O(C_1-C_4)$alkyl$(C_6-C_{10})$aryl, $O(C_1-C_4)$alkyl$(C_2-C_9)$heterocyclyl, $O(EtO)_{1-3}(C_1-C_4)$ alkyl, and $OCF_3$;
R⁹ and R¹⁰ represent hydrogen; and
R¹¹ is selected from hydrogen, methyl, and $O(C_1-C_4)$alkyl.

In another aspect of the invention, there is provided a compound of formula I,
wherein Z represents carbon or nitrogen;
Y represents carbon or nitrogen, wherein one of Z and Y represents nitrogen;
A, D and E is selected from carbon and nitrogen, wherein A represents nitrogen and D and E represents carbon; or A and D represent nitrogen and E represents carbon; or A and E represent nitrogen and D represents carbon; or E represents nitrogen and A and D represent carbon;

$R^1$ represents hydrogen or methyl, when D represents carbon;
$R^2$ represents hydrogen or amino;
$R^3$ represents hydrogen, methyl, trifluoromethyl or $(C_0-C_1)$ alkylaryl;
$R^5$ represents hydrogen or methyl;
$L-R^4$ is selected from:

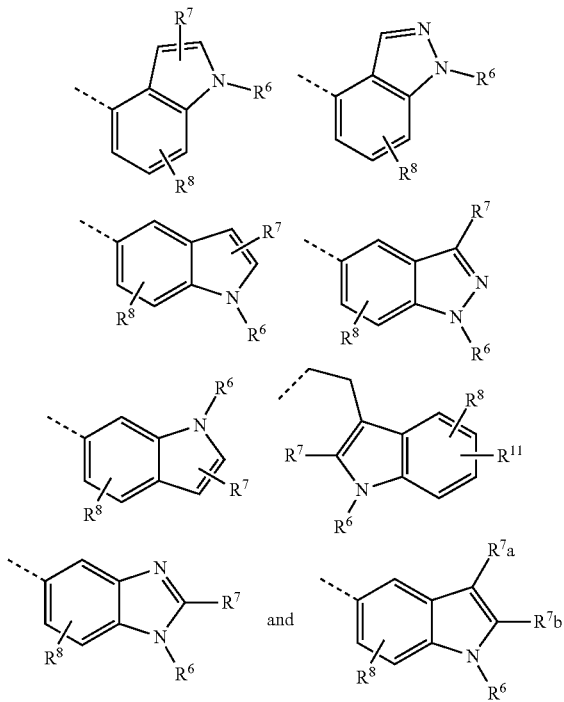

$R^6$ is selected from hydrogen and methyl;
$R^7$ is selected from hydrogen, methyl, $(C_1-C_4)$alkyl-OH, and $(CO)OCH_3$,
$R^{7a}$ and $R^{7b}$ are independently selected from hydrogen, and methyl;
$R^8$ is selected from halogen, hydrogen, hydroxy, (CO)OH, $(CO)OCH_3$, $O(C_1-C_4)$alkyl, $O(C_1-C_4)$alkyl$(C_6-C_{10})$aryl, $O(C_1-C_4)$alkyl$(C_2-C_9)$heterocyclyl, $0(EtO)_{1-3}(C_1-C_4)$ alkyl, and $OCF_3$; and
$R^{11}$ is selected from hydrogen, methyl, and $O(C_1-C_4)$alkyl.

In another aspect of the invention, there is provided a compound of formula I,
wherein L represents a bond or $(C_2)$alkyl.

In another aspect of the invention, there is provided a compound of formula I, said compound being selected from:
$N^4$-(1H-indol-5-ylmethyl)-$N^2$-(1H-indol-4-yl)pyrimidine-2,4-diamine;
$N^4$-(1H-indol-5-ylmethyl)-$N^2$-(1H-indol-5-yl)pyrimidine-2,4-diamine;
$N^4$-(1H-indol-5-ylmethyl)-$N^2$-(2-methyl-1H-indol-5-yl)pyrimidine-2,4-diamine;
$N^4$-(1H-indol-5-ylmethyl)-$N^2$-(1H-indazol-5-yl)pyrimidine-2,4-diamine;
$N^4$-(1H-indol-5-ylmethyl)-$N^2$-(2-methyl-1H-indol-5-ylmethyl)pyrimidine-2,4-diamine;
$N^2$-(1H-indazol-5-ylmethyl)-$N^4$-(1H-indol-5-ylmethyl)pyrimidine-2,4-diamine;
$N^2$-(1H-benzo[c/]imidazol-5-ylmethyl)-$N^4$-(1H-indol-5-ylmethyl)pyrimidine-2,4-diamine;
$N^4$-(1H-indol-5-ylmethyl)-$N^2$-(1H-indol-6-ylmethyl)pyrimidine-2,4-diamine;
$N^2$-[2-(1H-indol-3-yl)ethyl]-$N^4$-(1H-indol-5-ylmethyl)pyrimidine-2,4-diamine;
3-{2-[4-(1H-indol-5-ylmethylamino)-pyrimidin-2-ylamino]ethyl}-1H-indol-5-ol;
$N^4$-(1H-indol-5-ylmethyl)-$N^2$-[2-(5-methyl-1H-indol-3-yl)ethyl]pyrimidine-2,4-diamine;
$N^4$-(1H-indol-5-ylmethyl)-$N^2$-[2-(5-methoxy-1H-indol-3-yl)ethyl]pyrimidine-2,4-diamine;
$N^2$-(1H-indol-4-yl)-$N^4$-(2-methyl-1H-indol-5-ylmethyl)pyrimidine-2,4-diamine;
$N^2$-(1H-indol-5-ylmethyl)-$N^4$-(2-methyl-1H-indol-5-ylmethyl)pyrimidine-2,4-diamine;
$N^2,N^4$-Bis-(2-methyl-1H-indol-5-ylmethyl)pyrimidine-2,4-diamine;
$N^2$-(1H-indazol-5-ylmethyl)-$N^4$-(2-methyl-1H-indol-5-ylmethyl)pyrimidine-2,4-diamine;
$N^2$-(2-(1H-indol-3-yl)-ethyl)-$N^4$-(2-methyl-1H-indol-5-ylmethyl)pyrimidine-2,4-diamine;
$N^2$-(1H-indol-4-yl)-$N^4$-(1H-indazol-5-ylmethyl)pyrimidine-2,4-diamine;
$N^4$-(1H-benzo[c/]imidazol-5-ylmethyl)-$N^2$-(1H-indol-4-yl)pyrimidine-2,4-diamine;
$N^4$-(1H-indol-6-ylmethyl)-$N^2$-(1H-indol-4-yl)pyrimidine-2,4-diamine;
$N^2$-(1H-indol-5-ylmethyl)-$N^4$-(1H-indol-6-ylmethyl)pyrimidine-2,4-diamine;
$N^2,N^4$-bis-(1H-indol-6-ylmethyl)pyrimidine-2,4-diamine;
$N^2$-(1H-indol-5-ylmethyl)-$N^4$-(1H-indol-4-yl)pyrimidine-2,4-diamine;
$N^2$-(1H-indol-5-ylmethyl)-$N^4$-(2-methyl-1H-indol-5-yl)pyrimidine-2,4-diamine;
$N^4$-[2-(1H-indol-3-yl)ethyl]-$N^2$-(1H-indol-5-ylmethyl)pyrimidine-2,4-diamine;
3-{2-[2-(1H-indol-5-ylmethylamino)-pyrimidin-4-ylamino]ethyl}-1H-indol-5-ol;
$N^2$-(1H-indol-5-ylmethyl)-$N^4$-[2-(5-methyl-1H-indol-3-yl)ethyl]pyrimidine-2,4-diamine;
$N^2$-(1H-indol-5-ylmethyl)-$N^4$-[2-(5-methoxy-1H-indol-3-yl)ethyl]pyrimidine-2,4-diamine;
$N^2$-(1H-indazol-5-ylmethyl)-$N^4$-(1H-indol-4-yl)pyrimidine-2,4-diamine;
$N^2$-(1H-indol-4-yl)-$N^4$-(1H-indol-5-ylmethyl)-6-methylpyrimidine-2,4-diamine;
$N^2,N^4$-bis(1H-indol-5-ylmethyl)-6-methylpyrimidine-2,4-diamine;
3-{2-[4-(1H-indol-5-ylmethylamino)-6-methyl-pyrimidin-2-ylamino]-ethyl}-1H-indol-5-ol;
$N^4$-(1H-indol-5-ylmethyl)-$N^2$-(2-methyl-1H-indol-5-yl)-6-trifluoromethylpyrimidine-2,4-diamine;
$N^2,N^4$-bis-(1H-indol-5-ylmethyl)-6-trifluoromethylpyrimidine-2,4-diamine;
$N^2$-(2-(1H-indol-3-yl)ethyl)-$N^4$-(1H-indol-5-ylmethyl)-6-trifluoromethylpyrimidine-2,4-diamine;
$N^2,N^4$-bis(1H-indol-5-ylmethyl)-6-benzylpyrimidine-2,4-diamine;
$N^4$-(1H-indazol-5-ylmethyl)-$N^2$-(1H-indol-4-yl)-6-methylpyrimidine-2,4-diamine;
$N^4$-(1H-indol-5-ylmethyl)-$N^2$-(1H-indol-4-yl)pyrimidine-2,4,5-triamine;
$N^4$-(1H-indol-5-ylmethyl)-$N^2$-(1H-indol-5-yl)pyrimidine-2,4,5-triamine;
$N^4$-(1H-indol-5-ylmethyl)-$N^2$-(1H-indol-6-yl)pyrimidine-2,4,5-triamine; and
$N^2,N^4$-bis(1H-indol-5-ylmethyl)pyrimidine-2,4,5-triamine.

In another aspect of the invention, there is provided a compound of formula I, said compound being selected from:

5-{[2-(1H-indol-5-ylmethylamino)pyrimidin-4-ylamino]methyl}indolin-2-one;
$N^4$-(2-methyl-1H-indol-5-yl)-$N^2$-(2-methyl-1H-indol-5-ylmethyl)pyrimidine-2,4-diamine;
$N^2$-[2-(5-methoxy-1H-indol-3-yl)ethyl]-$N^4$-(2-methyl-1H-indol-5-ylmethyl)pyrimidine-2,4-diamine;
$N^2$-(1H-indazol-5-ylmethyl)-$N^4$-(2-methyl-1H-indol-5-yl)pyrimidine-2,4-diamine;
$N^4$-(1H-indazol-5-ylmethyl)-$N^2$-[2-(5-methoxy-1H-indol-3-yl)ethyl]pyrimidine-2,4-diamine;
$N^2$-(1H-benzo[d]imidazol-5-ylmethyl)-$N^4$-(2-methyl-1H-indol-5-yl)pyrimidine-2,4-diamine;
$N^4$-(1H-benzo[d]imidazol-5-ylmethyl)-$N^2$-(1H-indol-5-ylmethyl)pyrimidine-2,4-diamine;
$N^4$-(1H-benzo[d]imidazol-5-ylmethyl)-$N^2$-[2-(5-methoxy-1H-indol-3-yl)ethyl]pyrimidine-2,4-diamine;
$N^2$-(1H-indol-6-ylmethyl)-$N^4$-(2-methyl-1H-indol-5-yl)pyrimidine-2,4-diamine;
$N^4$-(1H-indol-6-ylmethyl)-$N^2$-[2-(5-methoxy-1H-indol-3-yl)ethyl]pyrimidine-2,4-diamine;
$N^4$-(1H-indol-5-ylmethyl)-$N^2$-{2-[5-(benzyloxy)-1H-indol-3-yl]ethyl}pyrimidine-2,4-diamine;
$N^4$-(1H-indol-5-ylmethyl)-$N^2$-{2-[5-(2-morpholinoethoxy)-1H-indol-3-yl]ethyl}pyrimidine-2,4-diamine;
$N^4$-(1H-indol-5-ylmethyl)-$N^2$-{2-[5-(2-methoxyethoxy)-1H-indol-3-yl]ethyl}pyrimidine-2,4-diamine;
$N^4$-(1H-indol-5-ylmethyl)-$N^2$-(1-methyl-1H-indol-4-yl)pyrimidine-2,4-diamine;
$N^4$-(1H-indol-5-ylmethyl)-$N^2$-(1H-indazol-4-yl)pyrimidine-2,4-diamine;
$N^4$-(1H-indol-5-ylmethyl)-$N^2$-[(1-methyl-1H-indol-5-yl)methyl]pyrimidine-2,4-diamine;
$N^4$-(1H-indol-5-ylmethyl)-$N^2$-(1H-indol-4-ylmethyl)pyrimidine-2,4-diamine;
$N^4$-(1H-indol-5-ylmethyl)-$N^2$-[(9H-carbazol-3-yl)methyl]pyrimidine-2,4-diamine;
$N^2$-(1H-indol-5-ylmethyl)-$N^4$-[(9H-carbazol-3-yl)methyl]pyrimidine-2,4-diamine;
Methyl 4-[4-(1H-indol-5-ylmethylamino)pyrimidin-2-ylamino]-1H-indole-6-carboxylate;
$N^2$-(1H-indol-5-ylmethyl)-$N^4$-(1H-indol-5-yl)pyrimidine-2,4-diamine;
$N^2$-(1H-indol-5-ylmethyl)-6-methyl-$N^4$-(2-methyl-1H-indol-5-yl)pyrimidine-2,4-diamine;
$N^4$-(1H-indol-5-ylmethyl)-$N^2$-[2-(5-methoxy-1H-indol-3-yl)ethyl]-6-methylpyrimidine-2,4-diamine; and
$N^4$-(1H-indol-5-ylmethyl)-6-benzyl-$N^2$-[2-(5-methoxy-1H-indol-3-yl)ethyl]pyrimidine-2,4-diamine.

In another aspect of the invention, there is provided a compound of formula I, said compound being selected from:

$N^4$-(1H-indol-5-ylmethyl)-$N^2$-[2-(5-methoxy-7-methyl-1H-indol-3-yl)ethyl]pyrimidine-2,4-diamine;
$N^4$-(1H-indol-5-ylmethyl)-$N^2$-[2-(5-ethoxy-1H-indol-3-yl)ethyl]pyrimidine-2,4-diamine;
$N^4$-(1H-indol-5-ylmethyl)-$N^2$-{2-[5-(trifluoromethoxy)-1H-indol-3-yl]ethyl}pyrimidine-2,4-diamine;
$N^4$-(1H-indol-5-ylmethyl)-$N^2$-[2-(5-fluoro-1H-indol-3-yl)ethyl]pyrimidine-2,4-diamine;
$N^4$-(1H-indol-5-ylmethyl)-$N^2$-[2-(6-methoxy-1H-indol-3-yl)ethyl]pyrimidine-2,4-diamine;
$N^4$-(1H-indol-5-ylmethyl)-$N^2$-[2-(7-methoxy-1H-indol-3-yl)ethyl]pyrimidine-2,4-diamine;
$N^2$-(1H-indol-5-ylmethyl)-$N^4$-(1,2-dimethyl-1H-indol-5-yl)pyrimidine-2,4-diamine;
methyl 5-[2-(1H-indol-5-ylmethylamino)pyrimidin-4-ylamino]-1H-indole-2-carboxylate;
$N^2$-(1H-indol-5-ylmethyl)-$N^4$-(2,3-dimethyl-1H-indol-5-yl)pyrimidine-2,4-diamine;
$N^2$-(1H-indol-5-ylmethyl)-$N^4$-(1H-benzo[c]imidazol-5-yl)pyrimidine-2,4-diamine;
$N^2$-(1H-indol-5-ylmethyl)-$N^4$-(2-methyl-1H-benzo[c]imidazol-5-yl)pyrimidine-2,4-diamine;
$N^4$-(1H-indol-5-ylmethyl)-$N^2$-(1H-indazol-4-yl)-6-methylpyrimidine-2,4-diamine;
$N^2$-[2-(5-methoxy-1H-indol-3-yl)ethyl]-6-methyl-$N^4$-[(2-methyl-1H-indol-5-yl)methyl]pyrimidine-2,4-diamine;
$N^4$-(1H-indazol-5-ylmethyl)-$N^2$-[2-(5-methoxy-1H-indol-3-yl)ethyl]-6-methylpyrimidine-2,4-diamine;
$N^4$-(1H-indol-5-ylmethyl)-$N^2$-[2-(5-methoxy-2-methyl-1H-indol-3-yl)ethyl]-6-methylpyrimidine-2,4-diamine;
$N^4$-(1H-indol-5-ylmethyl)-$N^2$-[2-(4-methoxy-1H-indol-3-yl)ethyl]pyrimidine-2,4-diamine;
4-[4-(1H-indol-5-ylmethylamino)pyrimidin-2-ylamino]-1H-indole-6-carboxylic acid;
$N^2$-(1H-indol-4-yl)-6-methyl-$N^4$-[(2-methyl-1H-indol-5-yl)methyl]pyrimidine-2,4-diamine;
{5-[2-(1H-indol-5-ylmethylamino)pyrimidin-4-ylamino]-1H-indol-2-yl}methano 1;
$N^2$-(1H-indol-5-ylmethyl)-$N^4$-methyl-$N^4$-(2-methyl-1H-indol-5-yl)pyrimidine-2,4-diamine;
$N^2$-(1H-indol-5-ylmethyl)-$N^4$-(1,2-dimethyl-1H-indol-5-yl)-$N^4$-methylpyrimidine-2,4-diamine;
$N^4$-(1H-indol-5-ylmethyl)-$N^2$-[2-(5-methoxy-1-methyl-1H-indol-3-yl)ethyl]pyrimidine-2,4-diamine;
$N^4$-(1H-indol-5-ylmethyl)-$N^2$-[2-(5-methoxy-1-methyl-1H-indol-3-yl)ethyl]-$N^2$-methylpyrimidine-2,4-diamine; and
$N^4$-(1H-indol-5-ylmethyl)-$N^2$-[2-(5-methoxy-1H-indol-3-yl)ethyl]-$N^2$-methylpyrimidine-2,4-diamine.

In preferred aspect of the invention, there is provided a compound of formula I, said compound being selected from:

$N^4$-(1H-indol-5-ylmethyl)-$N^2$-(1H-indol-4-yl)pyrimidine-2,4-diamine;
$N^4$-(1H-indol-5-ylmethyl)-$N^2$-(1H-indol-5-yl)pyrimidine-2,4-diamine;
$N^4$-(1H-indol-5-ylmethyl)-$N^2$-(2-methyl-1H-indol-5-yl)pyrimidine-2,4-diamine;
$N^4$-(1H-indol-5-ylmethyl)-$N^2$-(1H-indazol-5-yl)pyrimidine-2,4-diamine;
$N^2$-[2-(1H-indol-3-yl)ethyl]-$N^4$-(1H-indol-5-ylmethyl)pyrimidine-2,4-diamine;
3-{2-[4-(1H-indol-5-ylmethylamino)-pyrimidin-2-ylamino]ethyl}-1H-indol-5-ol;
$N^4$-(1H-indol-5-ylmethyl)-$N^2$-[2-(5-methyl-1H-indol-3-yl)ethyl]pyrimidine-2,4-diamine;
$N^4$-(1H-indol-5-ylmethyl)-$N^2$-[2-(5-methoxy-1H-indol-3-yl)ethyl]pyrimidine-2,4-diamine;
$N^2$-(1H-indol-4-yl)-$N^4$-(2-methyl-1H-indol-5-ylmethyl)pyrimidine-2,4-diamine;
$N^2$-(2-(1H-indol-3-yl)-ethyl)-$N^4$-(2-methyl-1H-indol-5-ylmethyl)pyrimidine-2,4-diamine;
$N^2$-(1H-indol-4-yl)-$N^4$-(1H-indazol-5-ylmethyl)pyrimidine-2,4-diamine;
$N^4$-(1H-benzo[c]imidazol-5-ylmethyl)-$N^2$-(1H-indol-4-yl)pyrimidine-2,4-diamine;
$N^4$-(1H-indol-6-ylmethyl)-$N^2$-(1H-indol-4-yl)pyrimidine-2,4-diamine;
$N^2$-(1H-indol-5-ylmethyl)-$N^4$-(1H-indol-4-yl)pyrimidine-2,4-diamine;
$N^2$-(1H-indol-5-ylmethyl)-$N^4$-(2-methyl-1H-indol-5-yl)pyrimidine-2,4-diamine;

N⁴-[2-(1H-indol-3-yl)ethyl]-N²-(1H-indol-5-ylmethyl)pyrimidine-2,4-diamine;
3-{2-[2-(1H-indol-5-ylmethylamino)-pyrimidin-4-ylamino]ethyl}-1H-indol-5-ol;
N²-(1H-indol-5-ylmethyl)-N⁴-[2-(5-methyl-1H-indol-3-yl)ethyl]pyrimidine-2,4-diamine;
N²-(1H-indol-5-ylmethyl)-N⁴-[2-(5-methoxy-1H-indol-3-yl)ethyl]pyrimidine-2,4-diamine;
N²-(1H-indazol-5-ylmethyl)-N⁴-(1H-indol-4-yl)pyrimidine-2,4-diamine;
N²-(1H-indol-4-yl)-N⁴-(1H-indol-5-ylmethyl)-6-methylpyrimidine-2,4-diamine;
3-{2-[4-(1H-indol-5-ylmethylamino)-6-methyl-pyrimidin-2-ylamino]-ethyl}-1H-indol-5-ol;
N⁴-(1H-indol-5-ylmethyl)-N²-(2-methyl-1H-indol-5-yl)-6-trifluoromethylpyrimidine-2,4-diamine;
N²-(2-(1H-indol-3-yl)ethyl)-N⁴-(1H-indol-5-ylmethyl)-6-trifluoromethylpyrimidine-2,4-diamine;
N⁴-(1H-indazol-5-ylmethyl)-N²-(1H-indol-4-yl)-6-methylpyrimidine-2,4-diamine;
N⁴-(1H-indol-5-ylmethyl)-N²-(1H-indol-4-yl)pyrimidine-2,4,5-triamine;
N⁴-(1H-indol-5-ylmethyl)-N²-(1H-indol-5-yl)pyrimidine-2,4,5-triamine;
N⁴-(1H-indol-5-ylmethyl)-N²-(1H-indol-6-yl)pyrimidine-2,4,5-triamine;
N⁴-(2-methyl-1H-indol-5-yl)-N²-(2-methyl-1H-indol-5-ylmethyl)pyrimidine-2,4-diamine;
N²-[2-(5-methoxy-1H-indol-3-yl)ethyl]-N⁴-(2-methyl-1H-indol-5-ylmethyl)pyrimidine-2,4-diamine;
N²-(1H-indazol-5-ylmethyl)-N⁴-(2-methyl-1H-indol-5-yl)pyrimidine-2,4-diamine;
N⁴-(1H-indazol-5-ylmethyl)-N²-[2-(5-methoxy-1H-indol-3-yl)ethyl]pyrimidine-2,4-diamine;
N²-(1H-benzo[d]imidazol-5-ylmethyl)-N⁴-(2-methyl-1H-indol-5-yl)pyrimidine-2,4-diamine;
N⁴-(1H-benzo[d]imidazol-5-ylmethyl)-N²-[2-(5-methoxy-1H-indol-3-yl)ethyl]pyrimidine-2,4-diamine;
N²-(1H-indol-6-ylmethyl)-N⁴-(2-methyl-1H-indol-5-yl)pyrimidine-2,4-diamine;
N⁴-(1H-indol-6-ylmethyl)-N²-[2-(5-methoxy-1H-indol-3-yl)ethyl]pyrimidine-2,4-diamine;
N⁴-(1H-indol-5-ylmethyl)-N²-{2-[5-(benzyloxy)-1H-indol-3-yl]ethyl}pyrimidine-2,4-diamine;
N⁴-(1H-indol-5-ylmethyl)-N²-{2-[5-(2-morpholinoethoxy)-1H-indol-3-yl]ethyl}pyrimidine-2,4-diamine;
N⁴-(1H-indol-5-ylmethyl)-N²-{2-[5-(2-methoxyethoxy)-1H-indol-3-yl]ethyl}pyrimidine-2,4-diamine;
N⁴-(1H-indol-5-ylmethyl)-N²-(1-methyl-1H-indol-4-yl)pyrimidine-2,4-diamine;
N⁴-(1H-indol-5-ylmethyl)-N²-(1H-indazol-4-yl)pyrimidine-2,4-diamine;
Methyl 4-[4-(1H-indol-5-ylmethylamino)pyrimidin-2-ylamino]-1H-indole-6-carboxylate;
N²-(1H-indol-5-ylmethyl)-N⁴-(1H-indol-5-yl)pyrimidine-2,4-diamine;
N²-(1H-indol-5-ylmethyl)-6-methyl-N⁴-(2-methyl-1H-indol-5-yl)pyrimidine-2,4-diamine;
N⁴-(1H-indol-5-ylmethyl)-N²-[2-(5-methoxy-1H-indol-3-yl]ethyl]-6-methylpyrimidine-2,4-diamine;
N⁴-(1H-indol-5-ylmethyl)-6-benzyl-N²-[2-(5-methoxy-1H-indol-3-yl)ethyl]pyrimidine-2,4-diamine;
N⁴-(1H-indol-5-ylmethyl)-N²-[2-(5-methoxy-7-methyl-1H-indol-3-yl)ethyl]pyrimidine-2,4-diamine;
N⁴-(1H-indol-5-ylmethyl)-N²-[2-(5-ethoxy-1H-indol-3-yl)ethyl]pyrimidine-2,4-diamine;
N⁴-(1H-indol-5-ylmethyl)-N²-{2-[5-(trifluoromethoxy)-1H-indol-3-yl]ethyl}pyrimidine-2,4-diamine;
N⁴-(1H-indol-5-ylmethyl)-N²-[2-(5-fluoro-1H-indol-3-yl)ethyl]pyrimidine-2,4-diamine;
N⁴-(1H-indol-5-ylmethyl)-N²-[2-(6-methoxy-1H-indol-3-yl)ethyl]pyrimidine-2,4-diamine;
N⁴-(1H-indol-5-ylmethyl)-N²-[2-(7-methoxy-1H-indol-3-yl)ethyl]pyrimidine-2,4-diamine;
N²-(1H-indol-5-ylmethyl)-N⁴-(1,2-dimethyl-1H-indol-5-yl)pyrimidine-2,4-diamine;
methyl 5-[2-(1H-indol-5-ylmethylamino)pyrimidin-4-ylamino]-1H-indole-2-carboxylate;
N²-(1H-indol-5-ylmethyl)-N⁴-(2,3-dimethyl-1H-indol-5-yl)pyrimidine-2,4-diamine;
N²-(1H-indol-5-ylmethyl)-N⁴-(1H-benzo[d]imidazol-5-yl)pyrimidine-2,4-diamine;
N²-(1H-indol-5-ylmethyl)-N⁴-(2-methyl-1H-benzo[d]imidazol-5-yl)pyrimidine-2,4-diamine;
N⁴-(1H-indol-5-ylmethyl)-N²-(1H-indazol-4-yl)-6-methylpyrimidine-2,4-diamine;
N²-[2-(5-methoxy-1H-indol-3-yl)ethyl]-6-methyl-N⁴-[(2-methyl-1H-indol-5-yl)methyl]pyrimidine-2,4-diamine;
N⁴-(1H-indazol-5-ylmethyl)-N²-[2-(5-methoxy-1H-indol-3-yl)ethyl]-6-methylpyrimidine-2,4-diamine;
N⁴-(1H-indol-5-ylmethyl)-N²-[2-(5-methoxy-2-methyl-1H-indol-3-yl)ethyl]-6-methylpyrimidine-2,4-diamine;
N⁴-(1H-indol-5-ylmethyl)-N²-[2-(4-methoxy-1H-indol-3-yl)ethyl]pyrimidine-2,4-diamine;
4-[4-(1H-indol-5-ylmethylamino)pyrimidin-2-ylamino]-1H-indole-6-carboxylic acid;
N²-(1H-indol-4-yl)-6-methyl-N⁴-[(2-methyl-1H-indol-5-yl)methyl]pyrimidine-2,4-diamine;
{5-[2-(1H-indol-5-ylmethylamino)pyrimidin-4-ylamino]-1H-indol-2-yl}methanol;
N²-(1H-indol-5-ylmethyl)-N⁴-methyl-N⁴-(2-methyl-1H-indol-5-yl)pyrimidine-2,4-diamine;
N²-(1H-indol-5-ylmethyl)-N⁴-(1,2-dimethyl-1H-indol-5-yl)-N⁴-methylpyrimidine-2,4-diamine;
N⁴-(1H-indol-5-ylmethyl)-N²-[2-(5-methoxy-1-methyl-1H-indol-3-yl)ethyl]pyrimidine-2,4-diamine;
N⁴-(1H-indol-5-ylmethyl)-N²-[2-(5-methoxy-1-methyl-1H-indol-3-yl)ethyl]-N²-methylpyrimidine-2,4-diamine; and
N⁴-(1H-indol-5-ylmethyl)-N²-[2-(5-methoxy-1H-indol-3-yl)ethyl]-N²-methylpyrimidine-2,4-diamine.

In another aspect of the invention, there is provided a compound of formula I, for use in therapy.

In another aspect of the invention, there is provided a compound of formula I, for use in treatment of cancer.

In another aspect of the invention, there is provided use of a compound of formula I, in the manufacture of a medicament and pharmaceutical compositions for treatment of cancer.

In another aspect of the invention, there is provided a pharmaceutical composition comprising a compound of formula I, together with pharmaceutically acceptable diluents and carriers.

In another aspect of the invention, there is provided a method for treatment of cancer, which comprises administering to a subject in need thereof, a therapeutically effective amount of a compound of formula I.

In another aspect of the invention, there is provided a method for treatment of cancer, which comprises administering to a subject in need thereof, a therapeutically effective amount of a compound of formula I, in combination with another compound of formula I, in combination with radiation therapy, or in combination with another anticancer agent selected from alkylating agents, antimetabolites, anticancer camptothecin derivatives, plan-derived anticancer agents, antibiotics, enzymes, platinum coordination complexes, tyrosine kinase inhibitors, hormones, hormone antagonists, monoclonal antibodies, interferons, and biological response modifiers.

In all lists and in the Examples, the compound names were generated in accordance with IUPAC by ChemBioDraw Ultra version 11.0.

In another aspect of the invention, there is provided a number of intermediate compounds, comprising the following:

N-(1H-indol-5-ylmethyl)-2-chloro-pyrimidin-4-amine;
N-(1H-indol-5-ylmethyl)-4-chloro-pyrimidin-2-amine;
N-(2-methyl-1H-indol-5-ylmethyl)-2-chloro-pyrimidin-4-amine;
N-(1H-indazol-5-ylmethyl)-2-chloro-pyrimidin-4-amine;
N-(1H-benzo[c/]imidazol-5-ylmethyl)-2-chloro-pyrimidin-4-amine;
N-(1H-indol-6-ylmethyl)-2-chloro-pyrimidin-4-amine;
N-(1H-indol-6-ylmethyl)-4-chloro-pyrimidin-2-amine;
N-(1H-indol-5-ylmethyl)-2-chloro-6-methyl-pyrimidin-4-amine;
N-(1H-indol-5-ylmethyl)-4-chloro-6-methyl-pyrimidin-2-amine;
N-(1H-indazol-5-ylmethyl)-2-chloro-6-methyl-pyrimidin-4-amine;
N-(1H-indol-5-ylmethyl)-2-chloro-6-trifluoromethyl-pyrimidin-4-amine;
N-(1H-indol-5-ylmethyl)-6-benzyl-2-chloro-pyrimidin-4-amine;
N-(1H-indol-5-ylmethyl)-2-chloro-5-nitro-pyrimidin-4-amine;
N-(1H-indol-4-yl)-2-chloro-pyrimidin-4-amine;
N-[2-(1H-indol-3-yl)ethyl]-2-chloro-pyrimidin-4-amine;
$N^4$-(1H-indol-5-ylmethyl)-$N^2$-(1H-indol-4-yl)-5-nitropyrimidine-2,4-diamine;
$N^4$-(1H-indol-5-ylmethyl)-$N^2$-(1H-indol-5-yl)-5-nitropyrimidine-2,4-diamine;
$N^4$-(1H-indol-5-ylmethyl)-$N^2$-(1H-indol-6-yl)-5-nitropyrimidine-2,4-diamine;
$N^2,N^4$-bis(1H-indol-5-ylmethyl)-5-nitropyrimidine-2,4-diamine;
N-(2-methyl-1H-indol-5-yl)-2-chloro-pyrimidin-4-amine;
N-(2-chloropyrimidin-4-yl)-1,2-dimethyl-1H-indol-5-amine;
methyl 5-(2-chloropyrimidin-4-ylamino)-1H-indole-2-carboxylate;
N-(2-chloropyrimidin-4-yl)-2,3-dimethyl-1H-indol-5-amine;
N-(2-chloropyrimidin-4-yl)-1H-benzo[c/]imidazol-5-amine;
N-(2-chloropyrimidin-4-yl)-2-methyl-1H-benzo[c/]imidazol-5-amine;
2-chloro-6-methyl-N-[(2-methyl-1H-indol-5-yl)methyl]pyrimidin-4-amine;
2-[(tert-butyldimethylsilyloxy)methyl]-N-(2-chloropyrimidin-4-yl)-1H-indol-5-amine;
N-(2-chloropyrimidin-4-yl)-N,2-dimethyl-1H-indol-5-amine;
N-(2-chloropyrimidin-4-yl)-N,1,2-trimethyl-1H-indol-5-amine;
4-chloro-N-[2-(5-methoxy-1-methyl-1H-indol-3-yl)ethyl]pyrimidin-2-amine; and
4-chloro-N-[2-(5-methoxy-1-methyl-1H-indol-3-yl)ethyl]-N-methylpyrimidin-2-amine.

These intermediate compounds may be used in processes for manufacturing compounds of formula I. Further, These intermediate compounds may be active as such, in therapy in general as well as in the uses and methods as set out in this specification.

Depending upon the substituents present in compounds of the formula I, the compounds may form esters, amides and/or salts which are within the scope of the present invention. Salts and solvates of compounds of formula I which are suitable for use in medicine are those wherein a counterion or an associated solvent is pharmaceutically acceptable. However, salts and solvates having non-pharmaceutically acceptable counterions or associated solvents are within the scope of the present invention, for example, for use as intermediates in the preparation of the compounds of formula I and their pharmaceutically acceptable salts, solvates and physiologically functional derivatives. By the term "physiologically functional derivative" is meant a chemical derivative of a compound of formula I having the same physiological function as the free compound of formula I, for example, by being convertible in the body thereto. Esters and amides are examples of physiologically functional derivatives.

A compound which, upon administration to the recipient, is capable of being converted into a compound of formula I as described above, or an active metabolite or residue thereof, is known as a "prodrug". A prodrug may, for example, be converted within the body, e.g. by hydrolysis in the blood, into its active form that has medical effects. Pharmaceutical acceptable prodrugs are described in T. Higuchi and V. Stella, Prodrugs as Novel Delivery Systems, Vol. 14 of the A. C. S. Symposium Series (1976); "Design of Prodrugs" ed. H. Bundgaard, Elsevier, 1985; and in Edward B. Roche, ed., Bioreversible Carriers in Drug Design, American Pharmaceutical Association and Pergamon Press, 1987, which are incorporated herein by reference.

Suitable salts according to the invention include those formed with organic or inorganic acids or bases. In particular, suitable salts formed with acids according to the invention include those formed with mineral acids, strong organic carboxylic acids, such as alkanecarboxylic acids of 1 to 4 carbon atoms which are unsubstituted or substituted, for example, by halogen, such as saturated or unsaturated dicarboxylic acids, such as hydroxycarboxylic acids, such as amino acids, or with organic sulfonic acids, such as ($C_1$-$C_4$)alkyl- or aryl-sulfonic acids which are unsubstituted or substituted, for example by halogen. Pharmaceutically acceptable acid addition salts include those formed from hydrochloric, hydrobromic, sulphuric, nitric, citric, tartaric, acetic, phosphoric, lactic, pyruvic, acetic, trifluoroacetic, succinic, perchloric, fumaric, maleic, glycolic, lactic, salicylic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine and arginine. Other acids such as oxalic, while not in themselves pharmaceutically acceptable, may be useful as intermediates in obtaining the compounds of the invention and their pharmaceutical acceptable acid addition salts.

Pharmaceutically acceptable base salts include ammonium salts, alkali metal salts, for example those of potassium and sodium, alkaline earth metal salts, for example those of calcium and magnesium, and salts with organic bases, for example dicyclohexylamine, N-methyl-D-glucamine, morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl-propylamine, or a mono-, di- or trihydroxy lower alkylamine, for example mono-, di- or triethanolamine. Corresponding internal salts may furthermore be formed.

Those skilled in the art of organic chemistry will appreciate that many organic compounds can form complexes with solvents in which they are reacted or from which they are precipitated or crystallized. These complexes are known as "solvates". For example, a complex with water is known as a "hydrate".

The following definitions apply to the terms as used throughout this specification, unless otherwise limited in specific instances.

As used herein, the term "alkyl" means both straight and branched chain saturated hydrocarbon groups. Examples of alkyl groups include methyl, ethyl, n-propyl, iso-propyl, n-butyl, iso-butyl, sec-butyl, and t-butyl groups. Among unbranched alkyl groups, there are preferred methyl, ethyl, n-propyl, and n-butyl groups. Among branched alkyl groups, there may be mentioned iso-propyl, iso-butyl, sec-butyl, and t-butyl groups.

As used herein, the term "alkoxy" means the group O-alkyl, where "alkyl" is used as described above. Examples of alkoxy groups include, but are not limited to, methoxy and ethoxy groups. Other examples include propoxy and butoxy.

As used herein, the term "aryl" means a monocyclic or bicyclic aromatic carbocyclic group. Examples of aryl groups include phenyl and naphthyl. A naphthyl group may be attached through the 1 or the 2 position. In a bicyclic aromatic group, one of the rings may, for example, be partially saturated. Examples of such groups include indanyl and tetrahydronaphthyl. Specifically, the term $(C_6-C_{10})$aryl is used herein to mean a group comprising from 6 to 10 carbon atoms in a monocyclic or bicyclic aromatic group. A particularly preferred $(C_6-C_{10})$aryl group is phenyl.

As used herein, the term "halogen" means fluorine, chlorine, bromine or iodine. Fluorine, chlorine and bromine are particularly preferred.

As used herein, the term "heteroaryl" means an aromatic cyclic group of carbon atoms wherein from one to three of the carbon atoms is/are replaced by one or more heteroatoms independently selected from nitrogen, oxygen or sulfur. A heteroaryl group may, for example, be monocyclic, bicyclic or tricyclic.

Examples of monocyclic heteroaryl groups include, but are not limited to, furanyl, thienyl, pyrrolyl, oxazolyl, thiazolyl, imidazolyl, oxadiazolyl, thiadiazolyl, pyridyl, triazolyl, triazinyl, pyridazyl, isothiazolyl, isoxazolyl, pyrazinyl, pyrazolyl, and pyrimidinyl.

Examples of bicyclic heteroaryl groups include, but are not limited to, quinoxalinyl, quinazolinyl, pyridopyrazinyl, benzoxazolyl, benzothiophenyl, benzimidazolyl, naphthyridinyl, quinolinyl, benzofuranyl, indolyl, indazolyl, benzothiazolyl, pyridopyrimidinyl, and isoquinolinyl.

Examples of tricyclic heteroaryl groups include, but are not limited to, carbazole, dibenzofuran, xanthene, and acridine.

As used herein, the term "heterocyclyl" means a cyclic group of carbon atoms wherein from one to three of the carbon atoms is/are replaced by one or more heteroatoms independently selected from nitrogen, oxygen and sulfur. Examples of heterocyclyl groups include, but are not limited to, tetrahydrofuranyl, pyrrolidinyl, piperidinyl, piperazinyl, morpholinyl, and dioxanyl.

The compounds of the invention may be used in the prophylaxis and treatment as such, or preferably in a form of a pharmaceutical composition. While it is possible for the active ingredient to be administered alone, it is preferable for it to be present in a pharmaceutical formulation or composition. Accordingly, the invention provides a pharmaceutical formulation comprising a compound according to the invention, and a pharmaceutically acceptable diluent, excipient or carrier (collectively referred to herein as "carrier" materials). Pharmaceutical compositions of the invention may take the form of a pharmaceutical formulation as described below. Thus, the present invention relates to a pharmaceutical composition containing at least one compound of Formula I together with conventional excipients.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate, calcium sulfate, sorbitol, glucose and/or lactose and/or other excipients, binders, extenders, disintegrants, diluents and lubricants such as those known in the art. Suitable binders include starch, gelatin, natural sugars such as glucose or beta-lactose, corn sweeteners, natural and synthetic gums such as acacia, tragacanth or sodium alginate, carboxymethylcellulose, poly-ethylene glycol, waxes and the like. Disintegrators include without limitation starch, methylcellulose, agar, bentonite, xanthan gum and the like. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use. Lubricants used in these dosage forms include sodium oleate, sodium stearate, magnesium stearate, sodium benzoate, sodium acetate, sodium chloride and the like. For oral administration in liquid form, the oral drug components can be combined with any oral, non-toxic, pharmaceutically acceptable inert carrier such as ethanol, glycerol, water, and the like.

The pharmaceutical formulations according to the invention include those suitable for oral, parenteral (including subcutaneous, intradermal, intramuscular, intravenous [bolus or infusion], and intraarticular), inhalation (including fine particle dusts or mists which may be generated by means of various types of metered dose pressurized aerosols), nebulizers or insufflators, rectal, intraperitoneal and topical (including dermal, buccal, sublingual, and intraocular) administration, although the most suitable route may depend upon, for example, the condition and disorder of the recipient.

Formulations of the present invention suitable for oral administration may be presented as discrete units such as capsules, cachets, pills or tablets each containing a predetermined amount of the active ingredient; as a powder or granules; as a solution or a suspension in an aqueous liquid or a non-aqueous liquid, for example as elixirs, tinctures, suspensions or syrups; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

The compounds of the present invention can also be administered in the form of liposome delivery systems, such as small unilamellar vesicles, large unilamellar vesicles and multilamellar vesicles. Liposomes can be formed from a variety of phospholipids, 1,2-dipalmitoylphosphatidylcholine, phosphatidyl ethanolamine (cephaline), phosphatidylserine, phosphatidylinositol, diphosphatidylglycerol (cardiolipin) or phosphatidylcholine (lecithin).

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as polyethylene glycol, ethanol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for nasal, aerosol or inhalation administration include solutions in saline, which can contain, for example, benzyl alcohol or other suitable preservatives, absorption promoters to enhance bioavailability, and/or other solubilizing or dispersing agents such as those known in the art.

Formulations for rectal administration may be presented as a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

The amount of active ingredient which is required to achieve a therapeutic effect will, of course, vary with the particular compound, the route of administration, the subject under treatment, including the type, species, age, weight, sex, and medical condition of the subject and the renal and hepatic function of the subject, and the particular disorder or disease being treated, as well as its severity. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 mg per kg of body weight per day (mg/kg/day) to 10 mg/kg/day, and most preferably 0.1 to 5.0 mg/kg/day, for adult humans. For oral administration, the compositions are preferably provided in the form of tablets or other forms of presentation provided in discrete units containing 0.01, 0.05, 0.1, 0.5, 1.0, 2.5, 5.0, 10.0, 15.0, 25.0, 50.0, 100, and 500 milligrams of the active ingredient for the symptomatic adjustment of the dosage to the patient to be treated. A medicament typically contains from about 0.01 mg to about 500 mg of the active ingredient, preferably from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

The invention also provides the use of a compound of formula I, for the manufacture of a medicament for the treatment or prophylaxis of cancer.

The compounds and the pharmaceutical compositions of the invention may be used in the prophylaxis and treatment of diseases such as cancer, diseases caused by parasites, allergic diseases, Crohns disease, rheumatic diseases, tuberculosis, diabetes, Alzheimer's disease, inflammatory diseases, multiple sclerosis (MS), amyotrophic lateral sclerosis (ALS), Parkinson's disease and diseases caused by bacteria, viruses and fungus.

The compounds of the invention find particular application in the treatment or prophylaxis of various cancer types, including but not limited to, cancer of the bone, breast, respiratory tract, brain, reproductive organs, bone marrow, digestive tract, urinary tract, eye, liver, skin, head, neck, thyroid, parathyroid, and metastatic forms thereof. Proliferative disorders of the breast include, but are not limited to, invasive ductal carcinoma, invasive lobular carcinoma, ductal carcinoma, lobular carcinoma in situ, and metastatic breast cancer. Proliferative disorders of the skin include, but are not limited to, basal cell carcinoma, squamous cell carcinoma, malignant melanoma, and Kaposi's sarcoma. Proliferative disorders of the respiratory tract include, but are not limited to, lung cancer, doxorubicin resistant lung cancer, small cell and non-small cell lung carcinoma, bronchial adenoma, pleuropulmonary blastoma, and malignant mesothelioma. Proliferative disorders of the brain include, but are not limited to, brain stem and hypothalamic glioma, cerebellar and cerebral astrocytoma, medulloblastoma, ependymal tumors, oligodendroglial tumors, meningiomas and neuroectodermal, and pineal tumors. Proliferative disorders of the male reproductive organs include, but are not limited to, prostate, testicular and penis cancer.

Proliferative disorders of the female reproductive organs include, but are not limited to, uterine, cervical, ovarian, vaginal, vulval cancer, uterine sarcoma, ovarian germ cell tumor, ovarian cancer, doxorubicin resistant ovarian cancer, and cisplatin resistant ovarian cancer. Proliferative disorders of the digestive tract include, but are not limited to, anal, colon, colorectal, esophageal, gall bladder, stomach, pancreatic, rectal, small intestine, and salivary gland cancer. Proliferative disorders of the liver include, but are not limited to, hepatocellular carcinoma, cholangiocarcinoma, and primary liver cancer. Proliferative disorders of the eye include, but are not limited to, intraocular melanoma, retinoblastoma, and rhabdomyosarcoma. Proliferative disorders of the head include, but are not limited to, laryngeal, hypopharyngeal, nasopharyngeal, oropharyngeal, lip, oral, and metastatic paranasal sinus cancer. Proliferative disorders of the lymphomas include, but are not limited to, T cell and B cell lymphomas, non-Hodgkins lymphoma, cutaneous T cell lymphoma, Hodgkins disease, vincristin resistant lymphoma, and lymphoma of the central nervous system. Leukaemia includes, but is not limited to, acute myeloid leukaemia, chronic myelogenous leukaemia, acute lymphocytic leukaemia, chronic lymphocytic leukaemia, teponiside resistant leukaemia, and hairy cell leukaemia. Proliferative disorders of the thyroid include, but are not limited to, thyroid cancer, thymoma, and malignant thymoma. Proliferative disorders of bone marrow include, but are not limited to, myeloma, and doxorubicin resistant myeloma. Proliferative disorders of the urinary tract include, but are not limited to, kidney cancer and bladder cancer. Sarcomas include, but are not limited to, sarcoma of the soft tissue, osteosarcoma, malignant fibrous histiocytoma, lymphosarcoma, and rhabdomyosarcoma. Whilst a compound of the invention may be used alone, it is also possible for the compounds to be used in combination with each other, in combination with radiation therapy, or in combination with other anticancer agents. Various classes of anticancer and antineoplastic compounds include, but are not limited to, alkylating agents, antimetabolites, anticancer camptothecin derivatives, plant-derived anticancer agents, antibiotics, enzymes, platinum coordination complexes, tyrosine kinase inhibitors, hormones and hormone antagonists, monoclonal antibodies, interferons, biological response modifiers and other anticancer agents. Examples of alkylating agents include, but are not limited to, mechlorethamine, cyclophosphamide, ifosfamide, melphalan, chlorambucil, busulfan, mitobronitol, ranimustin, nimustin, temozolomide and carmustine; examples of antimetabolites include, but are not limited to, methotrexate, fluorouracil, cytarabine, gemcitabine, fludarabine, mercaptopurine, thioguanine, and azathioprine; examples of camptothecin derivatives include, but are not limited to, irinotecan, topotecan, and camptothecin; examples of plant-derived agents include, but are not limited to, vinca alkaloids e.g. vinblastine and vincristine, taxanes, e.g. paclitaxel and docetaxel, and colchicines; examples of antibiotics include, but are not limited to, actinomycin D, daunorubicin, and bleomycin. One example of enzyme effective as antineoplastic agent includes L-asparaginase. Examples of coordination compounds include, but are not limited to, cisplatin and carboplatin; examples of tyrosine kinase inhibitors include, but are not limited to, gefitinib, imatinib, sunitinib, nilotinib, dasatinib, erlotinib, and pazopanib; examples of hormones and hormone related compounds include, but are not limited to, prednisone, dexamethasone, formestane, aminoglutethimide, anastrozole, hydroxyprogesterone caproate, medroxyprogesterone and tamoxifen; examples of interferons include, but are not limited to, interferon α, interferon α-2a, interferon α-2b, interferon β, interferon γ-1a, and interferon γ-n1; examples of biological response modifiers include, but are not limited to, krestin, lentinan, sizofuran, picibanil, and ubenimex. Examples of other anticancer agents include, but are not limited to, mitoxantrone, procarbazine, dacarbazine, hydroxycarbamide, pentostatin, tretinoin, leuprorelin, flutamide, and aldesleukin.

Numerous synthetic routes to the compounds of the present invention can be devised by any person skilled in the art and the possible synthetic routes described below do not limit the invention.

Procedure for Synthesizing the Compounds of General Formula I

The appropriate amine (II) was dissolved in iso-propanol (0.2 g/mL). 1.1 Eq of pyrimidine (III) and 1.2 eq of N,N-diisopropylethylamine (DIPEA) were added and the mixture was stirred at 50-120° C. for 1-3 h. The reaction mixture was dissolved in EtOAc/MeOH 5:1 and washed with saturated aqueous NaHCO₃, water and brine. The solvent was removed in vacuo and the residue was purified by column chromatography on silica gel with heptane/EtOAc or EtOAc/MeOH as eluent to give the major intermediate (IV') and the minor intermediate (IV").

The intermediate (IV' or IV") was dissolved in ethylene glycol (0.2 g/mL) and 1.1 eq of amine (V) was added. The mixture was then stirred at 100-150° C. for 1-3 h. The reaction mixture was dissolved in EtOAc/MeOH 5:1 and washed with saturated aqueous NaHCO₃, water and brine. The solvent was removed in vacuo and the residue was purified by column chromatography on silica gel with heptane/EtOAc or EtOAc/MeOH/TEA as eluent to give the compound of formula I. This procedure is exemplified in Scheme 1.

Scheme 1

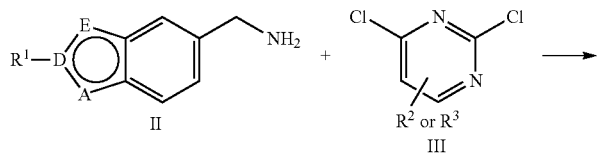

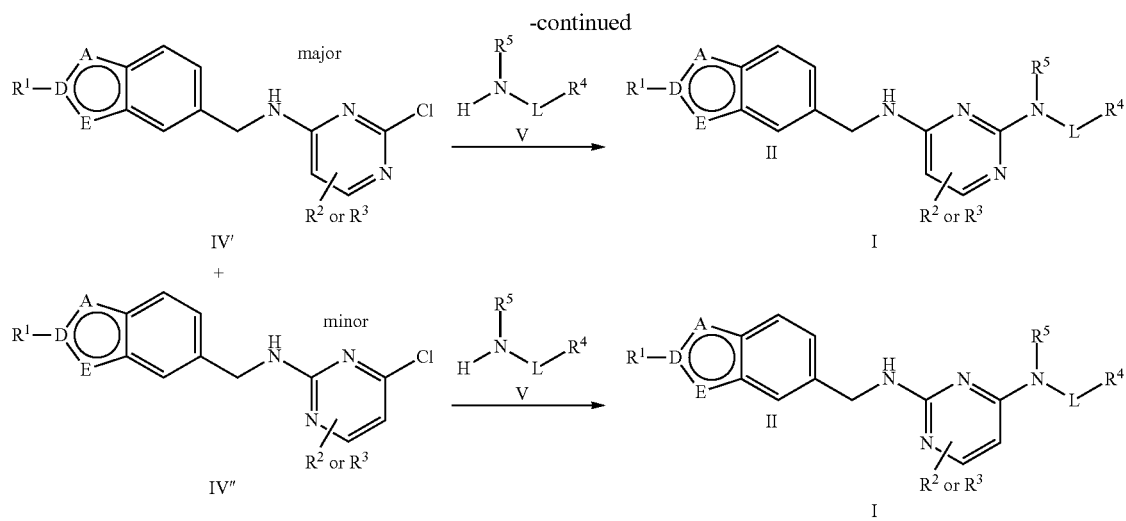

Compounds of Examples 1-22, 24, 26-28, 30-37, 62, 64, 66, 68, 69, 71-91, 97-103, and 109 were synthesized by this general reaction procedure (as set out in Scheme 1.). Note that Example 102 was obtained by a final ester hydrolysis step using potassium hydroxide in methanol. A, D, E, $R^1$ to $R^5$, and L are as defined in formula I.

General Procedure for Synthesizing the Compounds of General Formula I, Represented by Formula VII, Starting from Compounds of Formula VI The intermediate VI which was synthesized by the general procedure in Scheme 1 was dissolved in MeOH (1.5 mg/mL) and 10% Pd/C (20 mol %) was added. The flask was pump-purged with argon and then with hydrogen. The reaction mixture was left stirring vigorously under hydrogen atmosphere at room temperature for 20 h. The catalyst was filtered off and the solvent was evaporated yielding pure product VII, as exemplified in Scheme 2.

Scheme 2

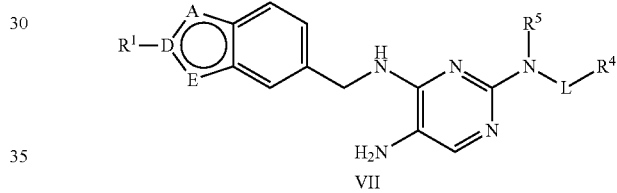

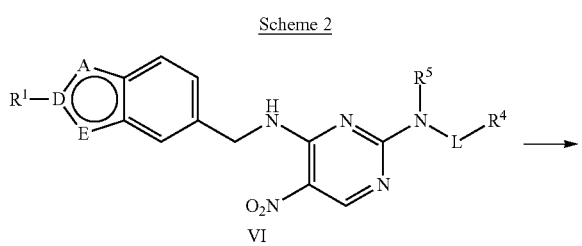

Compounds of Examples 38-41 were synthesized by this general reaction procedure (as set out in Scheme 2.). A, D, E, $R^1$, $R^4$, $R^5$, and L are as defined in formula I.

Alternative Procedure for Synthesizing the Compounds of General Formula I

In some cases appropriate amines were introduced in reversed order to give the compounds of formula I more efficiently via intermediate VIII. The conditions for this procedure resembles the one described for Scheme 1 and are exemplified in Scheme 3.

Scheme 3

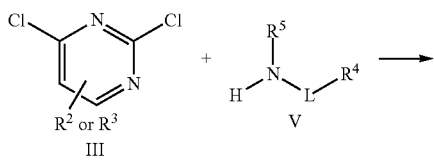

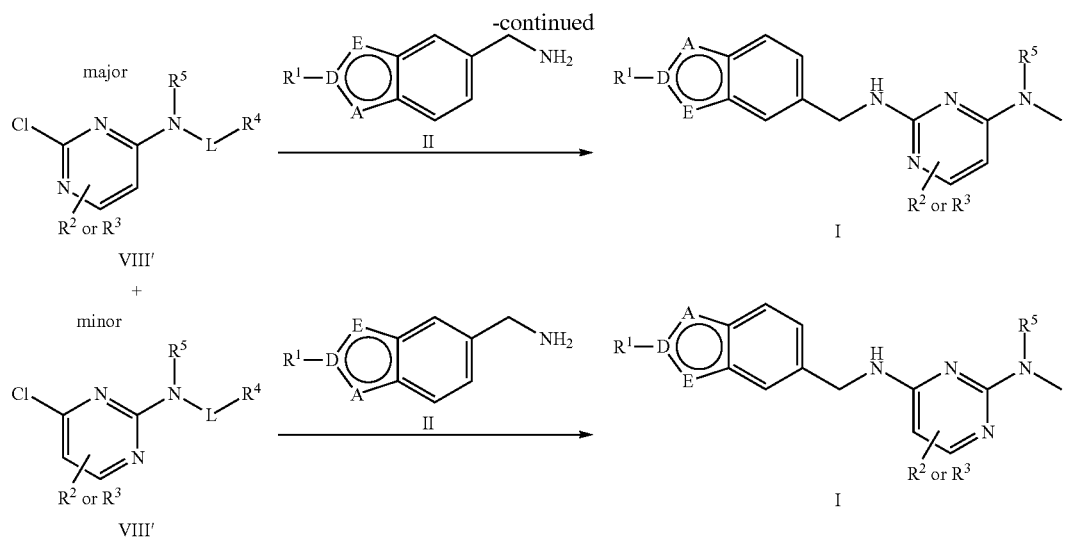

The procedure described in scheme 3 was utilized in the syntheses of Examples 23, 25, 29, 63, 65, 67, 70, 92-96, and 104-108. Note that Example 104 was obtained by a final desilylation step by the action of tetrabutylammonium fluoride. A, D, E, $R^1$ to $R^5$, and L are as defined in formula I.

Procedure for Synthesizing the Intermediates of General Formula IX where $R^5$=Me and/or $R^6$=Me In order to access certain methylated analogues the appropriate monosubstituted pyrimidine (VIII) was dissolved in dimethylformamide (0.1 g/mL). 2 Eq of $Cs_2CO_3$ and 2 eq of iodomethane were added and the mixture was stirred at 20-40° C. for 2-5 days. The reaction mixture was dissolved in EtOAc and washed with water. The solvent was removed in vacuo and the residue was purified by column chromatography on silica gel with heptane/EtOAc as eluent to give the compound (IX). The procedure is exemplified in Scheme 4.

The monomethylated compound IX'a (Intermediate 117) was obtained as a major product under these reaction conditions and used in the synthesis of Example 105. A minor component was obtained due to an additional methylation at the indole nitrogen. This dimethylated compound IX'b (Intermediate 118) was used in the synthesis of Example 106.

Under the same reaction conditions, monomethylation at the indole nitrogen yielded IX''a (Intermediate 119) that was used in the synthesis of Example 107. As a minor product, the dimethylated compound IX''b (Intermediate 120) was obtained and used in the synthesis of Example 108.

Scheme 4

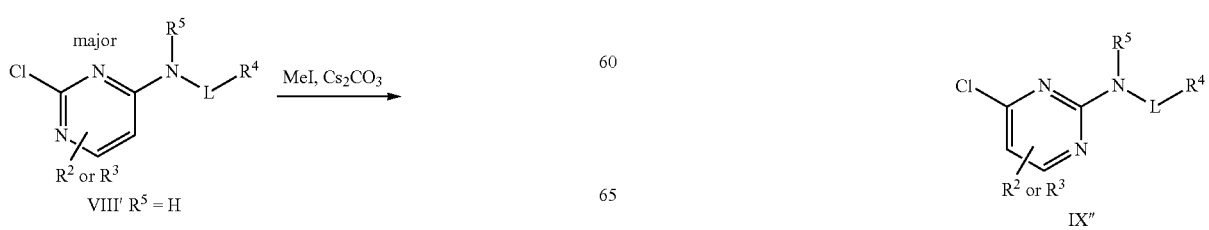

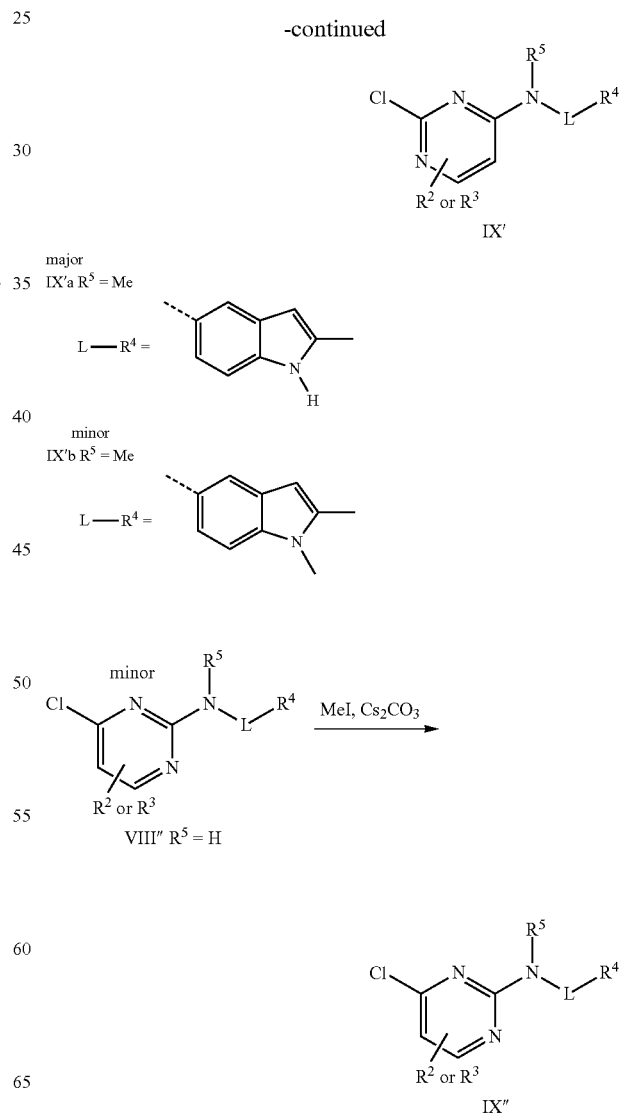

-continued major
IX″a R⁵ = H

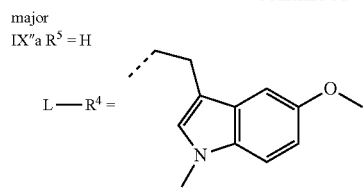

minor
IX″b R⁵ = Me

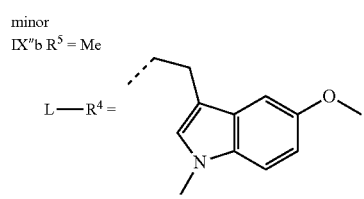

Intermediate compounds 117-120 were synthesized by this reaction procedure (as set out in scheme 4). $R^1$-$R^3$ are as defined in formula I.

Procedure for Synthesizing Alkylated Serotonin Derivatives of Formula XVIII, Used in the Syntheses of Examples 73, 74, and 87

Step 1: Serotonin hydrochloride (X) was dissolved in water (20 mg/mL). 3 Eq of potassium carbonate and 1 eq of di-tert-butyl dicarbonate were added and the mixture was stirred at room temperature for 24 h. The aqueous reaction mixture was extracted with EtOAc and the organic phase was washed with water, 1 M HCl(aq) and brine. The solvent was removed in vacuo and the residue was purified by column chromatography on silica gel with $CH_2Cl_2$/MeOH as eluent to give tert-butyl 2-(5-hydroxy-1H-indol-3-yl) ethylcarbamate (XI).

Step 2: Tert-butyl 2-(5-hydroxy-1H-indol-3-yl)ethylcarbamate (XI), 3-9 eq potassium carbonate, and 0.1-1 eq NaI were premixed in 2-butanone (25 mg/mL). After 5 min, 3-5 eq alkyl halide ($R^1$—X=4-(2-chloroethyl) morpholine*HCl or 2-bromoethyl methyl ether or bromoethane) was added and the mixture was stirred at 90° C. for 3-5 days. The reaction mixture was dissolved in EtOAc and washed with saturated aqueous $NaHCO_3$. The solvent was removed in vacuo and the residue was purified by column chromatography on silica gel with $CH_2Cl_2$/acetone to give the alkylated derivative (XII).

Step 3: The alkylated derivative (XII) was dissolved in $CH_2Cl_2$/trifluoroacetic acid 2:1 (25 mg/mL) and kept at room temperature for 30-90 min. The reaction mixture was concentrated in vacuo, co-evaporated with toluene and the residue was purified by column chromatography on silica gel with EtOAc/MeOH/TEA as eluent to give the desired amine (XIII).

This procedure is exemplified in Scheme 4.

Scheme 4

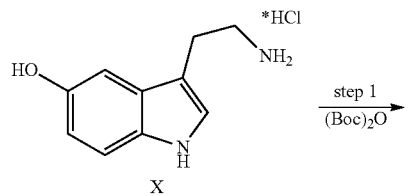

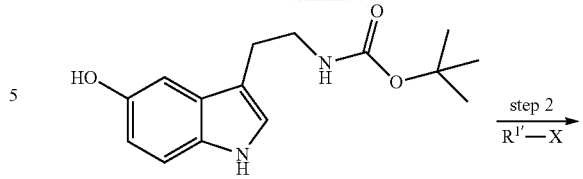

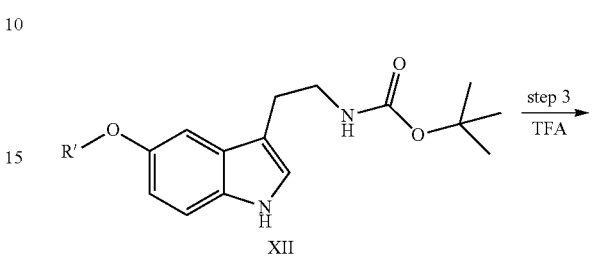

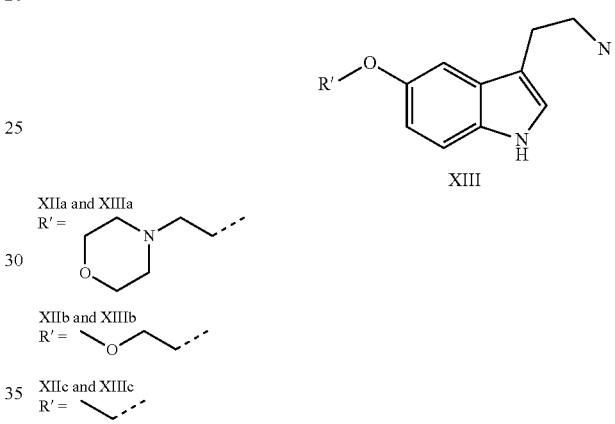

XIIa and XIIIa
R′ =

XIIb and XIIIb
R′ =

XIIc and XIIIc
R′ =

Alkylated serotonin derivatives (XIIIa was used in the synthesis of Example 73, XIIIb was used in the synthesis of Example 74, and XIIIc was used in the synthesis of Example 87) were synthesized by this reaction procedure (as set out in Scheme 4.).

Below follows non-limiting examples of the invention.

EXAMPLE 1

$N^4$-(1H-indol-5-ylmethyl)-$N^2$-(1H-indol-4-yl)pyrimidine-2,4-diamine

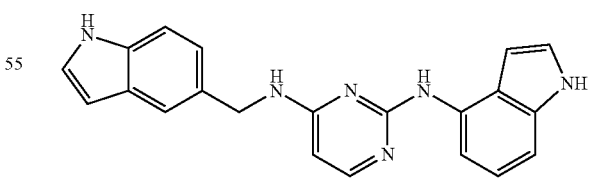

$^1$H NMR (500 MHz, DMSO-$d_6$) δ 11.00 (s, 1H), 10.95 (s, 1H), 8.33 (s, 1H), 7.85 (d, 1H), 7.81 (d, 1H), 7.58 (br s, 1H), 7.49 (s, 1H), 7.34 (d, 1H), 7.30 (t, 1H), 7.19 (t, 1H), 7.09 (d, 1H), 6.99 (m, 2H), 6.80 (m, 1H), 6.36 (m, 1H), 5.98 (d, 1H), 4.61 (br s, 2H).

MS (ESI$^+$) m/z 355.3 [M+H]$^+$.

EXAMPLE 2

N$^4$-(1H-indol-5-ylmethyl)-N$^2$-(1H-indol-5-yl)pyrimidine-2,4-diamine

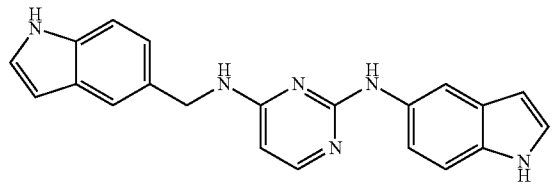 [SMILES: c1cc(NCc2ccc3[nH]ccc3c2)nc(Nc2ccc3[nH]ccc3c2)n1]

$^1$H NMR (500 MHz, DMSO-d$_6$) δ 11.00 (s, 1H), 10.80 (s, 1H), 8.60 (s, 1H), 8.00 (m, 1H), 7.76 (d, 1H), 7.50 (s, 1H), 7.49 (br s, 1H), 7.34-7.28 (m, 3H), 7.22-7.19 (m, 2H), 7.10 (m, 1H), 6.35 (m, 1H), 6.27 (m, 1H), 5.91 (d, 1H), 4.61 (br s, 2H).

MS (ESI$^+$) m/z 355.3 [M+H]$^+$.

EXAMPLE 3

N$^4$-(1H-indol-5-ylmethyl)-N$^2$-(2-methyl-1H-indol-5-yl)pyrimidine-2,4-diamine

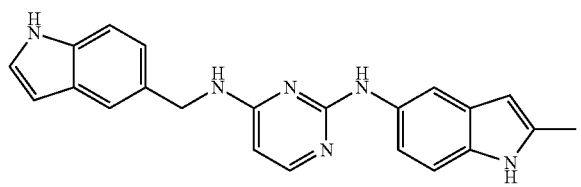 [SMILES: Cc1cc2cc(Nc3nccc(NCc4ccc5[nH]ccc5c4)n3)ccc2[nH]1]

$^1$H-NMR (500 MHz, DMSO-d$_6$) δ 10.99 (s, 1H), 10.60 (s, 1H), 8.53 (s, 1H), 7.84 (d, 1H), 7.75 (d, 1H), 7.50 (s, 1H), 7.46 (br. s, 1H), 7.33 (d, 1H), 7.29 (t, 1H), 7.21 (dd, 1H), 7.10 (dd, 1H), 7.07 (d, 1H), 6.35 (br. s, 1H), 5.96 (s, 1H), 5.89 (d, 1H), 4.59 (br. s, 2H), 2.33 (s, 3H).

MS (ESI$^+$) m/z 369.3 [M+H]$^+$.

EXAMPLE 4

N$^4$-(1H-indol-5-ylmethyl)-N$^2$-(1H-indazol-5-yl)pyrimidine-2,4-diamine

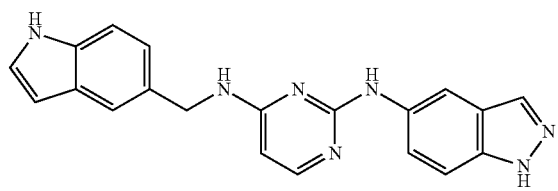 [SMILES: c1cc(NCc2ccc3[nH]ccc3c2)nc(Nc2ccc3[nH]ncc3c2)n1]

$^1$H-NMR (500 MHz, CD$_3$OD) δ 8.01 (s, 1H), 7.80 (br. s, 1H), 7.72 (d, 1H), 7.51 (s, 1H), 7.43 (dd, 1H), 7.39 (d, 1H), 7.33 (d, 1H), 7.19 (d, 1H), 7.10 (dd, 1H), 6.37 (d, 1H), 5.97 (d, 1H), 4.64 (br. s, 2H).

MS (ESI$^+$) m/z 356.3 [M+H]$^+$.

EXAMPLE 5

N$^4$-(1H-indol-5-ylmethyl)-N$^2$-(2-methyl-1H-indol-5-ylmethyl)pyrimidine-2,4-diamine

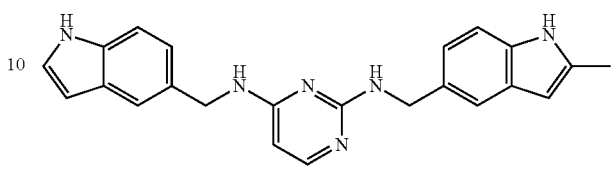

$^1$H NMR (500 MHz, DMSO-d$_6$) δ 10.99 (s, 1H), 10.74 (s, 1H), 7.61 (d, 1H), 7.45 (s, 1H), 7.30-7.28 (m, 3H), 7.25 (br s, 1H), 7.13 (d, 1H), 7.05 (dd, 1H), 6.96 (dd, 1H), 6.75 (br s, 1H), 6.34 (br s, 1H), 5.99 (br s, 1H), 5.72 (d, 1H), 4.51 (br s, 2H), 4.46 (d, 2H), 2.34 (s, 3H).

MS (ESI$^+$) m/z 383.3 [M+H]$^+$.

EXAMPLE 6

N$^2$-(1H-indazol-5-ylmethyl)-N$^4$-(1H-indol-5-ylmethyl)pyrimidine-2,4-diamine

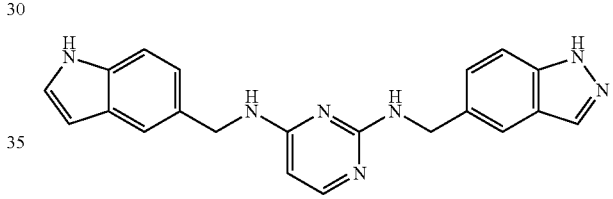

$^1$H NMR (500 MHz, DMSO-d$_6$) δ 12.92 (s, 1H), 10.99 (s, 1H), 7.92 (br s, 1H), 7.61 (d, 1H), 7.59 (s, 1H), 7.43-7.39 (m, 2H), 7.33-7.28 (m, 4H), 7.02 (d, 1H), 6.95 (br s, 1H), 6.32 (s, 1H), 5.74 (d, 1H), 4.51 (d, 4H).

MS (ESI$^+$) m/z 370.3 [M+H]$^+$.

EXAMPLE 7

N$^2$-(1H-benzo[d]imidazol-5-ylmethyl)-N$^4$-(1H-indol-5-ylmethyl)pyrimidine-2,4-diamine

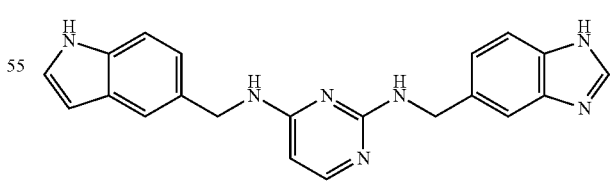

$^1$H NMR (500 MHz, DMSO-d$_6$, 75° C.) δ 12.10 (br s, 1H), 10.83 (br s, 1H), 8.10 (s, 1H), 7.65 (s, 1H), 7.54 (s, 1H), 7.48-7.46 (m, 3H), 7.30 (d, 1H), 7.27 (t, 1H), 7.18 (d, 1H), 7.04 (d, 1H), 7.00 (br s, 1H), 6.34 (br s, 1H), 5.85 (d, 1H), 4.60 (d, 2H), 4.54 (d, 2H).

MS (ESI$^+$) m/z 370.2 [M+H]$^+$.

EXAMPLE 8

N⁴-(1H-indol-5-ylmethyl)-N²-(1H-indol-6-ylmethyl)pyrimidine-2,4-diamine

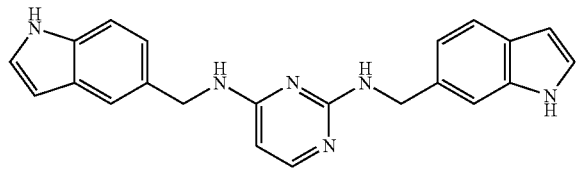 [SMILES: c1cc(NCc2ccc3[nH]ccc3c2)nc(NCc2ccc3cc[nH]c3c2)n1]

¹H NMR (500 MHz, DMSO-d₆) δ 10.98 (s, 1H), 10.93 (s, 1H), 7.62 (d, 1H), 7.44 (s, 1H), 7.40 (d, 1H), 7.32 (s, 1H), 7.29-7.24 (m, 4H), 7.03 (d, 1H), 6.96 (d, 1H), 6.88 (br s, 1H), 6.35 (m, 1H), 6.32 (br s, 1H), 5.73 (d, 1H), 4.52 (d, 2H), 4.50 (br s, 2H).

MS (ESI⁺) m/z 369.3 [M+H]⁺.

EXAMPLE 9

N²-[2-(1H-indol-3-yl)ethyl]-N⁴-(1H-indol-5-ylmethyl)pyrimidine-2,4-diamine

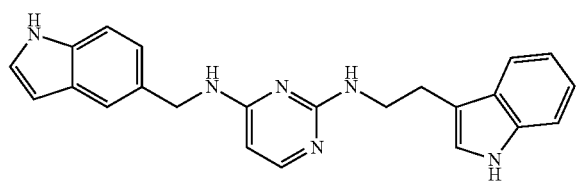 [SMILES: c1ccc2c(CCNc3nccc(NCc4ccc5[nH]ccc5c4)n3)c[nH]c2c1]

¹H-NMR (300 MHz, CDCl₃) δ 8.20 (br s, 1H), 7.95 (br s, 1H), 7.83 (d, 1H), 7.65 (d, 1H), 7.60 (s, 1H), 7.38-6.91 (m, 7H), 6.53 (br s, 1H), 5.73 (d, 1H), 4.94 (m, 2H), 4.58 (m, 2H), 3.73 (q, 2H), 3.06 (t, 2H).

MS (ESI⁺) m/z 383.3 [M+H]⁺.

EXAMPLE 10

3-{2-[4-(1H-indol-5-ylmethylamino)-pyrimidin-2-ylamino]ethyl}-1H-indol-5-ol

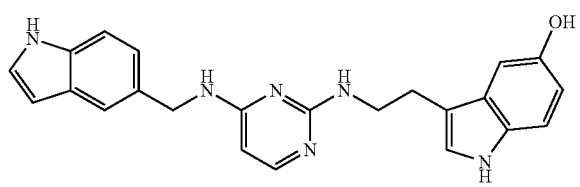 [SMILES: Oc1ccc2[nH]cc(CCNc3nccc(NCc4ccc5[nH]ccc5c4)n3)c2c1]

¹H-NMR (500 MHz, DMSO-d₆) δ 10.99 (s, 1H), 10.44 (s, 1H), 8.56 (s, 1H), 7.65 (br. s, 1H), 7.47 (s, 1H), 7.31 (d, 1H), 7.29 (t, 1H), 7.25 (br. s, 1H), 7.11 (d, 1H), 7.06 (d, 1H), 7.02 (s, 1H), 6.87 (d, 1H), 6.58 (dd, 1H), 6.34 (br. s, 2H), 5.75 (br. s, 1H), 4.52 (br. s, 2H), 3.46 (q, 2H), 2.81 (t, 2H).

MS (ESI⁺) m/z 399.3 [M+H]⁺.

EXAMPLE 11

N⁴-(1H-indol-5-ylmethyl)-N²-[2-(5-methyl-1H-indol-3-yl)ethyl]pyrimidine-2,4-diamine

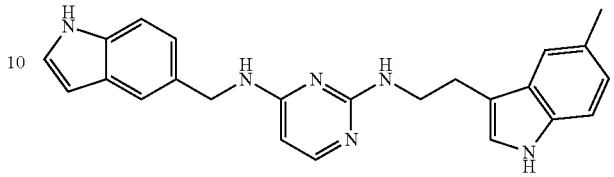

¹H-NMR (500 MHz, DMSO-d₆) δ 10.99 (s, 1H), 10.62 (s, 1H), 7.64 (br. s, 1H), 7.47 (s, 1H), 7.33 (s, 1H), 7.31 (d, 1H), 7.29 (t, 1H), 7.26 (br. s, 1H), 7.19 (d, 1H), 7.08 (s, 1H), 7.06 (d, 1H), 6.86 (d, 1H), 6.37 (br. s, 1H), 6.34 (br. s, 1H), 5.74 (dd, 1H), 4.54 (br. s, 2H), 3.48 (q, 2H), 2.88 (t, 2H), 2.32 (s, 3H).

MS (ESI⁺) m/z 397.3 [M+H]⁺.

EXAMPLE 12

N⁴-(1H-indol-5-ylmethyl)-N²-[2-(5-methoxy-1H-indol-3-yl)ethyl]pyrimidine-2,4-diamine

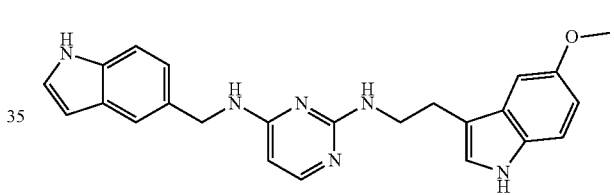

¹H-NMR (500 MHz, DMSO-d₆) δ 10.99 (s, 1H), 10.60 (s, 1H), 7.65 (br. s, 1H), 7.47 (s, 1H), 7.31 (d, 1H), 7.29 (t, 1H), 7.26 (br. s, 1H), 7.20 (d, 1H), 7.10-7.06 (m, 3H), 6.69 (dd, 1H), 6.37 (br. s, 1H), 6.34 (br. s, 1H), 5.75 (s, 1H), 4.53 (br. s, 2H), 3.71 (s, 3H), 3.48 (q, 2H), 2.88 (t, 2H).

MS (ESI⁺) m/z 413.3 [M+H]⁺.

EXAMPLE 13

N²-(1H-indol-4-yl)-N⁴-(2-methyl-1H-indol-5-ylmethyl)pyrimidine-2,4-diamine

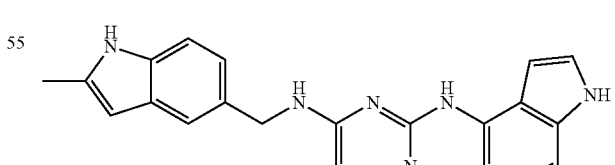

¹H-NMR (500 MHz, DMSO-d₆) δ 10.95 (s, 1H), 10.81 (s, 1H), 8.32 (s, 1H), 7.86 (d, 1H), 7.80 (d, 1H), 7.54 (br s, 1H), 7.35 (s, 1H), 7.19 (d, 1H), 7.18 (s, 1H), 6.97 (m, 3H), 6.80 (s, 1H), 6.05 (s, 1H), 5.98 (d, 1H), 4.58 (br s, 2H), 2.35 (s, 3H).

MS (ESI⁺) m/z 369.3 [M+H]⁺.

EXAMPLE 14

N²-(1H-indol-5-ylmethyl)-N¹-(2-methyl-1H-indol-5-ylmethyl)pyrimidine-2,4-diamine

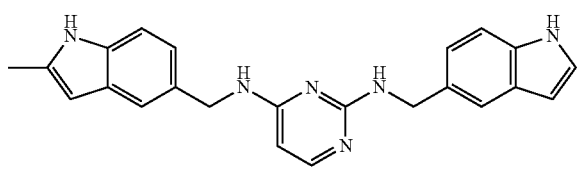 [SMILES: Cc1cc2cc(CNc3ccnc(NCc4ccc5[nH]ccc5c4)n3)ccc2[nH]1]

¹H-NMR (500 MHz, DMSO-d₆) δ 10.95 (s, 1H), 10.79 (s, 1H), 7.61 (d, 1H), 7.44 (s, 1H), 7.30 (s, 1H), 7.26 (dd, 2H), 7.23 (br. s, 1H), 7.15 (d, 1H), 7.06 (d, 1H), 6.94 (d, 1H), 6.79 (br.s, 1H), 6.32 (d, 1H), 6.01 (d, 1H), 5.72 (d, 1H), 4.49 (d, 4H), 2.35 (s, 3H).

MS (ESI⁺) m/z 383.3 [M+H]⁺.

EXAMPLE 15

N²,N¹-Bis-(2-methyl-1H-indol-5-ylmethyl)pyrimidine-2,4-diamine

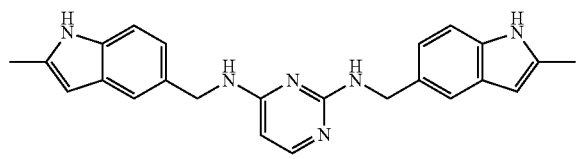

¹H-NMR (500 MHz, DMSO-d₆/D₂O, 75° C.) δ 7.63 (d, 1H), 7.32 (s, 2H), 7.17 (d, 1H), 7.14 (d, 1H), 6.97 (t, 2H), 6.01 (d, 2H), 5.75 (d, 1H), 4.49 (s, 4H), 2.36 (s, 6H).

MS (ESI⁺) m/z 397.4 [M+H]⁺.

EXAMPLE 16

N²-(1H-indazol-5-ylmethyl)-N¹-(2-methyl-1H-indol-5-ylmethyl)pyrimidine-2,4-diamine

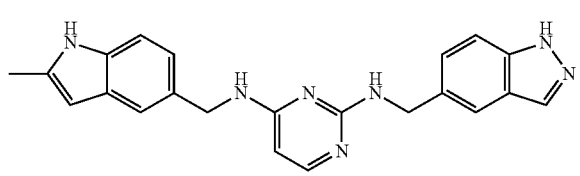 [SMILES: Cc1cc2cc(CNc3ccnc(NCc4ccc5[nH]ncc5c4)n3)ccc2[nH]1]

¹H-NMR (500 MHz, CD₃OD) δ 7.85 (br s, 1H), 7.63 (s, 1H), 7.58 (br s, 1H), 7.41 (d, 1H), 7.36 (d, 1H), 7.29 (s, 1H), 7.11 (d, 1H), 6.91 (d, 1H), 5.97 (s, 1H), 5.83 (d, 1H), 4.64 (s, 2H), 4.59 (br s, 2H), 2.38 (s, 3H).

MS (ESI⁺) m/z 384.3 [M+H]⁺.

EXAMPLE 17

N²-(2-(1H-indol-3-yl)-ethyl)-N⁴-(2-methyl-1H-indol-5-ylmethyl)pyrimidine-2,4-diamine

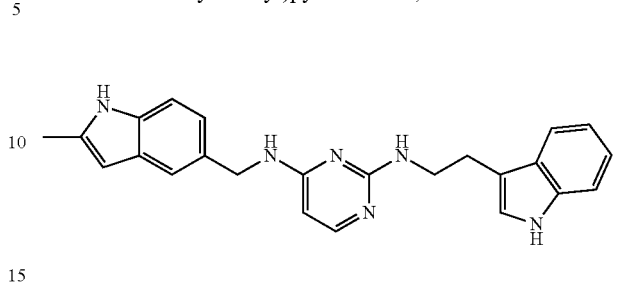

¹H-NMR (500 MHz, DMSO-d₆) δ 10.80 (s, 1H), 10.76 (s, 1H), 7.64 (br s, 1H), 7.55 (d, 1H), 7.32 (s, 1H), 7.31 (s, 1H), 7.25 (br s, 1H), 7.18 (d, 1H), 7.14 (s, 1H), 7.04 (t, 1H), 6.97 (d, 1H), 6.92 (br s, 1H), 6.39 (br s, 1H), 6.02 (s, 1H), 5.74 (s, 1H), 4.51 (br s, 2H), 3.45 (q, 2H), 2.90 (t, 2H), 2.34 (s, 3H).

MS (ESI⁺) m/z 397.3 [M+H]⁺.

EXAMPLE 18

N²-(1H-indol-4-yl)-N⁴-(1H-indazol-5-ylmethyl)pyrimidine-2,4-diamine

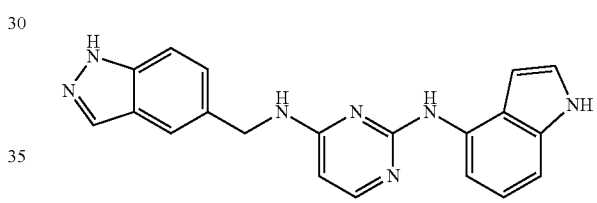

¹H-NMR (500 MHz, DMSO-d₆) δ 12.97 (s, 1H), 10.95 (s, 1H), 8.36 (s, 1H), 7.99 (s, 1H), 7.82 (d, 1H), 7.75 (br s, 1H), 7.68 (br s, 1H), 7.65 (s, 1H), 7.48 (d, 1H), 7.35 (d, 1H), 7.19 (s, 1H), 6.98 (d, 1H), 6.92 (t, 1H), 6.77 (s, 1H), 5.99 (br s, 1H), 4.62 (br s, 2H).

MS (ESI⁺) m/z 356.3 [M+H]⁺.

EXAMPLE 19

N⁴-(1H-benzo[d]imidazol-5-ylmethyl)-N²-(1H-indol-4-yl)pyrimidine-2,4-diamine

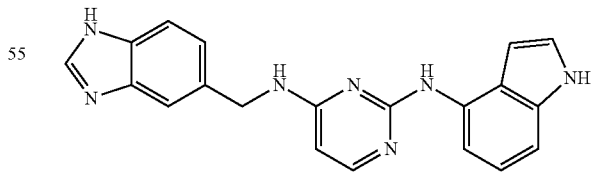

¹H NMR (500 MHz, DMSO-d₆, 75° C.) δ 12.16 (br s, 1H), 10.79 (s, 1H), 8.10 (s, 1H), 8.03 (s, 1H), 7.83 (d, 1H), 7.78 (d, 1H), 7.54 (br s, 2H), 7.44 (m, 1H), 7.20 (m, 1H), 7.18 (t, 1H), 7.00 (d, 1H), 6.94 (t, 1H), 6.72 (br s, 1H), 6.02 (d, 1H), 4.66 (d, 2H).

MS (ESI⁺) m/z 356.2 [M+H]⁺.

EXAMPLE 20

N⁴-(1H-indol-6-ylmethyl)-N²-(1H-indol-4-yl)pyrimidine-2,4-diamine

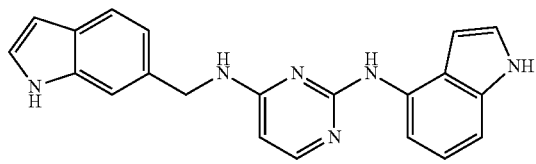 [SMILES: c1cc(Nc2nccc(NCc3ccc4cc[nH]c4c3)n2)c2cc[nH]c2c1]

¹H NMR (500 MHz, DMSO-d$_6$) δ 11.00 (s, 1H), 10.94 (s, 1H), 8.34 (s, 1H), 7.83 (m, 2H), 7.63 (br s, 1H), 7.48 (d, 1H), 7.36 (s, 1H), 7.28 (t, 1H), 7.18 (t, 1H), 7.01 (dd, 1H), 6.98-6.91 (2H), 6.80 (m, 1H), 6.37 (m, 1H), 6.00 (br s, 1H), 4.65 (br s, 2H).

MS (ESI⁺) m/z 355.3 [M+H]⁺.

EXAMPLE 21

N²-(1H-indol-5-ylmethyl)-N⁴-(1H-indol-6-ylmethyl)pyrimidine-2,4-diamine

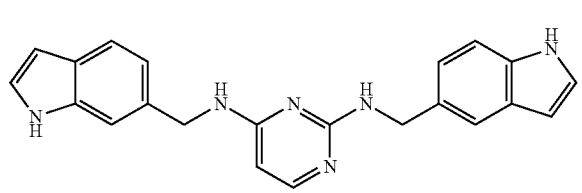 [SMILES: c1cc(NCc2ccc3cc[nH]c3c2)nc(NCc2ccc3[nH]ccc3c2)n1]

¹H NMR (500 MHz, DMSO-d$_6$) δ 10.97 (s, 1H), 10.94 (s, 1H), 7.63 (d, 1H), 7.44 (m, 2H), 7.31-7.23 (m, 5H), 7.05 (dd, 1H), 6.95 (dd, 1H), 6.79 (br s, 1H), 6.37 (m, 1H), 6.30 (br s, 1H), 5.74 (m, 1H), 4.55 (br s, 2H), 4.48 (d, 2H).

MS (ESI⁺) m/z 369.3 [M+H]⁺.

EXAMPLE 22

N²,N⁴-bis-(1H-indol-6-ylmethyl)pyrimidine-2,4-diamine

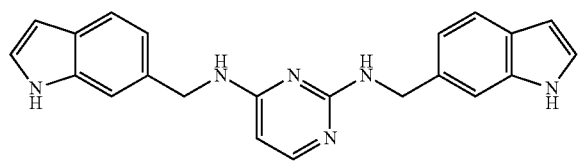 [SMILES: c1cc(NCc2ccc3cc[nH]c3c2)nc(NCc2ccc3cc[nH]c3c2)n1]

¹H NMR (500 MHz, DMSO-d$_6$) δ 10.96 (s, 1H), 10.92 (s, 1H), 7.63 (d, 1H), 7.43 (d, 1H), 7.39 (d, 1H), 7.31 (m, 3H), 7.27 (t, 1H), 7.25 (t, 1H), 6.95 (m, 2H), 6.87 (br s, 1H), 6.36 (m, 1H), 6.34 (m, 1H), 5.75 (m, 1H), 4.53 (br s, 2H), 4.51 (d, 2H).

MS (ESI⁺) m/z 369.3 [M+H]⁺.

EXAMPLE 23

N²-(1H-indol-5-ylmethyl)-N⁴-(1H-indol-4-yl)pyrimidine-2,4-diamine

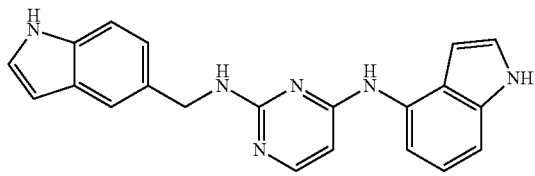 [SMILES: c1cc(Nc2ccnc(NCc3ccc4[nH]ccc4c3)n2)c2cc[nH]c2c1]

¹H-NMR (500 MHz, DMSO-d$_6$): δ 11.05 (br s, 1H), 10.94 (br s, 1H), 8.70 (s, 1H), 7.82 (d, 1H), 7.72 (br s, 1H), 7.46 (s, 1H), 7.29-7.25 (m, 3H), 7.12-7.02 (m, 3H), 6.95 (t, 1H), 6.67 (s, 1H), 6.33 (s, 1H), 6.15 (d, 1H), 4.54 (d, 2H).

MS (ESI⁺) m/z 355.3 [M+H]⁺.

EXAMPLE 24

N²-(1H-indol-5-ylmethyl)-N⁴-(2-methyl-1H-indol-5-yl)pyrimidine-2,4-diamine

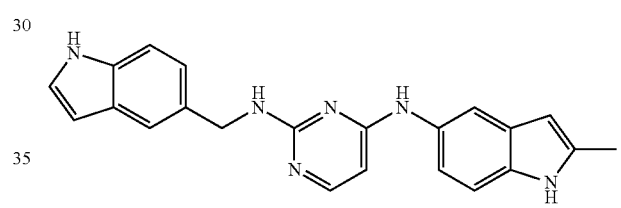

¹H-NMR (500 MHz, DMSO-d$_6$) δ 10.95 (s, 1H), 10.73 (s, 1H), 8.74 (s, 1H), 7.74 (d, 1H), 7.70 (s, 1H), 7.47 (s, 1H), 7.29 (d, 1H), 7.27-7.25 (m, 1H), 7.14 (d, 1H), 7.10 (d, 1H), 7.06 (d, 1H), 7.00 (br. s, 1H), 6.33 (s, 1H), 6.01 (s, 1H), 5.88 (d, 1H), 4.53 (d, 2H), 2.35 (s, 3H).

MS (ESI⁺) m/z 369.3 [M+H]⁺.

EXAMPLE 25

N⁴-[2-(1H-indol-3-yl)ethyl]-N²-(1H-indol-5-ylmethyl)pyrimidine-2,4-diamine

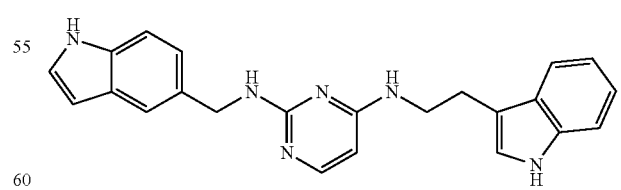

¹H NMR (500 MHz, DMSO-d$_6$) δ 10.95 (s, 1H), 10.80 (s, 1H), 7.62 (br s, 1H), 7.51 (d, 1H), 7.45 (s, 1H), 7.33-7.26 (m, 3H), 7.14 (s, 1H), 7.08-6.92 (m, 4H), 6.81 (br s, 1H), 6.31 (s, 1H), 5.69 (m, 1H), 4.51 (d, 2H), 3.52 (m, 2H), 2.90 (t, 2H).

MS (ESI⁺) m/z 383.3 [M+H]⁺.

EXAMPLE 26

3-{2-[2-(1H-indol-5-ylmethylamino)-pyrimidin-4-ylamino]ethyl}-1H-indol-5-ol

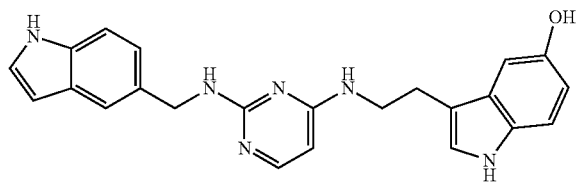 [SMILES: Oc1ccc2[nH]cc(CCNc3ccnc(NCc4ccc5[nH]ccc5c4)n3)c2c1]

$^1$H-NMR (500 MHz, DMSO-d$_6$, 75° C.) δ 10.75 (s, 1H), 10.28 (s, 1H), 8.32 (br. s, 1H), 7.62 (d, 1H), 7.48 (s, 1H), 7.28 (d, 1H), 7.24-7.23 (m, 1H), 7.12 (d, 1H), 7.09 (d, 1H), 7.02 (s, 1H), 6.87 (d, 1H), 6.62 (br. s, 1H), 6.60 (dd, 1H), 6.41 (br. s, 1H), 6.33 (s, 1H), 5.73 (d, 1H), 4.54 (d, 2H), 3.50 (q, 2H), 2.85 (t, 2H).
MS (ESI$^+$) m/z 399.2 [M+H]$^+$.

EXAMPLE 27

N$^2$-(1H-indol-5-ylmethyl)-N$^4$-[2-(5-methyl-1H-indol-3-yl)ethyl]pyrimidine-2,4-diamine

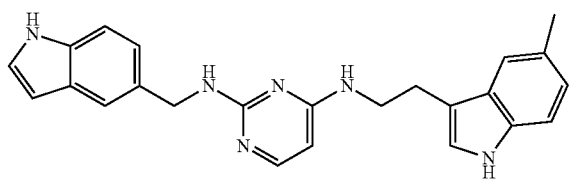 [SMILES: Cc1ccc2[nH]cc(CCNc3ccnc(NCc4ccc5[nH]ccc5c4)n3)c2c1]

$^1$H-NMR (500 MHz, DMSO-d$_6$) δ 10.93 (s, 1H), 10.65 (s, 1H), 7.62 (br. s, 1H), 7.46 (s, 1H), 7.30 (s, 1H), 7.27-7.25 (m, 2H), 7.20 (d, 1H), 7.10-7.06 (m, 2H), 6.93 (br. s, 1H), 6.87 (d, 1H), 6.77 (br. s, 1H), 6.30 (s, 1H), 5.70 (d, 1H), 4.51 (d, 2H), 3.51 (br. s, 2H), 2.88 (t, 2H), 2.33 (s, 3H).
MS (ESI$^+$) m/z 397.3 [M+H]$^+$.

EXAMPLE 28

N$^2$-(1H-indol-5-ylmethyl)-N$^4$-[2-(5-methoxy-1H-indol-3-yl)ethyl]pyrimidine-2,4-diamine

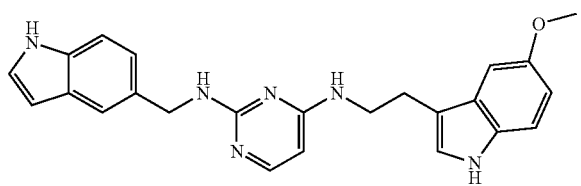 [SMILES: COc1ccc2[nH]cc(CCNc3ccnc(NCc4ccc5[nH]ccc5c4)n3)c2c1]

$^1$H-NMR (500 MHz, DMSO-d$_6$) δ 10.93 (s, 1H), 10.63 (s, 1H), 7.62 (br. s, 1H), 7.45 (s, 1H), 7.28-7.25 (m, 2H), 7.21 (d, 1H), 7.09 (s, 1H), 7.07 (d, 1H), 6.98 (d, 1H), 6.93 (br. s, 1H), 6.74 (br. s, 1H), 6.69 (dd, 1H), 6.30 (s, 1H), 5.70 (d, 1H), 4.50 (d, 2H), 3.69 (s, 3H), 3.51 (br. s, 2H), 2.88 (t, 2H).
MS (ESI) m/z 413.3 [M+H]$^+$.

EXAMPLE 29

N$^2$-(1H-indazol-5-ylmethyl)-N$^4$-(1H-indol-4-yl)pyrimidine-2,4-diamine

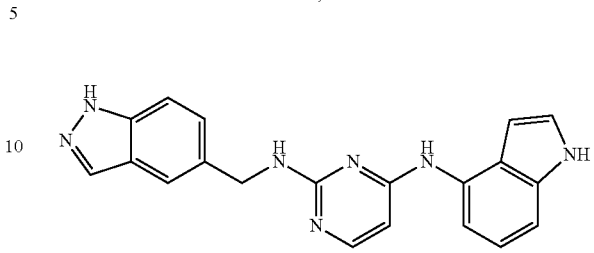

$^1$H-NMR (300 MHz, DMSO-d$_6$) δ 12.94 (br s, 1H), 11.07 (br s, 1H), 8.74 (s, 1H), 7.97 (s, 1H), 7.82 (d, 1H), 7.68 (m, 1H), 7.61 (s, 1H), 7.45 (d, 1H), 7.35 (d, 1H), 7.25 (m, 2H), 7.06 (d, 1H), 6.96 (m, 1H), 6.66 (s, 1H), 6.16 (d, 1H), 4.55 (d, 2H).
MS (ESI$^+$) m/z 356.3 [M+H]$^+$.

EXAMPLE 30

N$^2$-(1H-indol-4-yl)-N$^1$-(1H-indol-5-ylmethyl)-6-methylpyrimidine-2,4-diamine

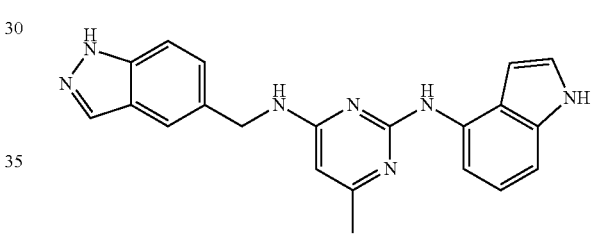

$^1$H-NMR (500 MHz, DMSO-d$_6$) δ 10.99 (s, 1H), 10.93 (s, 1H), 8.26 (s, 1H), 7.90 (br s, 1H), 7.48 (s, 1H), 7.45 (br s, 1H), 7.33 (d, 1H), 7.29 (s, 1H), 7.18 (s, 1H), 7.08 (d, 1H), 6.94 (m, 2H), 6.82 (s, 1H), 6.36 (s, 1H), 5.85 (s, 1H), 4.59 (br s, 2H), 2.12 (s, 3H).
MS (ESI$^+$) m/z 369.3 [M+H]$^+$.

EXAMPLE 31

N$^2$,N$^1$-bis(1H-indol-5-ylmethyl)-6-methylpyrimidine-2,4-diamine

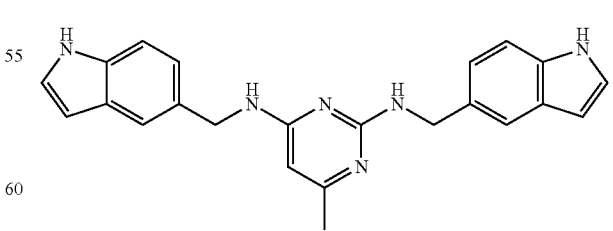

$^1$H-NMR (300 MHz, CD$_3$OD) δ 7.49 (d, 2H), 7.28 (d, 2H), 7.19 (d, 2H), 7.07 (dt, 2H), 6.35 (d, 2H), 5.71 (s, 1H), 4.62-4.60 (m, 4H), 2.11 (s, 3H).
MS (ESI$^+$) m/z 383.3 [M+H]$^+$.

EXAMPLE 32

3-{2-[4-(1H-indol-5-ylmethylamino)-6-methyl-pyrimidin-2-ylamino]-ethyl}-1H-indol-5-ol

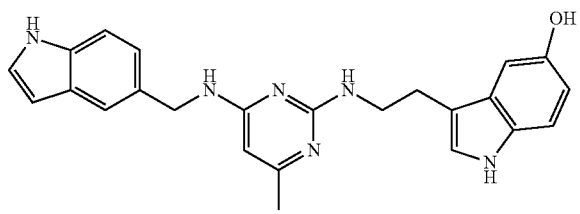 [SMILES: Cc1cc(NCc2ccc3[nH]ccc3c2)nc(NCCc2c[nH]c3ccc(O)cc23)n1]

$^1$H-NMR (300 MHz, CDCl$_3$+CD$_3$OD) δ 7.51 (s, 1H), 7.32 (d, 1H), 7.18 (d, 1H), 7.14 (d, 1H), 7.08 (d, 1H), 6.97-6.89 (m, 2H), 6.69 (dd, 1H), 6.43 (d, 1H), 5.56 (s, 1H), 4.50 (br. s, 2H), 3.65-3.56 (m, 2H), 2.93-2.87 (m, 2H), 2.09 (s, 3H).
MS (ESI$^+$) m/z 413.3 [M+H]$^+$.

EXAMPLE 33

N$^4$-(1H-indol-5-ylmethyl)-N$^2$-(2-methyl-1H-indol-5-yl)-6-trifluoromethylpyrimidine-2,4-diamine

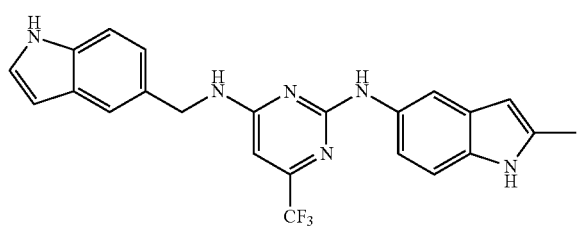 [SMILES: Cc1cc2cc(Nc3nc(NCc4ccc5[nH]ccc5c4)cc(C(F)(F)F)n3)ccc2[nH]1]

$^1$H NMR (300 MHz, DMSO-d$_6$) δ 11.01 (s, 1H), 10.67 (s, 1H), 9.14 (s, 1H), 8.11 (m, 1H), 7.76 (s, 1H), 7.48 (s, 1H), 7.33 (d, 1H), 7.29 (t, 1H), 7.20 (m, 1H), 7.09 (m, 2H), 6.34 (br. s, 1H), 6.26 (s, 1H), 5.95 (s, 1H), 4.64 (d, 2H), 2.32 (s, 3H).
MS (ESI$^+$) m/z 437.3 [M+H]$^+$.

EXAMPLE 34

N$^2$,N$^4$-Bis-(1H-indol-5-ylmethyl)-6-trifluoromethylpyrimidine-2,4-diamine

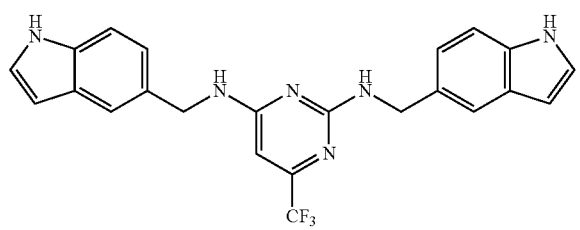 [SMILES: FC(F)(F)c1cc(NCc2ccc3[nH]ccc3c2)nc(NCc2ccc3[nH]ccc3c2)n1]

$^1$H NMR (300 MHz, CD$_3$OD) δ 7.53 (m, 1H), 7.50 (m, 1H), 7.30 (m, 2H), 7.20 (m, 2H), 7.09 (m, 2H), 6.37 (d, 2H), 6.12 (s, 1H), 4.66 (s, 4H).
MS (ESI$^+$) m/z 437.3 [M+H]$^+$.

EXAMPLE 35

N$^2$-(2-(1H-indol-3-yl)ethyl)-N$^4$-(1H-indol-5-ylmethyl)-6-trifluoromethylpyrimidine-2,4-diamine

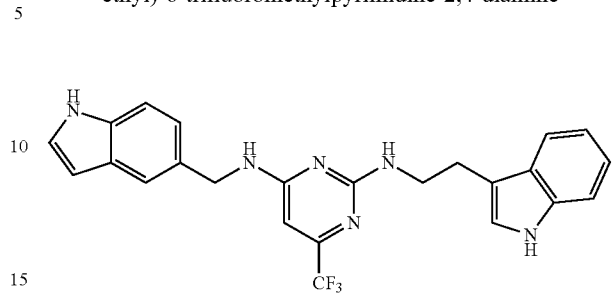

$^1$H NMR (300 MHz, CDCl$_3$) δ 8.20 (br. s, 1H), 7.95 (br. s, 1H), 7.65 (d, 1H), 7.59 (s, 1H), 7.35 (m, 2H), 7.26-7.09 (m, 4H), 7.00 (s, 1H), 6.53 (s, 1H), 6.02 (s, 1H), 5.15 (br. s, 2H), 4.63 (br. s, 2H), 3.75 (q, 2H), 3.04 (t, 2H).
MS (ESI$^+$) m/z 451.3 [M+H]$^+$.

EXAMPLE 36

N$^2$,N$^4$-bis(1H-indol-5-ylmethyl)-6-benzylpyrimidine-2,4-diamine

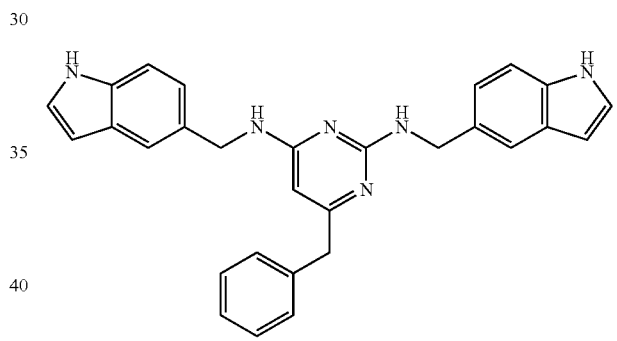

$^1$H NMR (500 MHz, DMSO-d$_6$) δ 10.97 (s, 1H), 10.94 (s, 1H), 7.45 (s, 1H), 7.41 (s, 1H), 7.28-7.25 (m, 4H), 7.22 (m, 4H), 7.18 (m, 2H), 7.07 (dd, 1H), 7.01 (dd, 1H), 6.82 (br s, 1H), 6.30 (m, 2H), 5.55 (s, 1H), 4.49 (d, 4H), 3.58 (s, 2H).
MS (ESI$^+$) m/z 459.3 [M+H]$^+$.

EXAMPLE 37

N$^4$-(1H-indazol-5-ylmethyl)-N$^2$-(1H-indol-4-yl)-6-methylpyrimidine-2,4-diamine

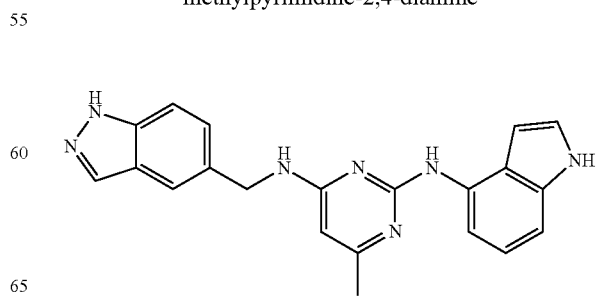

¹H-NMR (300 MHz, DMSO-d₆): δ 12.98 (s, 1H), 10.95 (s, 1H), 8.34 (s, 1H), 7.99 (s, 1H), 7.79 (m, 1H), 7.63 (s, 1H), 7.57 (br s, 1H), 7.49 (d, 1H), 7.34 (d, 1H), 7.17 (t, 1H), 6.91 (m, 2H), 6.81 (br s, 1H), 5.86 (s, 1H), 4.61 (br s, 2H), 2.13 (s, 3H).
MS (ESI⁺) m/z 370.2 [M+H]⁺.

EXAMPLE 38

N⁴-(1H-indol-5-ylmethyl)-N²-(1H-indol-4-yl)pyrimidine-2,4,5-triamine

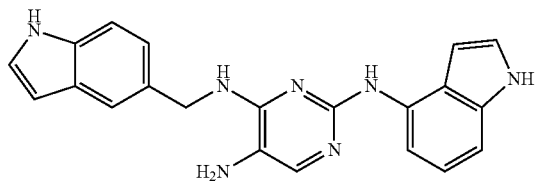 [SMILES: Nc1cnc(Nc2cccc3[nH]ccc23)nc1NCc1ccc2[nH]ccc2c1]

¹H-NMR (500 MHz, DMSO-d₆) δ 11.00 (s, 1H), 10.89 (s, 1H), 7.87 (br. s, 1H), 7.82 (s, 1H), 7.54 (s, 1H), 7.44 (s, 1H), 7.34 (d, 1H), 7.29 (s, 1H), 7.15 (s, 2H), 6.88 (s, 2H), 6.80 (s, 2H), 6.36 (s, 1H), 4.74 (s, 2H), 4.14 (s, 2H).
MS (ESI⁺) m/z 370.2 [M+H]⁺.

EXAMPLE 39

N⁴-(1H-indol-5-ylmethyl)-N²-(1H-indol-5-yl)pyrimidine-2,4,5-triamine

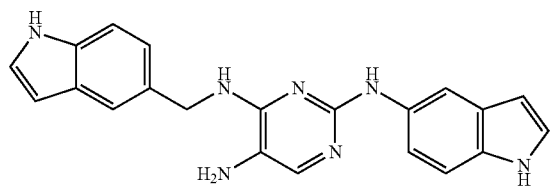 [SMILES: Nc1cnc(Nc2ccc3[nH]ccc3c2)nc1NCc1ccc2[nH]ccc2c1]

¹H-NMR (500 MHz, DMSO-d₆) δ 11.00 (s, 1H), 10.72 (s, 1H), 8.10 (s, 1H), 7.98 (s, 1H), 7.53 (s, 1H), 7.40 (s, 1H), 7.34 (d, 1H), 7.29 (t, 1H), 7.25 (dd, 1H), 7.18 (t, 1H), 7.16-7.13 (m, 2H), 6.72 (t, 1H), 6.35 (br. s, 1H), 6.22 (br. s, 1H), 4.72 (d, 2H), 3.99 (s, 2H).
MS (ESI⁺) m/z 370.2 [M+H]⁺.

EXAMPLE 40

N⁴-(1H-indol-5-ylmethyl)-N²-(1H-indol-6-yl)pyrimidine-2,4,5-triamine

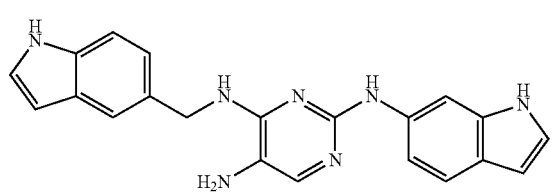 [SMILES: Nc1cnc(Nc2ccc3cc[nH]c3c2)nc1NCc1ccc2[nH]ccc2c1]

¹H-NMR (300 MHz, CD₃OD) δ 7.81-7.79 (m, 1H), 7.60-7.59 (m, 1H), 7.50 (s, 1H), 7.45 (d, 1H), 7.42 (d, 1H), 7.23-7.18 (m, 2H), 7.07 (d, 1H), 7.00 (dd, 1H), 6.40 (dd, 1H), 6.33 (dd, 1H), 4.81 (s, 2H).
MS (ESI⁺) m/z 370.3 [M+H]⁺.

EXAMPLE 41

N²,N⁴-bis(1H-indol-5-ylmethyl)pyrimidine-2,4,5-triamine

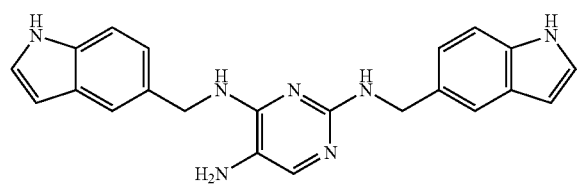

¹H-NMR (500 MHz, CD₃OD) δ 7.52 (s, 1H), 7.48 (s, 1H), 7.33 (s, 1H), 7.26 (dd, 2H), 7.17 (dd, 2H), 7.09 (dd, 1H), 7.07 (dd, 1H), 6.34 (dd, 2H), 4.71 (s, 2H), 4.55 (s, 2H).
MS (ESI⁺) m/z 384.3 [M+H]⁺.

INTERMEDIATE 42

N-(1H-indol-5-ylmethyl)-2-chloro-pyrimidin-4-amine

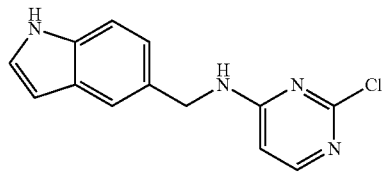 [SMILES: Clc1nccc(NCc2ccc3[nH]ccc3c2)n1]

¹H-NMR (500 MHz, CD₃OD) δ 7.81 (s, 1H), 7.51 (s, 1H), 7.34 (d, 1H), 7.21 (d, 1H), 7.09 (d, 1H), 6.40 (d, 2H), 4.61 (s, 2H).
MS (ESI⁺) m/z 259.1 [M+H]⁺.

INTERMEDIATE 43

N-(1H-indol-5-ylmethyl)-4-chloro-pyrimidin-2-amine

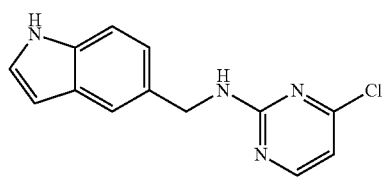 [SMILES: Clc1ccnc(NCc2ccc3[nH]ccc3c2)n1]

¹H-NMR (500 MHz, CD₃OD) δ 8.13 (d, 1H), 7.51 (s, 1H), 7.32 (d, 1H), 7.19 (d, 1H), 7.10 (dd, 1H), 6.59 (d, 1H), 6.38 (d, 1H), 4.61 (s, 2H).
MS (ESI⁺) m/z 259.1 [M+H]⁺.

INTERMEDIATE 44

N-(2-methyl-1H-indol-5-ylmethyl)-2-chloro-pyrimidin-4-amine

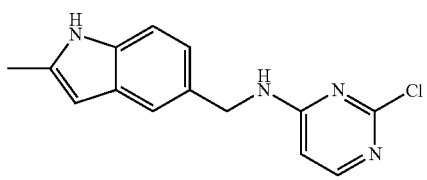 [SMILES: Cc1cc2cc(CNc3ccnc(Cl)n3)ccc2[nH]1]

$^1$H-NMR (500 MHz, DMSO-d$_6$) δ 10.86 (s, 1H), 8.27 (br s, 1H), 7.90 (br s, 1H), 7.33 (s, 1H), 7.21 (d, 1H), 6.95 (d, 1H), 6.49 (d, 1H), 6.07 (s, 1H), 4.51 (br s, 2H), 2.36 (s, 3H).

MS (ESI$^+$) m/z 273.1 [M+H]$^+$.

INTERMEDIATE 45

N-(1H-indazol-5-ylmethyl)-2-chloro-pyrimidin-4-amine

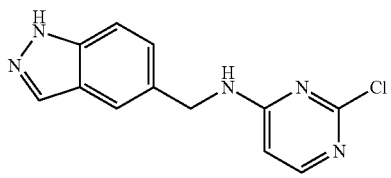 [SMILES: Clc1nccc(NCc2ccc3[nH]ncc3c2)n1]

$^1$H-NMR (500 MHz, DMSO-d$_6$) δ 13.03 (s, 1H), 8.37 (br s, 1H), 8.04 (br s, 1H), 7.92 (m, 1H), 7.67 (s, 1H), 7.51 (d, 1H), 7.31 (d, 1H), 6.51 (d, 1H), 4.58 (br s, 2H).

INTERMEDIATE 46

N-(1H-benzo[d]imidazol-5-ylmethyl)-2-chloro-pyrimidin-4-amine

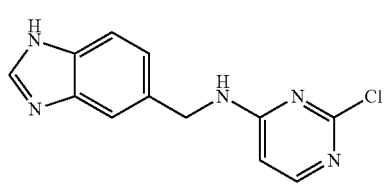 [SMILES: Clc1nccc(NCc2ccc3[nH]cnc3c2)n1]

$^1$H NMR (500 MHz, DMSO-d$_6$, 75° C.) δ 12.22 (br s, 1H), 8.21 (br s, 1H), 8.13 (s, 1H), 7.93 (d, 1H), 7.53 (m, 2H), 7.17 (d, 1H), 6.51 (d, 1H), 4.59 (d, 2H).

MS (ESI$^+$) m/z 260.2 [M+H]$^+$.

INTERMEDIATE 47

N-(1H-indol-6-ylmethyl)-2-chloro-pyrimidin-4-amine

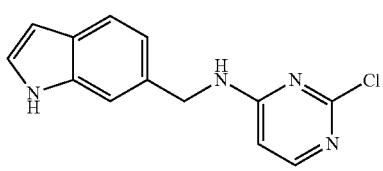 [SMILES: Clc1nccc(NCc2ccc3cc[nH]c3c2)n1]

$^1$H NMR (500 MHz, DMSO-d$_6$, 75° C.) δ 10.86 (br s, 1H), 8.18 (br s, 1H), 7.92 (d, 1H), 7.49 (d, 1H), 7.34 (s, 1H), 7.27 (t, 1H), 6.97 (d, 1H), 6.50 (d, 1H), 6.39 (br s, 1H), 4.56 (d, 2H).

MS (ESI$^+$) m/z 259.1 [M+H]$^+$.

INTERMEDIATE 48

N-(1H-indol-6-ylmethyl)-4-chloro-pyrimidin-2-amine

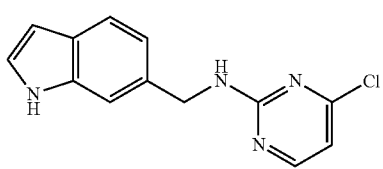 [SMILES: Clc1ccnc(NCc2ccc3cc[nH]c3c2)n1]

$^1$H NMR (500 MHz, DMSO-d$_6$) δ 10.99 (br s, 1H), 8.23-8.20 (m, 2H), 7.45 (d, 1H), 7.30 (s, 1H), 7.28 (t, 1H), 6.95 (d, 1H), 6.66 (d, 1H), 6.36 (br s, 1H), 4.57 (br s, 2H).

MS (ESI$^+$) m/z 259.0 [M+H]$^+$.

INTERMEDIATE 49

N-(1H-indol-5-ylmethyl)-2-chloro-6-methyl-pyrimidin-4-amine

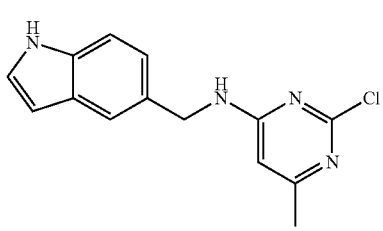 [SMILES: Cc1cc(NCc2ccc3[nH]ccc3c2)nc(Cl)n1]

$^1$H-NMR (300 MHz, CDCl$_3$) δ 8.23 (br. s, 1H), 7.58 (s, 1H), 7.40 (d, 1H), 7.25 (s, 1H), 7.13 (d, 1H), 6.55-6.53 (m, 1H), 6.11 (s, 1H), 5.45 (br s, 1H), 4.58 (br. s, 2H), 2.32 (s, 3H).

MS (ESI$^+$) m/z 273.1 [M+H]$^+$.

INTERMEDIATE 50

N-(1H-indol-5-ylmethyl)-4-chloro-6-methyl-pyrimidin-2-amine

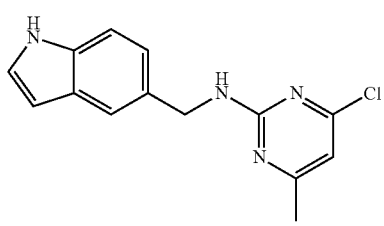 [SMILES: Cc1cc(Cl)nc(NCc2ccc3[nH]ccc3c2)n1]

$^1$H-NMR (500 MHz, DMSO-d$_6$) δ 11.04 (s, 1H), 8.16 (br s, 1H), 7.46 (s, 1H), 7.34 (d, 1H), 7.32 (m, 1H), 7.04 (d, 1H), 6.38 (br s, 1H), 6.32 (br s, 1H), 4.53 (br s, 2H), 2.17 (s, 3H).

INTERMEDIATE 51

N-(1H-indazol-5-ylmethyl)-2-chloro-6-methyl-pyrimidin-4-amine

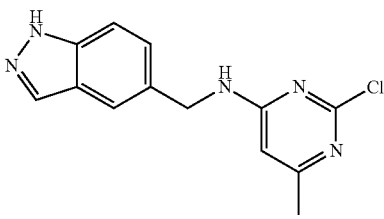 [SMILES: Cc1cc(NCc2ccc3[nH]ncc3c2)nc(Cl)n1]

$^1$H-NMR (500 MHz, CDCl$_3$) δ 10.37 (m, 1H), 8.05 (d, 1H), 7.71 (d, 1H), 7.48 (m, 1H), 7.38 (m, 1H), 6.50 (s, 1H), 5.62 (br s, 1H), 4.73 (d, 2H), 2.32 (s, 3H).

INTERMEDIATE 52

N-(1H-indol-5-ylmethyl)-2-chloro-6-trifluoromethyl-pyrimidin-4-amine

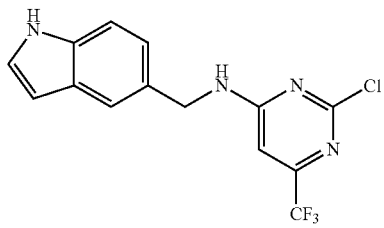 [SMILES: FC(F)(F)c1cc(NCc2ccc3[nH]ccc3c2)nc(Cl)n1]

$^1$H NMR (300 MHz, CDCl$_3$, 75° C.) δ 8.16 (br s, 1H), 7.60 (s, 1H), 7.41 (d, 1H), 7.24 (m, 1H), 7.15 (d, 1H), 6.58 (m, 2H), 5.62 (br s, 1H), 4.69 (d, 2H).

MS (ESI$^+$) m/z 327.1 [M+H]$^+$.

INTERMEDIATE 53

N-(1H-indol-5-ylmethyl)-6-benzyl-2-chloro-pyrimidin-4-amine

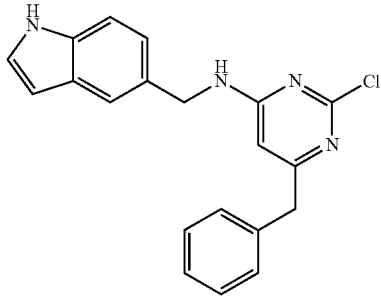 [SMILES: Clc1nc(Cc2ccccc2)cc(NCc2ccc3[nH]ccc3c2)n1]

$^1$H NMR (500 MHz, DMSO-d$_6$, 75° C.) δ 10.86 (br s, 1H), 8.04 (br s, 1H), 7.45 (s, 1H), 7.34 (d, 1H), 7.31-7.28 (m, 3H), 7.24-7.20 (m, 3H), 7.03 (d, 1H), 6.38 (m, 1H), 6.28 (s, 1H), 4.50 (d, 2H), 3.80 (s, 2H).

MS (ESI$^+$) m/z 349.2 [M+H]$^+$.

INTERMEDIATE 54

N-(1H-indol-5-ylmethyl)-2-chloro-5-nitro-pyrimidin-4-amine

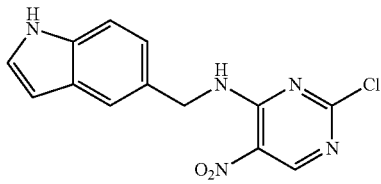 [SMILES: O=[N+]([O-])c1cnc(Cl)nc1NCc1ccc2[nH]ccc2c1]

$^1$H-NMR (500 MHz, DMSO-d$_6$) δ 11.06 (s, 1H), 9.53 (t, 1H), 9.03 (s, 1H), 7.54 (s, 1H), 7.34 (d, 1H), 7.32 (t, 1H), 7.13 (dd, 1H), 6.38 (br. s, 1H), 4.80 (d, 2H).

MS (ESI$^+$) m/z 304.1 [M+H]$^+$.

INTERMEDIATE 55

N-(1H-indol-4-yl)-2-chloro-pyrimidin-4-amine

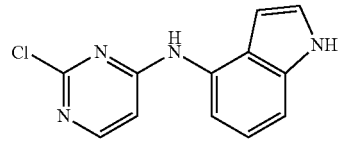 [SMILES: Clc1nccc(Nc2cccc3[nH]ccc23)n1]

$^1$H-NMR (500 MHz, CDCl$_3$) δ 8.39 (br s, 1H), 8.07 (d, 1H), 7.36 (d, 1H), 7.26 (m, 1H), 7.23 (t, 1H), 7.18 (br s, 1H), 7.10 (d, 1H), 6.52 (d, 1H), 6.44 (br s, 1H).

MS (ESI$^+$) m/z 245.1 [M+H]$^+$.

INTERMEDIATE 56

N-[2-(1H-indol-3-yl)ethyl]-2-chloro-pyrimidin-4-amine

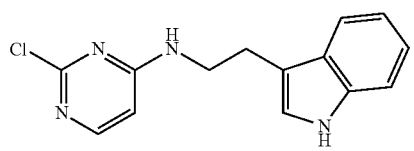 [SMILES: Clc1nccc(NCCc2c[nH]c3ccccc23)n1]

¹H NMR (500 MHz, DMSO-d₆, 75° C.) δ 10.66 (br s, 1H), 7.90 (d, 1H), 7.79 (br s, 1H), 7.58 (d, 1H), 7.35 (d, 1H), 7.15 (s, 1H), 7.07 (t, 1H), 6.99 (t, 1H), 6.44 (d, 1H), 3.56 (m, 2H), 2.96 (t, 2H).

MS (ESI⁺) m/z 273.2 [M+H]⁺.

INTERMEDIATE 57

N⁴-(1H-indol-5-ylmethyl)-N²-(1H-indol-4-yl)-5-nitropyrimidine-2,4-diamine

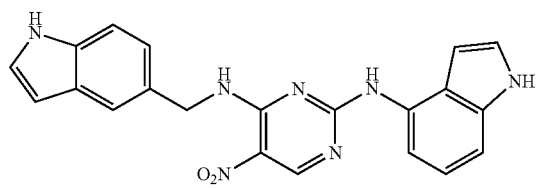

¹H-NMR (500 MHz, DMSO-d₆) δ 11.13 (s, 1H), 10.99 (s, 1H), 10.09 (s, 1H), 9.20 (s, 1H), 8.98 (s, 1H), 7.44 (br. s, 1H), 7.29-7.25 (m, 4H), 7.21 (d, 1H), 7.04-6.99 (m, 2H), 6.68 (br. s, 1H), 6.26 (br. s, 1H), 4.70 (s, 2H).

MS (ESI⁺) m/z 400.3 [M+H]⁺.

INTERMEDIATE 58

N⁴-(1H-indol-5-ylmethyl)-N²-(1H-indol-5-yl)-5-nitropyrimidine-2,4-diamine

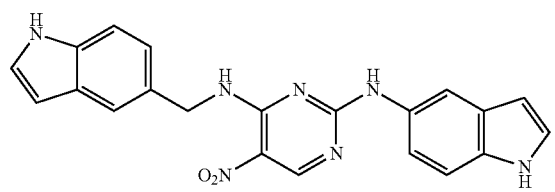

¹H-NMR (500 MHz, DMSO-d₆, 75° C.) δ 10.85 (s, 2H), 9.97 (br. s, 1H), 9.05 (br. s, 1H), 9.20 (s, 1H), 7.91 (s, 1H), 7.51 (s, 1H), 7.33-7.30 (m, 3H), 7.28 (dt, 2H), 7.12 (d, 1H), 6.33 (d, 2H), 4.85 (d, 2H).

MS (ESI⁺) m/z 400.2 [M+H]⁺.

INTERMEDIATE 59

N⁴-(1H-indol-5-ylmethyl)-N²-(1H-indol-6-yl)-5-nitropyrimidine-2,4-diamine

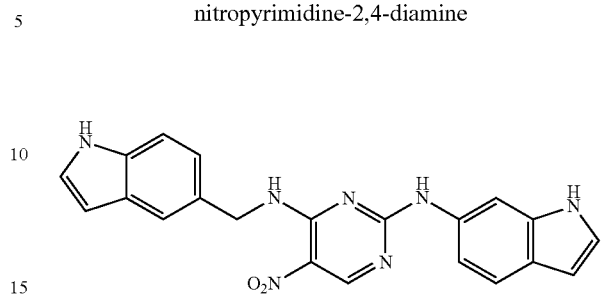

¹H-NMR (500 MHz, DMSO-d₆, 75° C.) δ 10.86 (br. s, 2H), 10.07 (br. s, 1H), 8.97 (br. s, 1H), 8.95 (s, 1H), 7.94 (s, 1H), 7.54 (s, 1H), 7.44 (d, 1H), 7.35-7.31 (m, 2H), 7.28-7.25 (m, 2H), 7.15 (d, 1H), 6.38 (br. s, 1H), 6.31 (br. s, 1H), 4.88 (d, 2H).

MS (ESI⁺) m/z 400.3 [M+H]⁺.

INTERMEDIATE 60

N²,N⁴-bis(1H-indol-5-ylmethyl)-5-nitropyrimidine-2,4-diamine

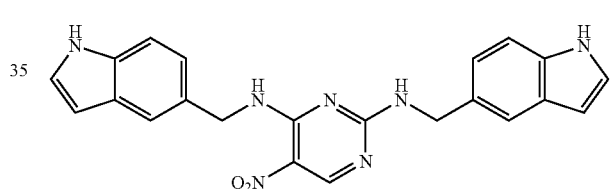

¹H-NMR (500 MHz, DMSO-d₆, 105° C.) δ 10.76 (m, 2H), 8.86 (br. s, 2H), 8.35 (br. s, 1H), 7.52 (d, 2H), 7.32 (t, 2H), 7.26 (m, 2H), 7.10 (dd, 2H), 6.35 (s, 2H), 4.83 (d, 2H), 4.66 (d, 2H).

MS (ESI⁺) m/z 414.3 [M+H]⁺.

INTERMEDIATE 61

N-(2-methyl-1H-indol-5-yl)-2-chloro-pyrimidin-4-amine

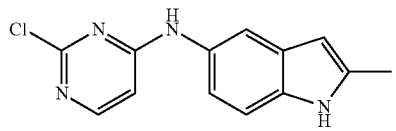 [SMILES: Cc1cc2cc(Nc3ccnc(Cl)n3)ccc2[nH]1]

¹H-NMR (500 MHz, DMSO-d₆, 75° C.) δ 10.76 (s, 1H), 9.54 (s, 1H), 8.01 (d, 1H), 7.47 (s, 1H), 7.26 (d, 1H), 7.01 (d, 1H), 6.56 (d, 1H), 6.11 (s, 1H), 2.39 (s, 3H).

MS (ESI⁺) m/z 259.1 [M+H]⁺.

EXAMPLE 62

5-{[2-(1H-indol-5-ylmethylamino)pyrimidin-4-ylamino]methyl}indolin-2-one

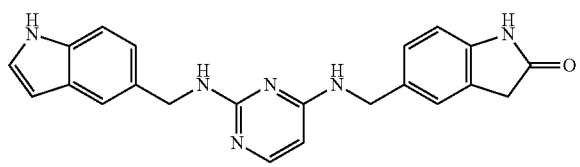 [SMILES: O=C1Cc2cc(CNc3ccnc(NCc4ccc5[nH]ccc5c4)n3)ccc2N1]

¹H-NMR (500 MHz, CD₃OD) δ 7.59 (d, 1H), 7.43 (s, 1H), 7.26 (d, 1H), 7.17 (d, 1H), 7.09 (d, 1H), 7.07 (br s, 1H), 7.03 (d, 1H), 6.73 (d, 1H), 6.32 (d, 1H), 5.77 (d, 1H), 4.58 (s, 2H), 4.48 (s, 2H), 3.31 (s, 2H).

MS (ESI⁺) m/z 385.3 [M+H]⁺.

EXAMPLE 63

N⁴-(2-methyl-1H-indol-5-yl)-N²-(2-methyl-1H-indol-5-ylmethyl)pyrimidine-2,4-diamine

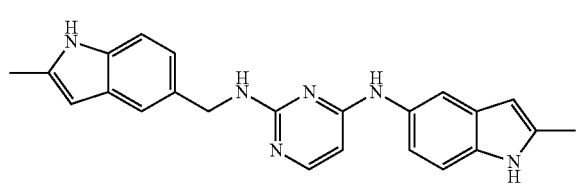

¹H-NMR (500 MHz, DMSO-d₆) δ 10.73 (d, 2H), 8.72 (s, 1H), 7.74 (d, 1H), 7.70 (s, 1H), 7.32 (s, 1H), 7.17-7.12 (m, 2H), 7.07 (d, 1H), 6.99 (d, 1H), 6.95 (br s, 1H), 6.01 (m, 2H), 6.88 (d, 1H), 5.51 (d, 2H), 2.34 (d, 6H).

MS (ESI⁺) m/z 383.3 [M+H]⁺.

EXAMPLE 64

N²-[2-(5-methoxy-1H-indol-3-yl)ethyl]-N⁴-(2-methyl-1H-indol-5-ylmethyl)pyrimidine-2,4-diamine

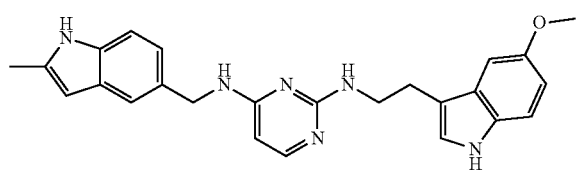

¹H-NMR (500 MHz, DMSO-d₆, 75° C.) δ 10.60 (s, 1H), 10.42 (s, 1H), 7.66 (d, 1H), 7.34 (s, 1H), 7.22 (d, 1H), 7.18 (d, 1H), 7.07 (dd, 2H), 6.98 (m, 2H), 6.71 (dd, 1H), 6.05 (br s, 1H), 6.03 (s, 1H), 5.77 (d, 1H), 4.50 (d, 2H), 3.73 (s, 3H), 3.53 (q, 2H), 2.91 (t, 2H), 2.36 (s, 3H).

MS (ESI⁺) m/z 427.5 [M+H]⁺.

EXAMPLE 65

N²-(1H-indazol-5-ylmethyl)-N⁴-(2-methyl-1H-indol-5-yl)pyrimidine-2,4-diamine

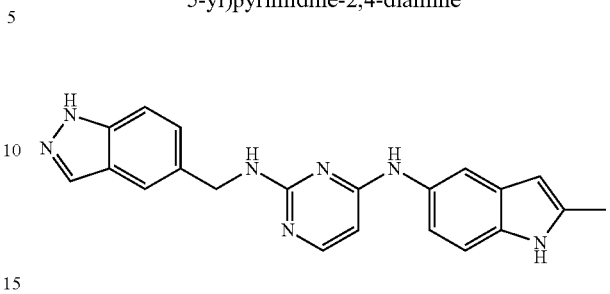

¹H-NMR (500 MHz, DMSO-d₆) δ 12.93 (s, 1H), 10.74 (s, 1H), 8.78 (s, 1H), 7.95 (br s, 1H), 7.75 (d, 1H), 7.66 (br s, 1H), 7.62 (s, 1H), 7.45 (d, 1H), 7.35 (d, 1H), 7.13 (d, 2H), 7.05 (m, 1H), 5.99 (br s, 1H), 5.90 (d, 1H), 4.55 (d, 2H), 2.35 (s, 3H).

MS (ESI⁺) m/z 370.3 [M+H]⁺.

EXAMPLE 66

N⁴-(1H-indazol-5-ylmethyl)-N²-[2-(5-methoxy-1H-indol-3-yl)ethyl]pyrimidine-2,4-diamine

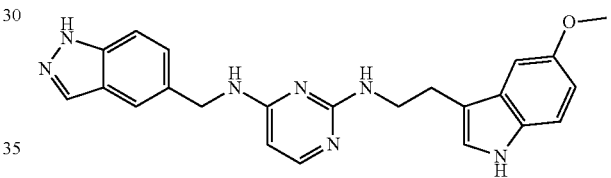

¹H-NMR (500 MHz, DMSO-d₆) δ 12.97 (s, 1H), 10.60 (s, 1H), 7.97 (br s, 1H), 7.68-7.62 (m, 2H), 7.46 (d, 1H), 7.37 (br s, 1H), 7.32 (d, 1H), 7.20 (d, 1H), 7.08 (s, 1H), 7.04 (br s, 1H), 6.69 (dd, 1H), 6.41 (br s, 1H), 5.76 (br s, 1H), 4.56 (br s, 2H), 3.71 (s, 3H), 3.47 (q, 2H), 2.87 (t, 2H).

MS (ESI⁺) m/z 414.4 [M+H]⁺.

EXAMPLE 67

N²-(1H-benzo[d]imidazol-5-ylmethyl)-N⁴-(2-methyl-1H-indol-5-yl)pyrimidine-2,4-diamine

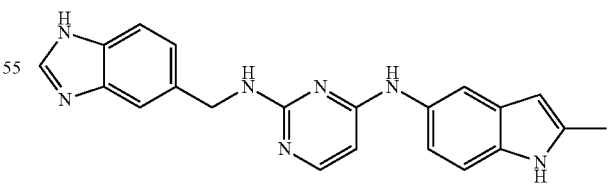

¹H-NMR (500 MHz, DMSO-d₆, 75° C.) δ 12.1 (br s, 1H), 10.60 (s, 1H), 8.78 (s, 1H), 8.09 (s, 1H), 7.76 (d, 1H), 7.61 (s, 1H), 7.55 (s, 1H), 7.50 (d, 1H), 7.21-7.15 (m, 2H), 7.08 (d, 1H), 7.01 (br s, 1H), 6.01 (s, 1H), 5.96 (d, 1H), 4.62 (d, 2H), 2.36 (s, 3H).

MS (ESI⁺) m/z 370.4 [M+H]⁺.

EXAMPLE 68

N⁴-(1H-benzo[d]imidazol-5-ylmethyl)-N²-(1H-indol-5-ylmethyl)pyrimidine-2,4-diamine

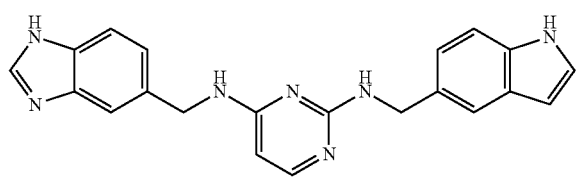 [SMILES: c1cc(NCc2ccc3[nH]cnc3c2)nc(NCc2ccc3[nH]ccc3c2)n1]

¹H-NMR (500 MHz, DMSO-d$_6$) δ 12.14 (br s, 1H), 10.76 (s, 1H), 8.10 (s, 1H), 7.66 (d, 1H), 7.60-7.40 (m, 3H), 7.26 (d, 1H), 7.24 (t, 1H), 7.15 (br s, 2H), 7.06 (d, 1H), 6.47 (br s, 1H), 6.32 (s, 1H), 5.78 (d, 1H), 4.58 (d, 2H), 4.51 (d, 2H).
MS (ESI⁺) m/z 370.3 [M+H]⁺.

EXAMPLE 69

N⁴-(1H-benzo[d]imidazol-5-ylmethyl)-N²-[2-(5-methoxy-1H-indol-3-yl)ethyl]pyrimidine-2,4-diamine

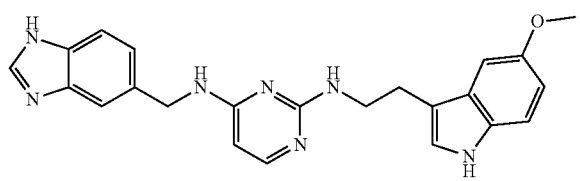 [SMILES: COc1ccc2[nH]cc(CCNc3nccc(NCc4ccc5[nH]cnc5c4)n3)c2c1]

¹H-NMR (500 MHz, CD$_3$OD) δ 8.10 (s, 1H), 7.60-7.52 (m, 3H), 7.27 (d, 1H), 7.18 (d, 1H), 6.97 (m, 2H), 6.71 (dd, 1H), 5.81 (d, 1H), 4.66 (br s, 2H), 3.72 (s, 3H), 3.60 (t, 2H), 2.93 (t, 2H).
MS (ESI⁺) m/z 414.3 [M+H]⁺.

EXAMPLE 70

N²-(1H-indol-6-ylmethyl)-N⁴-(2-methyl-1H-indol-5-yl)pyrimidine-2,4-diamine

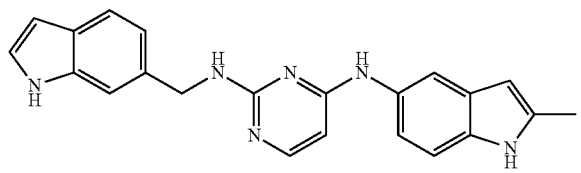 [SMILES: Cc1cc2cc(Nc3ccnc(NCc4ccc5cc[nH]c5c4)n3)ccc2[nH]1]

¹H-NMR (500 MHz, CD$_3$OD) δ 7.68 (d, 1H), 7.49 (d, 2H), 7.36 (s, 1H), 7.19 (s, 1H), 7.16 (d, 1H), 7.02 (dd, 2H), 6.38 (dd, 1H), 6.03 (s, 1H), 5.95 (d, 1H), 4.64 (s, 2H), 2.38 (s, 3H).
MS (ESI⁺) m/z 369.4 [M+H]⁺.

EXAMPLE 71

N⁴-(1H-indol-6-ylmethyl)-N²-[2-(5-methoxy-1H-indol-3-yl)ethyl]pyrimidine-2,4-diamine

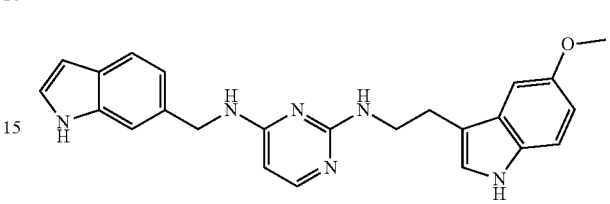

¹H-NMR (500 MHz, DMSO-d$_6$) δ 10.98 (s, 1H), 10.59 (s, 1H), 7.66 (br s, 1H), 7.44 (d, 1H), 7.32 (br s, 2H), 7.27 (t, 1H), 7.20 (d, 1H), 7.07 (m, 2H), 6.96 (d, 1H), 6.69 (dd, 1H), 6.36 (m, 2H), 5.76 (br s, 1H), 4.56 (br s, 2H), 3.71 (s, 3H), 3.48 (q, 2H), 2.87 (t, 2H).
MS (ESI⁺) m/z 413.3 [M+H]⁺.

EXAMPLE 72

N⁴-(1H-indol-5-ylmethyl)-N²-{2-[5-(benzyloxy)-1H-indol-3-yl]ethyl}pyrimidine-2,4-diamine

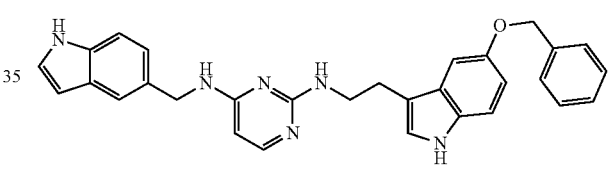

¹H-NMR (500 MHz, DMSO-d$_6$, 75° C.) δ 10.80 (s, 1H), 10.45 (s, 1H), 7.66 (d, 1H), 7.48 (s, 1H), 7.44 (m, 2H), 7.36 (t, 2H), 7.32-7.29 (m, 2H), 7.25 (t, 1H), 7.23 (d, 1H), 7.18 (d, 1H), 7.09-7.06 (m, 2H), 7.03 (br s, 1H), 6.80 (dd, 1H), 6.34 (br s, 1H), 6.06 (br s, 1H), 5.78 (d, 1H), 5.06 (s, 2H), 4.53 (d, 2H), 3.53 (q, 2H), 2.90 (t, 2H).
MS (ESI⁺) m/z 489.4 [M+H]⁺.

EXAMPLE 73

N⁴-(1H-indol-5-ylmethyl)-N²-{2-[5-(2-morpholinoethoxy)-1H-indol-3-yl]ethyl}pyrimidine-2,4-diamine

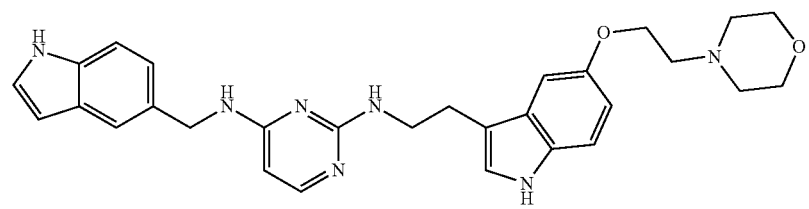 [SMILES: c1cc(NCc2ccc3[nH]ccc3c2)nc(NCCc2c[nH]c3ccc(OCCN4CCOCC4)cc23)n1]

¹H-NMR (500 MHz, DMSO-d₆, 75° C.) δ 10.80 (s, 1H), 10.42 (s, 1H), 7.66 (d, 1H), 7.49 (s, 1H), 7.32 (d, 1H), 7.26 (t, 1H), 7.21 (d, 1H), 7.10-7.07 (m, 3H), 7.02 (m, 1H), 6.72 (dd, 1H), 6.35 (br s, 1H), 6.05 (t, 1H), 5.78 (d, 1H), 4.54 (d, 2H), 4.06 (t, 2H), 3.58 (m, 4H), 3.53 (q, 2H), 2.91 (t, 2H), 2.67 (t, 2H), 2.51-2.46 (m, 4H).
MS (ESI⁺) m/z 512.4 [M+H]⁺.

EXAMPLE 74

$N^4$-(1H-indol-5-ylmethyl)-$N^2$-{2-[5-(2-methoxy-ethoxy)-1H-indol-3-yl]ethyl}pyrimidine-2,4-diamine

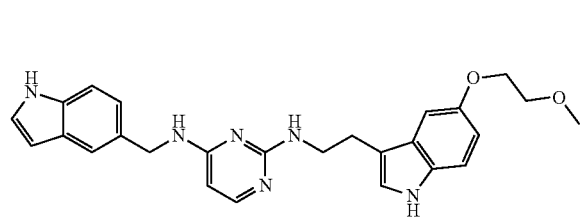 [SMILES: COCCOc1ccc2[nH]cc(CCNc3nccc(NCc4ccc5[nH]ccc5c4)n3)c2c1]

¹H-NMR (500 MHz, DMSO-d₆, 75° C.) δ 10.81 (s, 1H), 10.43 (s, 1H), 7.66 (d, 1H), 7.49 (s, 1H), 7.32 (d, 1H), 7.26 (t, 1H), 7.22 (d, 1H), 7.08 (m, 3H), 7.01 (m, 1H), 6.72 (dd, 1H), 6.35 (br s, 1H), 6.06 (m, 1H), 5.78 (d, 1H), 4.54 (d, 2H), 4.06 (t, 2H), 3.63 (t, 2H), 3.53 (q, 2H), 3.32 (s, 3H), 2.90 (t, 2H).
MS (ESI⁺) m/z 457.5 [M+H]⁺.

EXAMPLE 75

$N^4$-(1H-indol-5-ylmethyl)-$N^2$-(1-methyl-1H-indol-4-yl)pyrimidine-2,4-diamine

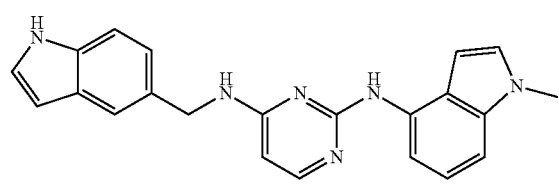 [SMILES: Cn1ccc2c(Nc3nccc(NCc4ccc5[nH]ccc5c4)n3)cccc21]

¹H-NMR (500 MHz, DMSO-d₆) δ 11.00 (s, 1H), 8.37 (s, 1H), 7.91 (d, 1H), 7.81 (d, 1H), 7.59 (br s, 1H), 7.50 (s, 1H), 7.33 (d, 1H), 7.30 (t, 1H), 7.17 (d, 1H), 7.09 (dd, 1H), 7.02-6.98 (m, 2H), 6.80 (d, 1H), 6.36 (br s, 1H), 5.99 (d, 1H), 4.61 (br s, 2H), 3.73 (s, 3H).
MS (ESI⁺) m/z 369.4 [M+H]⁺.

EXAMPLE 76

$N^4$-(1H-indol-5-ylmethyl)-$N^2$-(1H-indazol-4-yl)pyrimidine-2,4-diamine

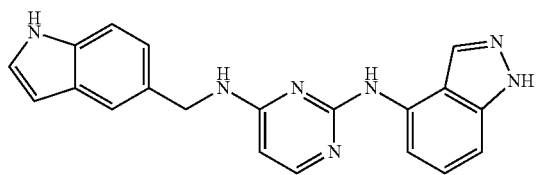 [SMILES: c1cc(Nc2nccc(NCc3ccc4[nH]ccc4c3)n2)c2cn[nH]c2c1]

¹H-NMR (500 MHz, DMSO-d₆, 75° C.) δ 12.68 (s, 1H), 10.83 (s, 1H), 8.74 (s, 1H), 8.40 (s, 1H), 7.89 (d, 1H), 7.86 (d, 1H), 7.51 (s, 1H), 7.42 (m, 1H), 7.35 (d, 1H), 7.27 (m, 1H), 7.18 (t, 1H), 7.10 (d, 1H), 7.05 (d, 1H), 6.37 (m, 1H), 6.07 (d, 1H), 4.62 (d, 2H).
MS (ESI⁺) m/z 356.3 [M+H]⁺.

EXAMPLE 77

$N^4$-(1H-indol-5-ylmethyl)-$N^2$-[(1-methyl-1H-indol-5-yl)methyl]pyrimidine-2,4-diamine

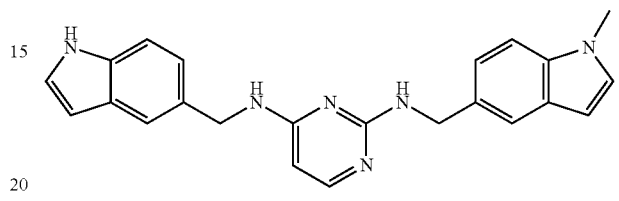

¹H-NMR (500 MHz, DMSO-d₆) δ 10.99 (s, 1H), 7.61 (d, 1H), 7.45 (m, 2H), 7.29-7.24 (m, 5H), 7.12 (dd, 1H), 7.03 (d, 1H), 6.83 (br s, 1H), 6.33 (br s, 1H), 6.31 (m, 1H), 5.73 (d, 1H), 4.50 (m, 4H), 3.74 (s, 3H).
MS (ESI⁺) m/z 383.4 [M+H]⁺.

EXAMPLE 78

$N^4$-(1H-indol-5-ylmethyl)-$N^2$-(1H-indol-4-ylmethyl)pyrimidine-2,4-diamine

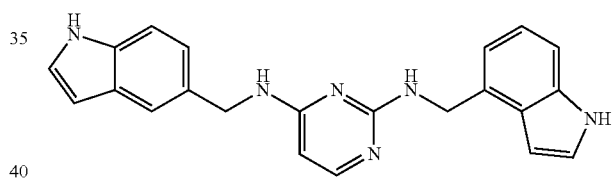

¹H-NMR (500 MHz, DMSO-d₆) δ 10.99 (d, 2H), 7.61 (m, 1H), 7.43 (br s, 1H), 7.29-7.23 (m, 5H), 7.02 (d, 1H), 6.96 (t, 1H), 6.92 (d, 1H), 6.78 (br s, 1H), 6.58 (s, 1H), 6.34 (s, 1H), 5.74 (m, 1H), 4.70 (d, 2H), 4.49 (br s, 2H).
MS (ESI⁺) m/z 369.3 [M+H]⁺.

EXAMPLE 79

$N^4$-(1H-indol-5-ylmethyl)-$N^2$-[(9H-carbazol-3-yl)methyl]pyrimidine-2,4-diamine

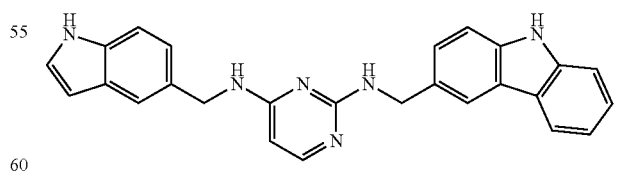

¹H-NMR (500 MHz, DMSO-d₆) δ 11.15 (s, 1H), 11.0 (s, 1H), 8.03 (s, 1H), 7.98 (br s, 1H), 7.63 (br d, 1H), 7.45 (m, 2H), 7.38-7.27 (m, 6H), 7.10 (t, 1H), 7.05 (d, 1H), 6.92 (br s, 1H), 6.32 (br s, 1H), 5.75 (br d, 1H), 4.59 (d, 2H), 4.54 (br s, 2H).
MS (ESI⁺) m/z 419.3 [M+H]⁺.

EXAMPLE 80

N²-(1H-indol-5-ylmethyl)-N⁴-[(9H-carbazol-3-yl)methyl]pyrimidine-2,4-diamine

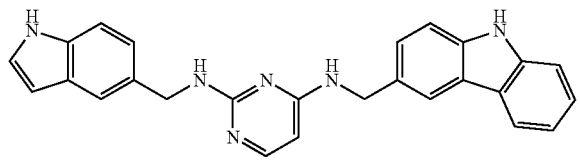 [SMILES: c1ccc2c(c1)[nH]c1ccc(CNc3ccnc(NCc4ccc5[nH]ccc5c4)n3)cc12]

¹H-NMR (500 MHz, DMSO-d$_6$) δ 11.17 (s, 1H), 10.94 (s, 1H), 8.04 (s, 1H), 8.01 (br s, 1H), 7.63 (d, 1H), 7.46-7.44 (m, 2H), 7.41-7.32 (m, 4H), 7.28-7.25 (m, 2H), 7.11 (t, 1H), 7.08 (d, 1H), 6.84 (br s, 1H), 6.31 (s, 1H), 5.75 (d, 1H), 4.60 (br s, 2H), 4.51 (d, 2H).
MS (ESI⁺) m/z 419.3 [M+H]⁺.

EXAMPLE 81

Methyl 4-[4-(1H-indol-5-ylmethylamino)pyrimidin-2-ylamino]-1H-indole-6-carboxylate

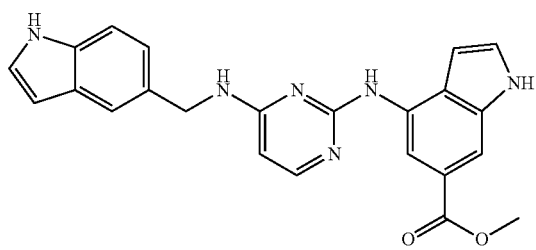 [SMILES: COC(=O)c1cc(Nc2nccc(NCc3ccc4[nH]ccc4c3)n2)c2cc[nH]c2c1]

¹H-NMR (500 MHz, DMSO-d$_6$) δ 11.38 (s, 1H), 11.00 (s, 1H), 8.85 (br s, 1H), 8.66 (s, 1H), 7.84 (d, 1H), 7.70 (s, 1H), 7.57 (br s, 1H), 7.52 (s, 1H), 7.45 (t, 1H), 7.32 (d, 1H), 7.29 (t, 1H), 7.11 (dd, 1H), 6.99 (br s, 1H), 6.34 (br s, 1H), 6.02 (d, 1H), 4.73 (br s, 2H), 3.70 (s, 3H).
MS (ESI⁺) m/z 413.3 [M+H]⁺.

EXAMPLE 82

N²-(1H-indol-5-ylmethyl)-N⁴-(1H-indol-5-yl)pyrimidine-2,4-diamine

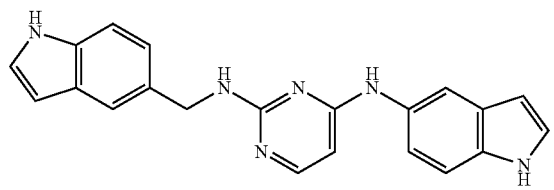 [SMILES: c1cc(Nc2ccc3[nH]ccc3c2)nc(NCc2ccc3[nH]ccc3c2)n1]

¹H-NMR (500 MHz, DMSO-d$_6$, 75° C.) δ 10.76 (s, 2H), 8.59 (s, 1H), 7.81 (s, 1H), 7.77 (d, 1H), 7.50 (s, 1H), 7.30 (m, 2H), 7.25 (m, 2H), 7.18 (dd, 1H), 7.11 (d, 1H), 6.67 (br s, 1H), 6.33 (br s, 2H), 5.93 (d, 1H), 4.57 (d, 2H).
MS (ESI⁺) m/z 355.2 [M+H]⁺.

EXAMPLE 83

N²-(1H-indol-5-ylmethyl)-6-methyl-N⁴-(2-methyl-1H-indol-5-yl)pyrimidine-2,4-diamine

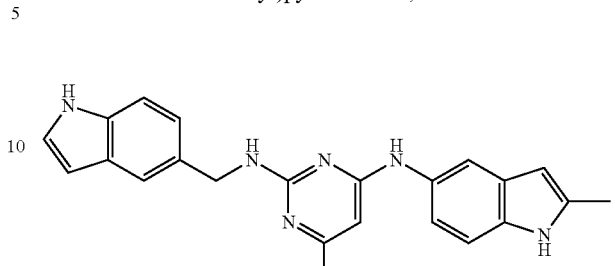

¹H-NMR (500 MHz, DMSO-d$_6$, 75° C.) δ 10.77 (s, 1H), 10.55 (s, 1H), 8.37 (s, 1H), 7.60 (s, 1H), 7.50 (s, 1H), 7.31 (d, 1H), 7.25 (t, 1H), 7.16-7.10 (m, 2H), 7.06 (d, 1H), 6.53 (br s, 1H), 6.34 (s, 1H), 6.02 (s, 1H), 5.78 (s, 1H), 4.57 (d, 2H), 2.36 (s, 3H), 2.07 (s, 3H).
MS (ESI⁺) m/z 383.4 [M+H]⁺.

EXAMPLE 84

N⁴-(1H-indol-5-ylmethyl)-N²-[2-(5-methoxy-1H-indol-3-yl)ethyl]-6-methylpyrimidine-2,4-diamine

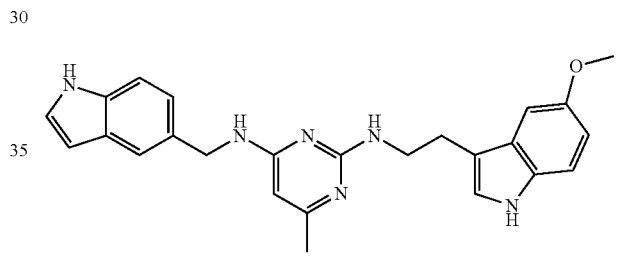

¹H-NMR (500 MHz, DMSO-d$_6$) δ 10.98 (s, 1H), 10.60 (s, 1H), 7.46 (s, 1H), 7.31-7.27 (m, 2H), 7.21 (d, 1H), 7.14-7.03 (m, 4H), 6.69 (dd, 1H), 6.33 (s, 1H), 6.29 (br s, 1H), 5.62 (s, 1H), 4.53 (br s, 2H), 3.70 (s, 3H), 3.48 (q, 2H), 2.88 (t, 2H), 2.01 (s, 3H).
MS (ESI⁺) m/z 427.4 [M+H]⁺.

EXAMPLE 85

N⁴-(1H-indol-5-ylmethyl)-6-benzyl-N²-[2-(5-methoxy-1H-indol-3-yl)ethyl]pyrimidine-2,4-diamine

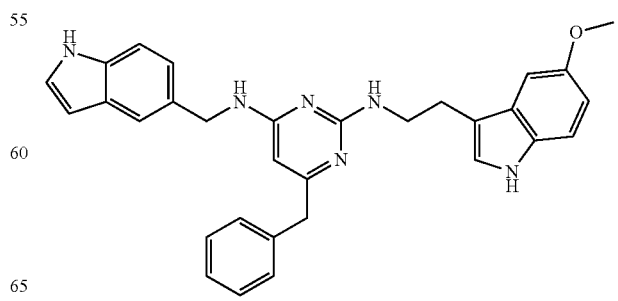

¹H-NMR (500 MHz, DMSO-d₆) δ 10.79 (s, 1H), 10.42 (s, 1H), 7.45 (s, 1H), 7.30-7.16 (m, 8H), 7.07-7.03 (m, 3H), 6.94 (m, 1H), 6.71 (dd, 1H), 6.33 (s, 1H), 6.07 (br s, 1H), 5.62 (s, 1H), 4.51 (d, 2H), 3.71 (s, 3H), 3.63 (s, 2H), 3.54 (q, 2H), 2.91 (t, 2H).
MS (ESI) m/z 503.4 [M+H]⁺.

EXAMPLE 86

N⁴-(1H-indol-5-ylmethyl)-N²-[2-(5-methoxy-7-methyl-1H-indol-3-yl)ethyl]pyrimidine-2,4-diamine

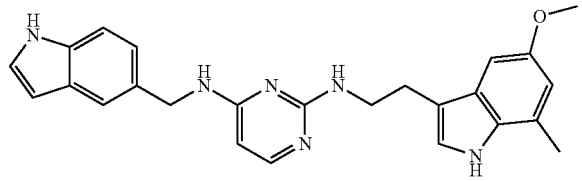 [SMILES: COc1cc(C)c2[nH]cc(CCNc3nccc(NCc4ccc5[nH]ccc5c4)n3)c2c1]

¹H-NMR (500 MHz, DMSO-d₆, 75° C.) δ 10.81 (s, 1H), 10.38 (s, 1H), 7.66 (d, 1H), 7.48 (s, 1H), 7.32 (d, 1H), 7.26 (t, 1H), 7.08-7.06 (m, 2H), 7.02 (m, 1H), 6.89 (s, 1 H), 6.53 (s, 1H), 6.35 (s, 1H), 6.05 (m, 1H), 5.77 (d, 1H), 4.54 (d, 2H), 3.71 (s, 3H), 3.53 (q, 2H), 2.90 (t, 2H), 2.40 (s, 3H).
MS (ESI⁺) m/z 427.4 [M+H]⁺.

EXAMPLE 87

N⁴-(1H-indol-5-ylmethyl)-N²-[2-(5-ethoxy-1H-indol-3-yl)ethyl]pyrimidine-2,4-diamine

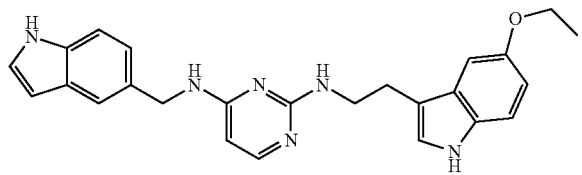 [SMILES: CCOc1ccc2[nH]cc(CCNc3nccc(NCc4ccc5[nH]ccc5c4)n3)c2c1]

¹H-NMR (500 MHz, DMSO-d₆, 75° C.) δ 10.81 (s, 1H), 10.41 (s, 1H), 7.66 (d, 1H), 7.49 (s, 1H), 7.32 (d, 1H), 7.26 (t, 1H), 7.21 (d, 1H), 7.09-7.06 (m, 3H), 7.01 (m, 1H), 6.70 (dd, 1H), 6.35 (m, 1H), 6.06 (m, 1H), 5.78 (d, 1H), 4.54 (d, 2H), 3.99 (q, 2H), 3.53 (q, 2H), 2.90 (t, 2H), 1.30 (t, 3H).
MS (ESI) m/z 427.3 [M+H]⁺.

EXAMPLE 88

N⁴-(1H-indol-5-ylmethyl)-N²-{2-[5-(trifluoromethoxy)-1H-indol-3-yl]ethyl}pyrimidine-2,4-diamine

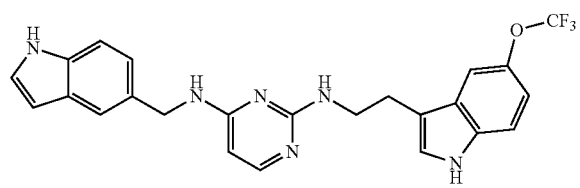 [SMILES: FC(F)(F)Oc1ccc2[nH]cc(CCNc3nccc(NCc4ccc5[nH]ccc5c4)n3)c2c1]

¹H-NMR (500 MHz, DMSO-d₆, 75° C.) δ 10.90 (s, 1H), 10.80 (s, 1H), 7.66 (d, 1H), 7.52 (s, 1H), 7.48 (s, 1H), 7.41 (d, 1H), 7.31 (d, 1H), 7.26 (m, 2H), 7.07 (d, 1H), 7.01-7.00 (m, 2H), 6.34 (s, 1H), 6.12 (t, 1H), 5.78 (d, 1H), 4.53 (d, 2H), 3.53 (q, 2H), 2.93 (t, 2H).
MS (ESI⁺) m/z 467.2 [M+H]⁺.

EXAMPLE 89

N⁴-(1H-indol-5-ylmethyl)-N²-[2-(5-fluoro-1H-indol-3-yl)ethyl]pyrimidine-2,4-diamine

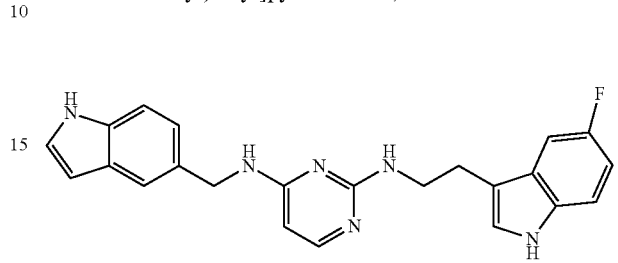

¹H-NMR (500 MHz, DMSO-d₆, 75° C.) δ 10.81 (s, 1H), 10.71 (s, 1H), 7.66 (d, 1H), 7.48 (s, 1H), 7.33-7.28 (m, 3H), 7.26 (t, 1H), 7.20 (s, 1H), 7.07 (d, 1H), 7.03 (br s, 1H), 6.87 (m, 1H), 6.35 (s, 1H), 6.09 (br s, 1H), 5.78 (d, 1H), 4.54 (d, 2H), 3.52 (q, 2H), 2.90 (t, 2H).
MS (ESI⁺) m/z 401.3 [M+H]⁺.

EXAMPLE 90

N⁴-(1H-indol-5-ylmethyl)-N²-[2-(6-methoxy-1H-indol-3-yl)ethyl]pyrimidine-2,4-diamine

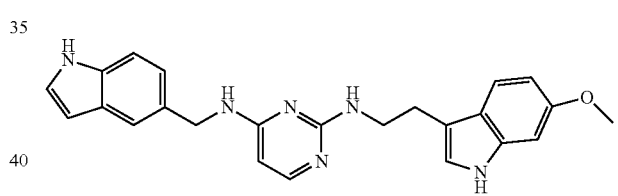

¹H-NMR (500 MHz, DMSO-d₆, 75° C.) δ 10.81 (s, 1H), 10.37 (s, 1H), 7.66 (d, 1H), 7.49 (s, 1H), 7.41 (d, 1H), 7.32 (d, 1H), 7.26 (t, 1H), 7.08 (d, 1H), 7.03 (m, 1H), 6.97 (s, 1H), 6.85 (d, 1H), 6.60 (dd, 1H), 6.35 (s, 1H), 6.05 (m, 1H), 5.78 (d, 1H), 4.55 (d, 2H), 3.75 (s, 3H), 3.53 (q, 2H), 2.89 (t, 2H).
MS (ESI⁺) m/z 413.3 [M+H]⁺.

EXAMPLE 91

N⁴-(1H-indol-5-ylmethyl)-N²-[2-(7-methoxy-1H-indol-3-yl)ethyl]pyrimidine-2,4-diamine

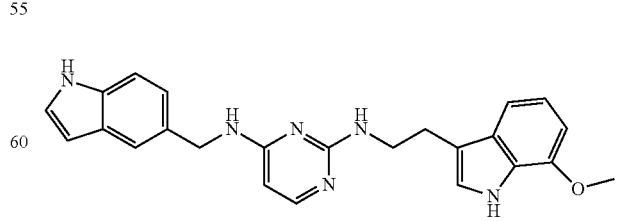

¹H-NMR (500 MHz, DMSO-d₆, 75° C.) δ 10.81 (s, 1H), 10.62 (s, 1H), 7.66 (d, 1H), 7.49 (s, 1H), 7.32 (d, 1H), 7.26 (t, 1H), 7.16 (d, 1H), 7.08 (d, 1H), 7.04-7.00 (m, 2H), 6.87 (t,

1H), 6.63 (d, 1H), 6.36 (s, 1H), 6.06 (br s, 1H), 5.77 (d, 1H), 4.54 (d, 2H), 3.90 (s, 3H), 3.53 (q, 2H), 2.92 (t, 2H).
MS (ESI⁺) m/z 413.3 [M+H]⁺.

EXAMPLE 92

N²-(1H-indol-5-ylmethyl)-N⁴-(1,2-dimethyl-1H-indol-5-yl)pyrimidine-2,4-diamine

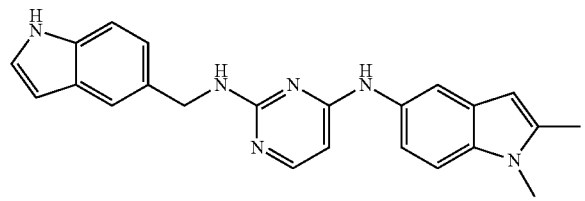 [SMILES: Cc1cc2cc(Nc3ccnc(NCc4ccc5[nH]ccc5c4)n3)ccc2n1C]

¹H-NMR (500 MHz, DMSO-d₆, 75° C.) δ 10.77 (s, 1H), 8.57 (s, 1H), 7.77 (d, 1H), 7.69 (d, 1H), 7.50 (d, 1H), 7.31 (d, 1H), 7.24 (dd, 1H), 7.23 (d, 1H), 7.16 (dd, 1H), 7.11 (d, 1H), 6.65 (br s, 1H), 6.34 (s, 1H), 6.10 (s, 1H), 5.91 (s, 1H), 4.57 (d, 2H), 3.63 (s, 3H), 2.38 (s, 3H).
MS (ESI⁺) m/z 383.2 [M+H]⁺.

EXAMPLE 93 methyl 5-[2-(1H-indol-5-ylmethylamino)pyrimidin-4-ylamino]-1H-indole-2-carboxylate

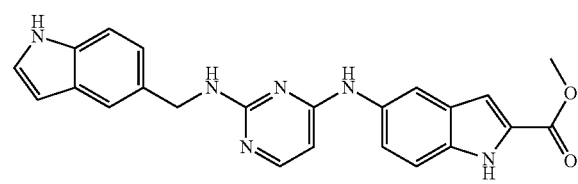 [SMILES: COC(=O)c1cc2cc(Nc3ccnc(NCc4ccc5[nH]ccc5c4)n3)ccc2[nH]1]

¹H-NMR (500 MHz, CD₃OD) δ 7.87 (s, 1H), 7.74 (d, 1H), 7.52 (s, 1H), 7.36-7.30 (m, 3H), 7.18 (d, 1H), 7.13 (dd, 1H), 7.06 (s, 1H), 6.38 (d, 1H), 5.98 (d, 1H), 4.62 (s, 2H), 3.90 (s, 3H).
MS (ESI⁺) m/z 413.3 [M+H]⁺.

EXAMPLE 94

N²-(1H-indol-5-ylmethyl)-N⁴-(2,3-dimethyl-1H-indol-5-yl)pyrimidine-2,4-diamine

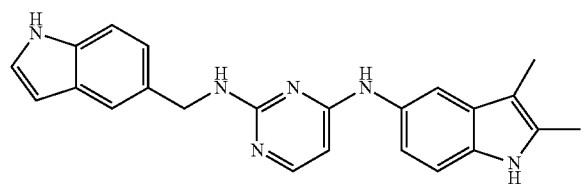 [SMILES: Cc1[nH]c2ccc(Nc3ccnc(NCc4ccc5[nH]ccc5c4)n3)cc2c1C]

¹H-NMR (500 MHz, DMSO-d₆, 75° C.) δ 10.77 (br s, 1H), 10.31 (s, 1H), 8.55 (s, 1H), 7.76 (d, 1H), 7.64 (s, 1H), 7.48 (s, 1H), 7.29 (d, 1H), 7.24 (t, 1H), 7.13-7.07 (m, 3H), 6.57 (br s, 1H), 6.33 (s, 1H), 5.91 (d, 1H), 4.60 (d, 2H), 2.28 (s, 3H), 2.07 (s, 3H).
MS (ESI⁺) m/z 383.3 [M+H]⁺.

EXAMPLE 95

N²-(1H-indol-5-ylmethyl)-N⁴-(1H-benzo[d]imidazol-5-yl)pyrimidine-2,4-diamine

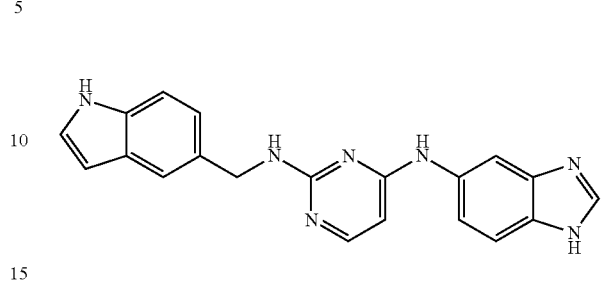

¹H-NMR (500 MHz, DMSO-d₆, 75° C.) δ 12.07 (br s, 1H), 10.77 (br s, 1H), 8.83 (s, 1H), 8.05 (s, 1H), 7.98 (s, 1H), 7.82 (d, 1H), 7.51 (s, 1H), 7.45 (m, 1H), 7.34 (d, 1H), 7.30 (d, 1H), 7.24 (t, 1H), 7.12 (d, 1H), 6.71 (br s, 1H), 6.32 (s, 1H), 5.99 (d, 1H), 4.59 (d, 2H).
MS (ESI⁺) m/z 356.1 [M+H]⁺.

EXAMPLE 96

N²-(1H-indol-5-ylmethyl)-N⁴-(2-methyl-1H-benzo[d]imidazol-5-yl)pyrimidine-2,4-diamine

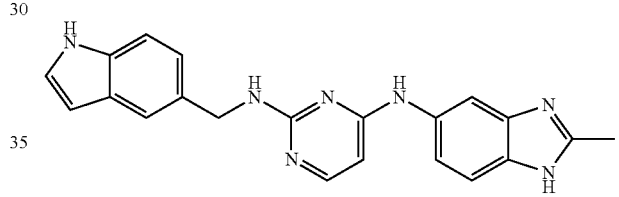

¹H-NMR (500 MHz, DMSO-d₆, 75° C.) δ 11.78 (br s, 1H), 10.77 (s, 1H), 8.76 (br s, 1H), 7.82-7.79 (m, 2H), 7.51 (s, 1H), 7.34-7.23 (m, 4H), 7.12 (dd, 1H), 6.66 (br s, 1H), 6.33 (s, 1H), 5.97 (d, 1H), 4.58 (d, 2H), 2.44 (s, 3H).
MS (ESI⁺) m/z 370.2 [M+H]⁺.

EXAMPLE 97

N⁴-(1H-indol-5-ylmethyl)-N²-(1H-indazol-4-yl)-6-methylpyrimidine-2,4-diamine

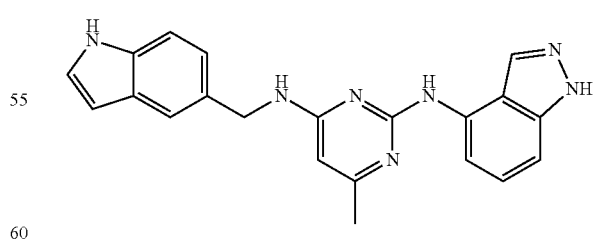

¹H-NMR (500 MHz, DMSO-d₆, 75° C.) δ 12.66 (s, 1H), 10.82 (s, 1H), 8.70 (br s, 1H), 8.43 (s, 1H), 7.94 (d, 1H), 7.50 (s, 1H), 7.34 (d, 1H), 7.29 (br s, 1H), 7.27 (dd, 1H), 7.16 (dd, 1H), 7.09 (d, 1H), 7.02 (d, 1H), 6.36 (s, 1H), 5.94 (s, 1H), 4.61 (d, 2H), 2.16 (s, 3H).
MS (ESI⁺) m/z 370.2 [M+H]⁺.

EXAMPLE 98

N²-[2-(5-methoxy-1H-indol-3-yl)ethyl]-6-methyl-N⁴-[(2-methyl-1H-indol-5-yl)methyl]pyrimidine-2,4-diamine

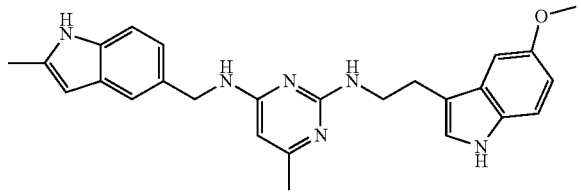

¹H-NMR (500 MHz, DMSO-d₆, 75° C.) δ 10.59 (s, 1H), 10.43 (s, 1H), 7.33 (s, 1H), 7.22 (d, 1H), 7.17 (d, 1H), 7.08 (d, 1H), 7.06 (s, 1H), 6.97 (d, 1H), 6.85 (br s, 1H), 6.71 (dd, 1H), 6.02 (s, 1H), 5.99 (br s, 1H), 5.65 (s, 1H), 4.50 (d, 2H), 3.73 (s, 3H), 3.53 (dd, 2H), 2.91 (t, 2H), 2.36 (s, 3H), 2.03 (s, 3H).
MS (ESI⁺) m/z 441.4 [M+H]⁺.

EXAMPLE 99

N⁴-(1H-indazol-5-ylmethyl)-N²-[2-(5-methoxy-1H-indol-3-yl)ethyl]-6-methylpyrimidine-2,4-diamine

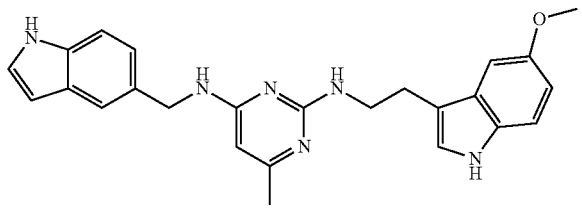 [SMILES: COc1ccc2[nH]cc(CCNc3nc(C)cc(NCc4ccc5[nH]ccc5c4)n3)c2c1]

¹H-NMR (500 MHz, DMSO-d₆, 75° C.) δ 12.79 (s, 1H), 10.43 (s, 1H), 7.94 (s, 1H), 7.65 (s, 1H), 7.45 (d, 1H), 7.33 (d, 1H), 7.21 (d, 1H), 7.07 (d, 1H), 7.04 (s, 1H), 7.02 (br s, 1H), 6.71 (d, 1H), 6.03 (br s, 1H), 5.66 (s, 1H), 4.57 (d, 2H), 3.74 (s, 3H), 3.52 (dd, 2H), 2.89 (t, 2H), 2.04 (s, 3H).
MS (ESI⁺) m/z 428.4 [M+H]⁺.

EXAMPLE 100

N⁴-(1H-indol-5-ylmethyl)-N²-[2-(5-methoxy-2-methyl-1H-indol-3-yl)ethyl]-6-methylpyrimidine-2,4-diamine

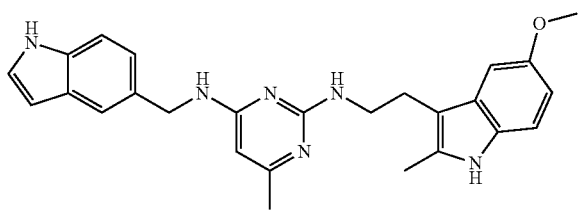 [SMILES: COc1ccc2[nH]c(C)c(CCNc3nc(C)cc(NCc4ccc5[nH]ccc5c4)n3)c2c1]

¹H-NMR (500 MHz, DMSO-d₆, 75° C.) δ 10.84 (s, 1H), 10.33 (s, 1H), 7.56 (br s, 1H), 7.48 (s, 1H), 7.33 (d, 1H), 7.27 (dd, 1H), 7.11 (d, 1H), 7.06 (d, 1H), 6.97 (d, 1H), 6.62 (dd, 1H), 6.42 (br s, 1H), 6.36 (s, 1H), 5.76 (s, 1H), 4.58 (d, 2H), 3.70 (s, 3H), 3.47 (dd, 2H), 2.87 (t, 2H), 2.29 (s, 3H), 2.09 (s, 3H).
MS (ESI⁺) m/z 441.3 [M+H]⁺.

EXAMPLE 101

N⁴-(1H-indol-5-ylmethyl)-N²-[2-(4-methoxy-1H-indol-3-yl)ethyl]pyrimidine-2,4-diamine

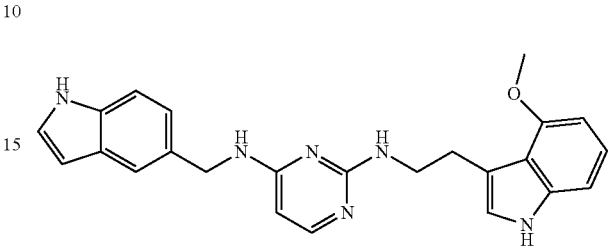

¹H-NMR (500 MHz, DMSO-d₆, 75° C.) δ 10.80 (s, 1H), 10.56 (s, 1H), 7.63 (d, 1H), 7.48 (s, 1H), 7.31 (d, 1H), 7.26 (dd, 1H), 7.07 (dd, 1H), 7.05-6.91 (m, 4H), 6.43 (dd, 1H), 6.34 (s, 1H), 5.94 (m, 1H), 5.75 (d, 1H), 4.51 (d, 2H), 3.85 (s, 3H), 3.54 (dd, 2H), 3.06 (t, 2H).
MS (ESI) m/z 413.3 [M+H]⁺.

EXAMPLE 102

4-[4-(1H-indol-5-ylmethylamino)pyrimidin-2-ylamino]-1H-indole-6-carboxylic acid

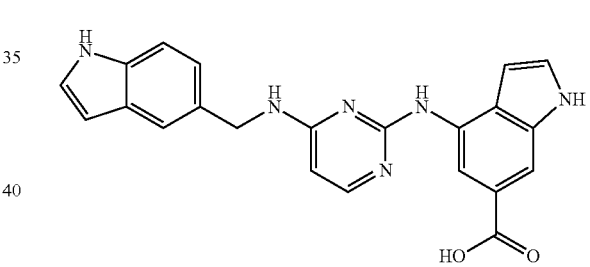

¹H-NMR (500 MHz, DMSO-d₆, 75° C.) δ 12.12 (br s, 1H), 11.42 (s, 1H), 10.87 (s, 1H), 9.70 (br s, 1H), 8.69 (br s, 1H), 8.38 (s, 1H), 7.91 (s, 1H), 7.82 (d, 1H), 7.52 (s, 1H), 7.47 (s, 1H), 7.32 (d, 1H), 7.28 (dd, 1H), 7.06 (d, 1H), 6.77 (s, 1H), 6.34 (s, 1H), 6.22 (d, 1H), 4.69 (d, 2H).
MS (ESI⁺) m/z 399.3 [M+H]⁺.

EXAMPLE 103

N²-(1H-indol-4-yl)-6-methyl-N⁴-[(2-methyl-1H-indol-5-yl)methyl]pyrimidine-2,4-diamine

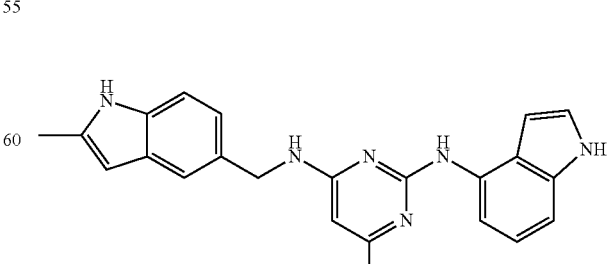

¹H-NMR (500 MHz, DMSO-d₆, 75° C.) δ 10.78 (s, 1H), 10.61 (s, 1H), 7.93 (s, 1H), 7.89 (d, 1H), 7.35 (s, 1H), 7.19 (d, 1H), 7.17 (dd, 1H), 7.00-6.94 (m, 3H), 6.74 (s, 1H), 6.16 (s, 1H), 6.05 (s, 1H), 5.87 (s, 1H), 4.56 (d, 2H), 2.36 (s, 3H), 2.14 (s, 3H).
MS (ESI) m/z 383.3 [M+H]⁺.

EXAMPLE 104

{5-[2-(1H-indol-5-ylmethylamino)pyrimidin-4-ylamino]-1H-indol-2-yl}methanol

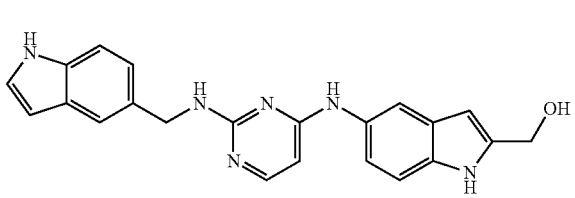 [SMILES: OCc1cc2cc(Nc3ccnc(NCc4ccc5[nH]ccc5c4)n3)ccc2[nH]1]

¹H-NMR (500 MHz, DMSO-d₆, 75° C.) δ 10.77 (s, 1H), 10.64 (s, 1H), 8.55 (s, 1H), 7.76 (d, 1H), 7.72 (d, 1H), 7.50 (s, 1H), 7.31 (d, 1H), 7.26-7.22 (m, 2H), 7.15-7.10 (m, 2H), 6.64 (br m, 1H), 6.35 (s, 1H), 6.19 (s, 1H), 5.91 (d, 1H), 4.95 (t, 1H), 4.61-4.56 (m, 4H).
MS (ESI) m/z 385.3 [M+H]⁺.

EXAMPLE 105

N²-(1H-indol-5-ylmethyl)-N¹-methyl-N¹-(2-methyl-1H-indol-5-yl)pyrimidine-2,4-diamine

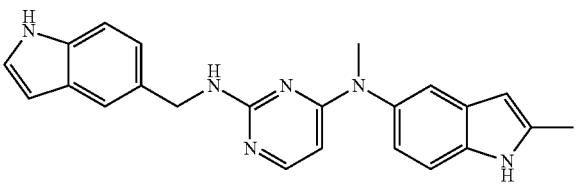 [SMILES: Cc1cc2cc(N(C)c3ccnc(NCc4ccc5[nH]ccc5c4)n3)ccc2[nH]1]

¹H-NMR (500 MHz, DMSO-d₆) δ 11.03 (s, 1H), 10.96 (s, 1H), 7.57 (d, 1H), 7.48 (s, 1H), 7.33-7.27 (m, 3H), 7.25 (s, 1H), 7.10 (d, 1H), 6.99 (br s, 1H), 6.83 (d, 1H), 6.36 (s, 1H), 6.12 (s, 1H), 5.35 (d, 1H), 4.52 (d, 2H), 3.38 (s, 3H), 2.38 (s, 3H).
MS (ESI⁺) m/z 383.2 [M+H]⁺.

EXAMPLE 106

N²-(1H-indol-5-ylmethyl)-N¹-(1,2-dimethyl-1H-indol-5-yl)-N¹-methylpyrimidine-2,4-diamine

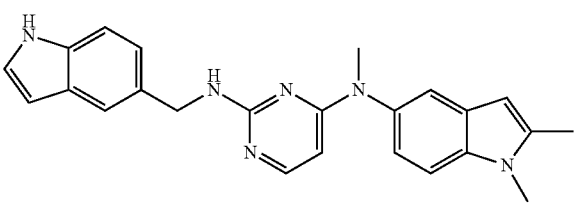 [SMILES: Cc1cc2cc(N(C)c3ccnc(NCc4ccc5[nH]ccc5c4)n3)ccc2n1C]

¹H-NMR (500 MHz, CD₃OD) δ 7.54 (s, 1H), 7.49 (d, 1H), 7.35 (d, 1H), 7.34 (d, 1H), 7.28 (d, 1H), 7.20 (d, 1H), 7.14 (d, 1H), 6.92 (dd, 1H), 6.40 (d, 1H), 6.22 (s, 1H), 5.49 (d, 1H), 4.63 (s, 2H), 3.70 (s, 3H), 3.45 (s, 3H), 2.43 (s, 3H).
MS (ESI) m/z 397.3 [M+H]⁺.

EXAMPLE 107

N⁴-(1H-indol-5-ylmethyl)-N²-[2-(5-methoxy-1-methyl-1H-indol-3-yl)ethyl]pyrimidine-2,4-diamine

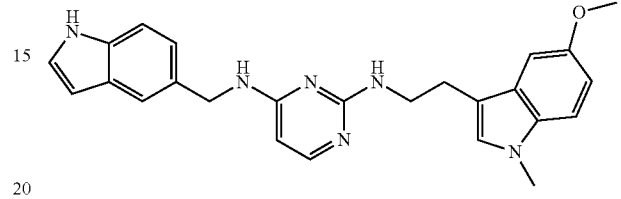

¹H-NMR (500 MHz, DMSO-d₆, 75° C.) δ 10.83 (s, 1H), 7.66 (d, 1H), 7.49 (s, 1H), 7.42 (br s, 1H), 7.33 (d, 1H), 7.27 (dd, 1H), 7.24 (d, 1H), 7.09-7.05 (m, 2H), 7.02 (s, 1H), 6.78 (dd, 1H), 6.42 (br s, 1H), 6.35 (s, 1H), 5.85 (d, 1H), 4.56 (d, 2H), 3.74 (s, 3H), 3.67 (s, 3H), 3.54 (dd, 2H), 2.91 (t, 2H).
MS (ESI) m/z 427.4 [M+H]⁺.

EXAMPLE 108

N⁴-(1H-indol-5-ylmethyl)-N²-[2-(5-methoxy-1-methyl-1H-indol-3-yl)ethyl]-N²-methylpyrimidine-2,4-diamine

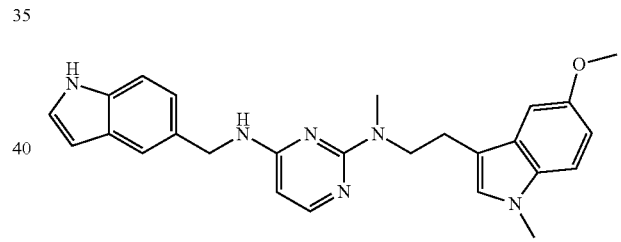

¹H-NMR (500 MHz, CDCl₃) δ 8.21 (br s, 1H), 7.93 (d, 1H), 7.60 (s, 1H), 7.34 (d, 1H), 7.21 (dd, 1H), 7.19-7.12 (m, 3H), 6.85 (dd, 1H), 6.78 (s, 1H), 6.51 (s, 1H), 5.69 (d, 1H), 4.89 (br s, 1H), 4.61 (s, 2H), 3.86 (dd, 2H), 3.00 (t, 2H), 3.78 (s, 3H), 3.66 (s, 3H), 3.11 (s, 3H).
MS (ESI) m/z 441.40 [M+H]⁺.

EXAMPLE 109

N⁴-(1H-indol-5-ylmethyl)-N²-[2-(5-methoxy-1H-indol-3-yl)ethyl]-N²-methylpyrimidine-2,4-diamine

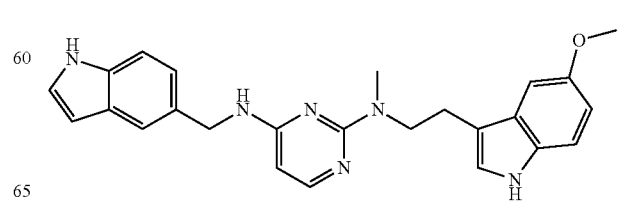

¹H-NMR (500 MHz, DMSO-d₆, 75° C.) δ 10.80 (s, 1H), 10.42 (s, 1H), 7.74 (d, 1H), 7.49 (s, 1H), 7.31 (d, 1H), 7.26 (dd, 1H), 7.21 (d, 1H), 7.15-7.04 (m, 4H), 6.71 (dd, 1H), 6.34 (s, 1H), 5.80 (d, 1H), 4.56 (d, 2H), 3.81 (t, 2H), 3.73 (s, 3H), 3.05 (s, 3H), 2.93 (t, 2H).
MS (ESI) m/z 427.3 [M+H]⁺.

INTERMEDIATE 110

N-(2-chloropyrimidin-4-yl)-1,2-dimethyl-1H-indol-5-amine

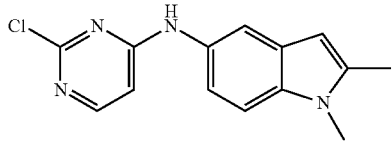 [SMILES: Cc1cc2cc(Nc3ccnc(Cl)n3)ccc2n1C]

¹H-NMR (500 MHz, DMSO-d₆) δ 9.57 (s, 1H), 8.02 (d, 1H), 7.51 (s, 1H), 7.35 (d, 1H), 7.10 (d, 1H), 6.58 (d, 1H), 6.20 (s, 1H), 3.66 (s, 3H), 2.41 (s, 3H).
MS (ESI) m/z 273.0 [M+H]⁺.

INTERMEDIATE 111 methyl 5-(2-chloropyrimidin-4-ylamino)-1H-indole-2-carboxylate

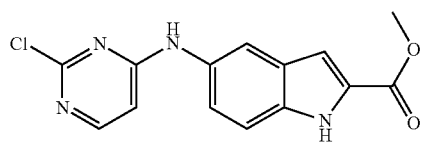 [SMILES: COC(=O)c1cc2cc(Nc3ccnc(Cl)n3)ccc2[nH]1]

¹H-NMR (500 MHz, DMSO-d₆, 75° C.) δ 11.76 (br s, 1H), 9.70 (s, 1H), 8.07 (d, 1H), 7.80 (s, 1H), 7.47 (d, 1H), 7.33 (dd, 1H), 7.14 (s, 1H), 6.65 (d, 1H), 3.89 (s, 3H).
MS (ESI⁺) m/z 303.1 [M+H]⁺.

INTERMEDIATE 112

N-(2-chloropyrimidin-4-yl)-2,3-dimethyl-1H-indol-5-amine

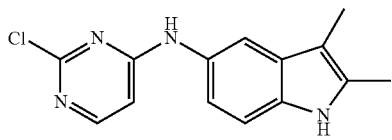 [SMILES: Cc1[nH]c2ccc(Nc3ccnc(Cl)n3)cc2c1C]

¹H-NMR (500 MHz, DMSO-d₆, 75° C.) δ 10.52 (s, 1H), 9.55 (s, 1H), 8.01 (d, 1H), 7.42 (s, 1H), 7.23 (d, 1H), 7.02 (d, 1H), 6.56 (d, 1H), 2.32 (s, 3H), 2.14 (s, 3H).
MS (ESI⁺) m/z 273.2 [M+H]⁺.

INTERMEDIATE 113

N-(2-chloropyrimidin-4-yl)-1H-benzo[d]imidazol-5-amine

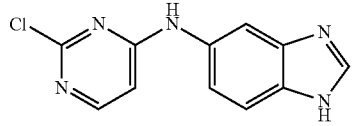 [SMILES: Clc1nccc(Nc2ccc3[nH]cnc3c2)n1]

¹H-NMR (500 MHz, DMSO-d₆) δ 12.38 (br s, 1H), 10.00 (br s, 1H), 8.19 (s, 1H), 8.10 (d, 1H), 7.94 (br s, 1H), 7.58 (d, 1H), 7.22 (d, 1H), 6.71 (d, 1H).
MS (ESI⁺) m/z 246.1 [M+H]⁺.

INTERMEDIATE 114

N-(2-chloropyrimidin-4-yl)-2-methyl-1H-benzo[d]imidazol-5-amine

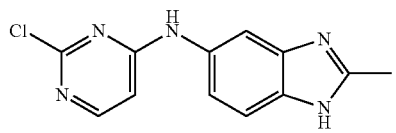 [SMILES: Cc1nc2cc(Nc3ccnc(Cl)n3)ccc2[nH]1]

¹H-NMR (500 MHz, DMSO-d₆, 75° C.) δ 12.01 (s, 1H), 9.75-9.68 (m, 1H), 8.07 (s, 1H), 7.74-7.69 (m, 1H), 7.46-7.36 (m, 1H), 7.18-7.12 (m, 1H), 6.68-6.64 (m, 1H), 2.48 (s, 3H).
MS (ESI⁺) m/z 260.1 [M+H]⁺.

INTERMEDIATE 115

2-chloro-6-methyl-N-[(2-methyl-1H-indol-5-yl)methyl]pyrimidin-4-amine

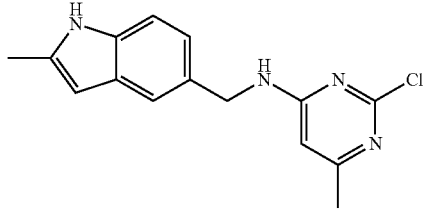 [SMILES: Cc1cc(NCc2ccc3[nH]c(C)cc3c2)nc(Cl)n1]

¹H-NMR (500 MHz, DMSO-d₆, 75° C.) δ 10.66 (br s, 1H), 7.93 (br s, 1H), 7.33 (s, 1H), 7.21 (d, 1H), 6.95 (d, 1H), 6.33 (s, 1H), 6.07 (s, 1H), 4.49 (d, 2H), 2.37 (s, 3H), 2.18 (s, 3H).
MS (ESI⁺) m/z 287.1 [M+H]⁺.

INTERMEDIATE 116

2-[(tert-butyldimethylsilyloxy)methyl]-N-(2-chloropyrimidin-4-yl)-1H-indol-5-amine

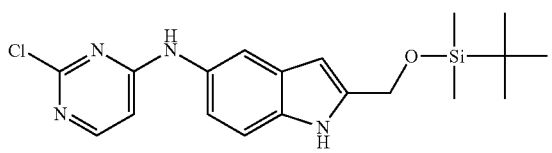 [SMILES: CC(C)(C)[Si](C)(C)OCc1cc2cc(Nc3ccnc(Cl)n3)ccc2[nH]1]

¹H-NMR (500 MHz, DMSO-d₆, 75° C.) δ 10.86 (s, 1H), 9.57 (s, 1H), 8.02 (d, 1H), 7.57 (s, 1H), 7.36 (d, 1H), 7.09 (dd, 1H), 6.59 (d, 1H), 6.31 (s, 1H), 4.80 (s, 2H), 0.92 (s, 9H), 0.10 (s, 6H).

MS (ESI⁺) m/z 389.2 [M+H]⁺.

INTERMEDIATE 117

N-(2-chloropyrimidin-4-yl)-N,2-dimethyl-1H-indol-5-amine

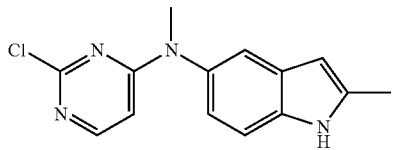 [SMILES: Cc1cc2cc(N(C)c3ccnc(Cl)n3)ccc2[nH]1]

¹H-NMR (500 MHz, DMSO-d₆) δ 11.14 (s, 1H), 7.86 (d, 1H), 7.37 (d, 1H), 7.34 (s, 1H), 6.89 (dd, 1H), 6.16 (s, 1H), 6.07 (br s, 1H), 3.39 (s, 3H), 2.39 (s, 3H).

MS (ESI⁺) m/z 273.2 [M+H]⁺.

INTERMEDIATE 118

N-(2-chloropyrimidin-4-yl)-N,1,2-trimethyl-1H-indol-5-amine

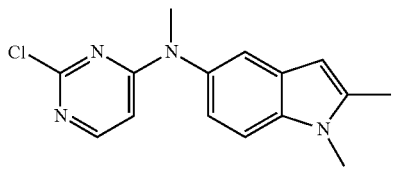 [SMILES: Cc1cc2cc(N(C)c3ccnc(Cl)n3)ccc2n1C]

¹H-NMR (500 MHz, DMSO-d₆) δ 7.86 (d, 1H), 7.50 (d, 1H), 7.38 (s, 1H), 6.98 (dd, 1H), 6.26 (s, 1H), 6.06 (br s, 1H), 3.69 (s, 3H), 3.40 (s, 3H), 2.40 (s, 3H).

MS (ESI⁺) m/z 287.1 [M+H]⁺.

INTERMEDIATE 119

4-chloro-N-[2-(5-methoxy-1-methyl-1H-indol-3-yl)ethyl]pyrimidin-2-amine

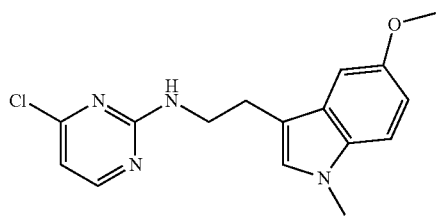 [SMILES: COc1ccc2c(c1)c(CCNc1nccc(Cl)n1)cn2C]

¹H-NMR (500 MHz, DMSO-d₆, 75° C.) δ 8.23 (d, 1H), 7.46 (m, 1H), 7.25 (d, 1H), 7.08 (m, 2H), 6.79 (dd, 1H), 6.63 (d, 1H), 3.78 (s, 3H), 3.69 (s, 3H), 3.54 (q, 2H), 2.91 (t, 2H).

MS (ESI⁺) m/z 317.3 [M+H]⁺.

INTERMEDIATE 120

4-chloro-N-[2-(5-methoxy-1-methyl-1H-indol-3-yl)ethyl]-N-methylpyrimidin-2-amine

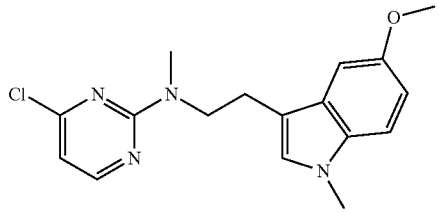 [SMILES: COc1ccc2c(c1)c(CCN(C)c1nccc(Cl)n1)cn2C]

¹H-NMR (500 MHz, CDCl₃) δ 8.17 (d, 1H), 7.18-7.16 (m, 2H), 6.88 (dd, 1H), 6.85 (s, 1H), 6.48 (s, 1H), 3.88-3.85 (m, 5H), 3.71 (s, 3H), 3.13 (s, 3H), 3.00 (m, 2H).

MS (ESI⁺) m/z 331.2 [M+H]⁺.

Biological Assays

The Fluorometric Microculture Cytotoxicity Assay, FMCA, is a three day non-clonogenic microplate-based cell viability assay used for measurement of the cytotoxic and/or cytostatic effect of compounds in vitro (Lindhagen, E., et al. Nat Protoc, 2008. 3(8): p. 1364-9). FMCA (Larsson, R. and P. Nygren, Anticancer Res, 1989. 9(4): p. 1111-9) represents a valuable method to measure cytotoxicity in a number of cell types, both cell lines and primary cells from patients (Larsson, R., et al., Int J Cancer, 1992. 50(2): p. 177-85; Fridborg, H., et al., Eur J Cancer, 1999. 35(3): p. 424-32; Dhar, S., et al., Br J Cancer, 1996. 74(6): p. 888-96).

FMCA is based on the principle that fluorescein diacetate (FDA) is converted to the fluorescent probe fluorescein by esterases in the plasma membranes of living cells. For experiments, 96 or 384-well microplates are prepared with compounds and stored at −70° C. until use. Cells are then seeded into the drug-prepared plates and placed in an incubator for 72 h. On the last day of incubation, the plates are washed and a buffer containing FDA is added and incubated with the cells for 45 minutes. Finally the fluorescence per well is measured in a fluorometer and a Survival Index % (SI) for each compound-treated well is calculated with the equation: Compound-treated cells minus blank divided by control cells minus blank. A high SI-value indicates a large percentage of living cells and vice versa.

For experiments with compounds of the invention, 96-well plates were prepared as follows:

Compounds were dissolved in DMSO to 10 mM and stored at −20° C. 96-well plates were prepared with 297 μl of sterile PBS added to each well. The test compounds were thawed, protected from light, mixed, and 3 μl of stock solution was added to the 96-well plate to give the concentration 100 μM. Then, an assay plate was prepared by transferring 20 μl of compound solution to a V-bottomed 96-well plate. Compounds at 100 μM were diluted with PBS to 10 μM, and an assay plate containing 20 μl was prepared. The plates were stored at −70° C. until use.

On the day of cell seeding, 180 μl of cell suspension was added to each well in the two assay plates. The final concentration of compounds tested was thus 10 μM and 1 μM.

In subsequent experiments, compounds were tested, along with kinase inhibitors (dasatinib, pazopanib, sorafenib, and sunitinib) as described above. Initially, the acute lymphoblastic leukaemia cell line CCRF-CEM (see e.g. Foley G E, et al. Cancer 1965, 18, 522-529) was used throughout. In the assay plates, medium was added to six empty wells (blank wells) and wells were filled with PBS and cell suspension and served as control wells. SI-values were then calculated for each compound-treated well as described above. All experiments were conducted twice and a new batch of plates was prepared for each experiment. The data obtained showed the activity of the example compounds compared to the comparative compounds.

For dose-response experiments, 384-well plates were prepared as follows:

Compounds of the invention as well as kinase inhibitors sorafenib, sunitinib, dasatinib, and pazopanib (reference compounds) were diluted with PBS to a concentration which was ten-times higher than the desired starting concentration. Then, a Biomek 2000 liquid handling system was employed to serially dilute the compounds in a deep-well 384-well plate. From this plate, assay plates containing 5 µl compound per well were prepared with the Biomek 2000. Certain compounds precipitated when diluted with PBS, and these compounds were therefore prepared in a 96-well plate manually as described above using culture medium RPMI 1640 instead of PBS.

The compounds were also tested at five concentrations, with five times serial dilution on the following cell types: CCRF-CEM, hTERT-RPE1 (normal retinal epithelial cells), hRPTEpiC (normal renal cells) and PBMC (peripheral blood mononuclear cells). Each experiment was performed three times, except for PBMC and hRPTEpiC, which were performed twice. SI-values were calculated, graphs were plotted using GraphPadPrism 5.0 (GraphPad Software Inc. La Jolla, Calif.) and $EC_{50}$-values for each cell type and compound were determined from the curves.

The example compounds of the invention were active in the CCRF-CEM cell measurements, showing $EC_{50}$ values less than 10 µM. Preferred compounds of the invention had $EC_{50}$ values less than 1 µM. More preferred compounds of the invention had $EC_{50}$ values less than 0.1 µM, and the reference compounds, sorafenib, sunitinib, dasatinib, and pazopanib, had $EC_{50}$ values of 8.3 µM, 14.1 µM, 9.7 µM, and 25.9 µM respectively, in this assay. Most of the compounds of the invention showed lower $EC_{50}$ values than the reference compounds and data is presented in Table 1.

TABLE 1

EC50 (50 µM) in CCRF-CEM cancer cells - leukaemia

| Example number | CCRF-CEM EC50 (µM) |
| --- | --- |
| 1 | 0.33 |
| 2 | 4.83 |
| 3 | 4.25 |
| 4 | 4.07 |
| 9 | 8.73 |
| 10 | 10.2 |
| 11 | 2.88 |
| 12 | 0.76 |
| 13 | 0.55 |
| 17 | 7.28 |
| 18 | 0.71 |
| 19 | 1.02 |
| 20 | 1.01 |
| 23 | 1.62 |
| 24 | 0.38 |
| 25 | 3.16 |
| 26 | 7.01 |
| 27 | 4.17 |
| 28 | 3.10 |
| 29 | 2.78 |
| 30 | 0.30 |
| 32 | 7.81 |
| 33 | 9.55 |
| 35 | 10.1 |
| 37 | 0.42 |
| 38 | 4.33 |
| 39 | 2.84 |
| 40 | 4.17 |
| 63 | 0.59 |
| 64 | 0.05 |
| 65 | 0.92 |
| 66 | 0.21 |
| 67 | 0.21 |
| 69 | <10 |
| 70 | <10 |
| 71 | <10 |
| 72 | <10 |
| 73 | <10 |
| 74 | <10 |
| 75 | 0.61 |
| 76 | 0.23 |
| 81 | <10 |
| 82 | 0.49 |
| 83 | <10 |
| 84 | 0.04 |
| 85 | <10 |
| 86 | tbt.ndy |
| 87 | tbt.ndy |
| 88 | tbt.ndy |
| 89 | tbt.ndy |
| 90 | tbt.ndy |
| 91 | tbt.ndy |
| 92 | tbt.ndy |
| 93 | tbt.ndy |
| 94 | tbt.ndy |
| 95 | 0.90 |
| 96 | 0.68 |
| 97 | tbt.ndy |
| 98 | tbt.ndy |
| 99 | tbt.ndy |
| 100 | tbt.ndy |
| 101 | tbt.ndy |
| 102 | tbt.ndy |
| 103 | tbt.ndy |
| 104 | tbt.ndy |
| 105 | tbt.ndy |
| 106 | tbt.ndy |
| 107 | tbt.ndy |
| 108 | tbt.ndy |
| 109 | tbt.ndy |
| Ref. 1 | 8.3 |
| Ref. 2 | 14.1 |
| Ref. 3 | 9.7 |
| Ref. 4 | 25.9 | tbt.ndy denotes "to be tested, no data available yet".
Ref. 1 denotes reference compound sorafenib
Ref. 2 denotes reference compound sunitinib
Ref. 3 denotes reference compound dasatinib
Ref. 4 denotes reference compound pazopanib Further, primary results also showed that the compounds of the invention exhibited an enhanced selectivity towards CCRF-CEM cells, compared to the tested hTERT-RPE1 (normal retinal epithelial cells), hRPTEpiC (normal renal cells), and peripheral blood mononuclear cells (PBMC).

The compounds of the invention were also tested on further cancer cell lines related to colon cancer (HCT116; see e.g Brattain M G, et al. Cancer Res. 1981, 41, 1751-1756), breast cancer (MCF7; see e.g. Soule H D, et al. J. Natl. Cancer Inst. 1973, 51, 1409-1416), teniposide-resistant leukaemia (CEM/VM1; see e.g. Danks M K et al. Cancer Res. 1987, 47, 1297-1301), lung cancer (H69; see e.g. Gazdar A F, et al. Cancer Res. 1980, 40, 3502-3507), doxorubicin-resistant lung cancer (H69AR; see e.g. Mirski S E, et al. Cancer Res. 1987, 47, 2594-2598), myeloma (RPMI 8226; see e.g. Matsuoka Y, et al. Proc. Soc. Exp. Biol. Med. 1967, 125, 1246-1250), doxorubicin-resistant myeloma (8226/Dox40; see e.g. Dalton W S et al. Blood 1989, 15,747-752), lymphoma (U-937, see e.g. Sundstrom C, et al. Int. J. Cancer 1976, 17, 565-577), vincristin-resistant lymphoma (U-937-vcr; see e.g. Botling J, et al. Int J Cancer 1994, 15; 58 (2), 269-274), ovarian cancer (A2780; see e.g. Hamilton T C, et al. Semin Oncol. 1984, 11, 285-298), doxorubicin-resistant ovarian cancer (A2780/Adr), cisplatin-resistant ovarian cancer (A2780/Cis; see e.g. Behrens B C, et al. Cancer Res. 1987, 47, 414-418), renal cancer (ACHN; see e.g. Borden E C, et al. Cancer Res. 1982, 42(12), 4948-4953), pancreatic cancer (PANC-1, BxPC-3, and MIA PaCa-2; see e.g. Lieber M, et al. Int. J. Cancer 1975, 15, 741-747; Loor R, et al. Clin. Lab. Med. 1982, 2, 567-578; and Yunis A A, et al. Int. J. Cancer 1977, 19, 128-135). Representative results of these tests are presented in Table 2 and Table 3.

TABLE 2

EC50 (µM) in various cancer cell lines

| Ex. | HCT116 | MCF7 | CEM/VM1 | H69 | H69 AR | RPMI 8226 | 8226/Dox40 | ACHN |
|---|---|---|---|---|---|---|---|---|
| 1 | 6.70 | 9.0 | 0.12 | 10.8 | nt | 0.50 | 0.37 | 2.54 |
| 12 | 0.63 | 3.88 | 0.17 | 7.84 | 0.27 | 0.53 | 1.81 | 1.90 |
| 19 | 9.83 | 28.5 | 1.33 | 30.7 | nt | 12.80 | 46.3 | 25.2 |
| 24 | 0.51 | 4.43 | 0.21 | 9.35 | 0.46 | 0.23 | 0.41 | 1.26 |
| 30 | 2.62 | 11.0 | 0.35 | 7.14 | nt | 0.34 | 0.34 | 3.30 |
| 37 | 6.20 | 4.92 | 0.23 | 11.6 | nt | 0.81 | 2.02 | 3.08 |
| 64 | 1.33 | 2.33 | 0.05 | 4.18 | 0.29 | 0.23 | 1.19 | 1.60 |
| 66 | 2.45 | 3.35 | 0.27 | 11.6 | 0.64 | 1.83 | 10.0 | 3.32 |
| 67 | 2.47 | 12.4 | 0.33 | 37.2 | 0.71 | 5.01 | 24.4 | 5.43 |
| 76 | 3.09 | 3.08 | 0.22 | 12.7 | 0.34 | 0.70 | 1.10 | 1.59 |
| 84 | 1.16 | 2.06 | 0.19 | 5.47 | 0.35 | 0.45 | 2.58 | 1.62 |

"nt" denotes "not yet tested".

TABLE 3

EC50 (µM) in various cancer cell lines

| Ex. | U-937 | U-937-ver | A2780 | A2780/Adr | A2780/Cis | BxPC-3 | PANC-1 | MIA PaCa-2 |
|---|---|---|---|---|---|---|---|---|
| 1 | 0.07 | 0.07 | 0.70 | 2.40 | 0.35 | nt | nt | nt |
| 12 | 0.27 | 0.30 | 0.47 | 1.90 | 0.61 | <0.1 | <0.1 | <0.1 |
| 19 | 1.47 | 1.81 | 1.59 | 12.6 | 1.99 | <1 | <1 | <1 |
| 24 | 0.19 | 0.19 | 0.28 | 0.60 | 0.22 | nt | nt | nt |
| 30 | 0.32 | 0.19 | 0.30 | 1.62 | 0.25 | nt | nt | nt |
| 37 | 0.29 | 0.34 | 0.45 | 1.71 | 0.32 | <0.1 | <0.1 | <0.1 |
| 64 | 0.08 | 0.32 | 0.29 | nt | nt | nt | nt | nt |
| 66 | 0.35 | 0.99 | 0.78 | nt | nt | nt | nt | nt |
| 67 | 0.22 | 1.74 | 1.37 | nt | nt | nt | nt | nt |
| 76 | 0.19 | 0.40 | 0.34 | nt | nt | nt | nt | nt |
| 84 | 0.21 | 0.27 | 0.33 | nt | nt | nt | nt | nt |

"nt" denotes "not yet tested".

Example compounds were further tested in a tubulin polymerization assay kit from Cytoskeleton Inc (Denver, Colo., USA). Polymerization is followed by fluorescence enhancement due to the incorporation of a fluorescent reporter into microtubules as polymerization occurs. Vincristine and paclitaxel at 3 µM were used as positive controls for tubulin polymerization inhibition and stabilisation, respectively. All compounds were dissolved in DMSO, which was used as solvent control. For experiments, example compounds and control compounds were incubated with bovine tubulin protein in a cell-free environment and the fluorescence was then measured in a fluorometer (Fluostar Optima, BMG Labtech, Offenburg, Germany) at 360/450 nm every minute for a total of 60 mins. Some selected example compounds showed inhibitory effects on tubulin polymerization.

Example compounds were further tested for induction of apoptosis in a Live cell imaging setup. The NucView™ 488 Caspase-3 Assay Kit for Live cells (Biotium, Inc. Hayward, Calif., USA) was used. HCT116 cells were plated the day before the experiment in black glass-bottom PerkinElmer plates and compounds with chosen concentrations were then added. Finally, the DEVD-NucView488 Caspase-3 substrate was added and the plate was placed in an IncuCyteFLR for live-cell imaging. When the substrate is cleaved by activated caspase-3, a dye is released which becomes fluorescent upon binding to DNA (Cen H et al. DEVD-NucView488: a novel class of enzyme substrates for real-time detection of caspase-3 activity in live cells. FASEB J. 2008 July: 22(7): 2243-52.). Staurosporin at 1 µM was used as a positive control for apoptosis. Selected example compounds were tested and all of them induced apoptosis at the chosen concentrations at varying time points.

The invention claimed is:

1. A compound of formula I or a pharmaceutically acceptable solvate or salt thereof,

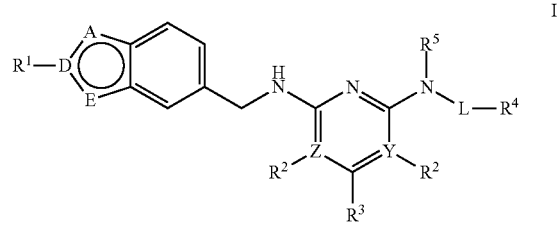

wherein
Z represents carbon or nitrogen;
Y represents carbon or nitrogen, wherein one of Z and Y represents nitrogen and the other is carbon;
A, D and E is selected from carbon or nitrogen, wherein A and D represent nitrogen and E represents carbon; or A and E represent nitrogen and D represents carbon; or E represents nitrogen and A and D represent carbon;
L represents a bond or $(C_1-C_2)$alkyl;
$R_1$ represents hydrogen or methyl, when D represents carbon;
$R^2$ represents hydrogen or amino, when Y or Z represents carbon;
$R^3$ represents hydrogen, $(C_1-C_3)$alkyl, amino, trifluoromethyl or $(C_0-C_1)$alkylaryl;
$R^4$ represents heteroaryl, optionally substituted with one or more substituents; and
$R^5$ represents hydrogen or methyl;
wherein when D represents nitrogen, $R_1$ is absent, and when Z or Y, respectively, represents nitrogen, $R^2$ is absent, and
when E is nitrogen, L represents a bond or $C_2$ alkyl.

2. The compound or pharmaceutically acceptable solvate or salt thereof according to claim 1, wherein Z and E represent carbon; and Y, D and A represent nitrogen.

3. The compound or pharmaceutically acceptable solvate or salt thereof according to claim 1, wherein Z and D represent carbon; and Y, E and A represent nitrogen.

4. The compound or pharmaceutically acceptable solvate or salt thereof according to claim 1, wherein Z, A and D represent carbon; and Y and E represent nitrogen.

5. The compound or pharmaceutically acceptable solvate or salt thereof according to claim 1, wherein Y and E represent carbon; and Z, D and A represent nitrogen.

6. The compound or pharmaceutically acceptable solvate or salt thereof according to claim 1, wherein Y and D represent carbon; and Z, E and A represent nitrogen.

7. The compound or pharmaceutically acceptable solvate or salt thereof according to claim 1, wherein Y, A and D represent carbon; and Z and E represent nitrogen.

8. The compound or pharmaceutically acceptable solvate or salt thereof according to claim 1, wherein $R^4$ represents a heteroaryl that is optionally substituted with one or more substituents selected from the group consisting of halogen, hydroxy, amino, nitro, cyano, $(C_1-C_4)$alkyl, $(C_1-C_4)$alkyl$(C_2-C_9)$ heterocyclyl, $(C_1-C_4)$alkyl(CO)OH, $(C_1-C_4)$alkyl(CO)O $(C_1-C_4)$alkyl, $(C_1-C_4)$alkyl(CO)NH$_2$, $(C_1-C_4)$alkyl(CO)NH $(C_1-C_4)$alkyl, $(C_1-C_4)$alkyl(CO)NH$(C_1-C_4)$alkyl(CO)OH, $(C_1-C_4)$alkyl-OH, $(C_1-C_4)$alkyl-O$(C_1-C_4)$alkyl, $(C_1-C_4)$alkyl-O$(C_6-C_{10})$aryl, $(C_1-C_4)$alkyl-O(CO)$(C_1-C_4)$alkyl, $(C_1-C_4)$alkyl-O(CO)$(C_1-C_4)$alkyl-NH$_2$, $(C_1-C_4)$alkyl-O(CO) $(C_6-C_{10})$aryl, $(C_1-C_4)$alkyl-NH$_2$, $(C_1-C_4)$alkyl-NH$(C_1-C_4)$alkyl, $(C_1-C_4)$alkyl-N[$(C_1-C_4)$alkyl][$(C_1-C_4)$-alkyl], $(C_1-C_4)$alkyl-NH(CO)$(C_1-C_4)$alkyl, $(C_1-C_4)$alkyl-NH(CO)$(C_1-C_4)$alkyl-NH$_2$, $(C_1-C_4)$alkyl-NH(CO)$(C_6-C_{10})$aryl, $(C_1-C_4)$alkyl(CN), $(C_1-C_4)$alkyl$(C_6-C_{10})$aryl, (CO)OH, (CO)O$(C_1-C_4)$alkyl, (CO)NH$_2$, (CO)NH$(C_1-C_4)$alkyl, (CO)NH$(C_1-C_4)$alkyl(CO)OH, (CO)$(C_1-C_4)$alkyl, (CO)$(C_1-C_4)$alkyl$(C_6-C_{10})$aryl, (CO)$(C_1-C_4)$alkyl$(C_1-C_9)$heteroaryl, (CO)$(C_1-C_4)$alkyl$(C_2-C_9)$heterocyclyl, (CO)$(C_2-C_9)$heterocyclyl, (CO)$(C_6-C_{10})$aryl, (CO)$(C_1-C_9)$heteroaryl, $(C_6-C_{10})$aryl, $(C_6-C_{10})$aryl-halogen, $(C_6-C_{10})$aryl-OH, $(C_6-C_{10})$aryl-NH$_2$, $(C_6-C_{10})$aryl-O$(C_1-C_4)$alkyl, $(C_1-C_9)$heteroaryl, $(C_1-C_9)$heteroaryl-OH, $(C_1-C_9)$heteroaryl-halogen, $(C_1-C_9)$heteroaryl-NH$_2$, $(C_1-C_9)$heteroaryl$(C_1-C_4)$alkyl, $(C_1-C_9)$heteroaryl-O$(C_1-C_4)$alkyl, $(C_2-C_9)$heterocyclyl, $(C_2-C_9)$heterocyclyl$(C_1-C_4)$alkyl, $(C_2-C_9)$heterocyclyl$(C_1-C_4)$alkyl-OH, $(C_2-C_9)$heterocyclyl$(C_1-C_4)$alkyl-NH$_2$, O$(C_1-C_4)$alkyl, O$(C_1-C_4)$alkyl$(C_6-C_{10})$aryl, O$(C_1-C_4)$alkyl $(C_6-C_{10})$heteroaryl, O$(C_1-C_4)$alkyl$(C_2-C_9)$heterocyclyl, O$(C_1C_4)$alkyl $(C_2-C_9)$heterocyclyl $(C_1-C_4)$ alkyl, O$(C_1-C_4)$alkyl$(C_2-C_9)$heterocyclyl$(C_1-C_4)$alkyl-OH, O(EtO)$_{1-3}$H, O(EtO)$_{1-3}$$(C_1-C_4)$alkyl, O$(C_6-C_{10})$aryl, O(CO)$(C_1-C_4)$alkyl, O(CO)$(C_1-C_4)$alkyl-NH$_2$, O(CO)$(C_6-C_{10})$aryl, OCF$_3$, OSO$_2$$(C_1-C_4)$alkyl, OSO$_2$OH, NH$(C_1-C_4)$alkyl, N[$(C_1-C_4)$alkyl][$(C_1-C_4)$alkyl], NH(CO)$(C_1-C_4)$alkyl, NH(CO)$(C_1-C_4)$alkyl-NH$_2$, NH(CO)$(C_6-C_{10})$aryl, NHSO$_2$$(C_1-C_4)$alkyl, SO$_2$NH$_2$, and CF$_3$.

9. The compound or pharmaceutically acceptable solvate or salt thereof according to claim 1, wherein L-$R^4$ is selected from:

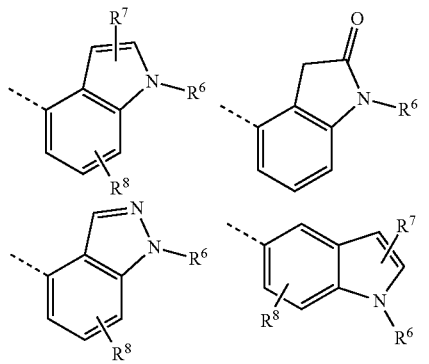

wherein $R^6$ is selected from hydrogen or $(C_1-C_4)$alkyl;

$R^7$ is selected from hydrogen, halogen, nitro, cyano, $(C_1-C_4)$alkyl, $(C_1-C_4)$alkyl(CO)OH, $(C_1-C_4)$alkyl(CO)O $(C_1-C_4)$alkyl, $(C_1-C_4)$alkyl(CO)NH$_2$, $(C_1-C_4)$alkyl (CO)NH$(C_1-C_4)$alkyl, $(C_1-C_4)$alkyl-OH, $(C_1-C_4)$alkyl-O$(C_6-C_{10})$aryl, $(C_1-C_4)$alkyl-O(CO)$(C_1-C_4)$alkyl, $(C_1C_4)$alkyl-O(CO)$(C_6-C_{10})$aryl, $(C_1-C_4)$alkyl-NH$_2$, $(C_1-C_4)$alkyl-NH$(C_1-C_4)$alkyl, $(C_1-C_4)$alkyl-N[$(C_1-C_4)$alkyl][$(C_1-C_4)$alkyl], $(C_1-C_4)$alkyl-NH(CO)$(C_1-C_4)$alkyl, $(C_1-C_4)$alkyl(CN), $(C_1-C_4)$alkyl $(C_6-C_{10})$aryl, $(C_1-C_4)$alkyl$(C_2-C_9)$heterocyclyl, (CO)OH, (CO)O $(C_1-C_4)$alkyl, (CO)NH$_2$, (CO)NH$(C_1-C_4)$alkyl, (CO) $(C_1-C_4)$alkyl, $(C_6-C_{10})$aryl, $(C_6-C_{10})$aryl-halogen, $(C_6-C_{10})$aryl-OH, $(C_6-C_{10})$aryl-O$(C_1-C_4)$alkyl, $(C_1-C_9)$heteroaryl, $(C_1-C_9)$heteroaryl-halogen, $(C_1-C_9)$heteroaryl-OH, $(C_1-C_9)$heteroaryl-O$(C_1-C_4)$alkyl, $(C_2-C_9)$heterocyclyl, $(C_2-C_9)$heterocyclyl$(C_1-C_4)$alkyl, or $(C_2-C_9)$heterocyclyl$(C_1-C_4)$alkyl-OH;

$R^7$a and $R^7$b are independently selected from hydrogen or $(C_1-C_4)$alkyl;

$R^8$ is selected from hydrogen, halogen, nitro, cyano, hydroxy, amino, $(C_1-C_4)$alkyl, $(C_1-C_4)$alkyl$(C_2-C_9)$heterocyclyl, $(C_1-C_4)$alkyl-NH$_2$, $(C_1-C_4)$alkyl-NH$(C_1-C_4)$alkyl, $(C_1-C_4)$alkyl-N[$(C_1C_4)$alkyl][$(C_1-C_4)$-alkyl], $(C_1-C_4)$alkyl-NH(CO)$(C_1-C_4)$alkyl, $(C_1-C_4)$alkyl-NH (CO)$(C_6-C_{10})$aryl, (CO)$(C_1-C_4)$alkyl, (CO)OH, (CO)O $(C_1-C_4)$alkyl,(CO)NH$_2$, (CO)NH$(C_1-C_4)$alkyl, O$(C_1-C_4)$alkyl, O$(C_1-C_4)$alkyl$(C_6-C_{10})$aryl, O$(C_1-C_4)$alkyl $(C_2-C_9)$heteroaryl, O$(C_1C_4)$alkyl$(C_2-C_9)$heterocyclyl, O$(C_1-C_4)$alkyl$(C_2-C_9)$heterocyclyl$(C_1-C_4)$alkyl, O$(C_1-C_4)$alkyl$(C_2-C_9)$heterocyclyl$(C_1-C_4)$alkyl-OH, O(EtO)$_{1-3}$H, O(EtO)$_{1-3}$$(C_1-C_4)$alkyl, O$(C_6-C_{10})$aryl, OCF$_3$, O(CO)(C$_1$-C$_4$)alkyl, O(CO)(C$_6$-C$_{10}$)aryl, OSO$_2$OH, NH(C$_1$-C$_4$)alkyl, N[(C$_1$-C$_4$)alkyl][(C$_1$-C$_4$)alkyl], NH(CO)(C$_1$C$_4$)alkyl, NH(CO)(C$_6$-C$_{10}$)aryl, CF$_3$, (C$_6$-C$_{10}$)aryl, (C$_6$-C$_{10}$)aryl-halogen, (C$_6$-C$_{10}$)aryl-OH, (C$_6$-C$_{10}$)aryl-O(C$_1$-C$_4$)alkyl, (C$_1$-C$_9$)heteroaryl, (C$_1$-C$_9$)heteroaryl-halogen, (C$_1$-C$_9$)heteroaryl-OH, (C$_1$-C$_9$)heteroaryl-O(C$_1$-C$_4$)alkyl, (C$_2$-C$_9$)heterocyclyl, (C$_2$-C$_9$)heterocyclyl(C$_1$-C$_4$)alkyl, or (C$_2$-C$_9$)heterocyclyl(C$_1$-C$_4$)alkyl-OH;

R$^9$ is selected from the hydrogen, halogen, (C$_1$C$_4$)alkyl, (C$_1$-C$_4$)alkyl-OH, (C$_1$-C$_4$)alkyl-O(C$_1$C$_4$)alkyl, (CO)OH, (CO)O(C$_1$-C$_4$)alkyl, (CO)NH$_2$, (CO)NH(C$_1$-C$_4$)alkyl, or (C$_6$-C$_{10}$)aryl; and R$^{11}$ is selected from the hydrogen, hydroxy, (C$_1$-C$_4$)alkyl, or O(C$_1$-C$_4$)alkyl.

10. The compound or pharmaceutically acceptable solvate or salt thereof according to claim 1, wherein R$^5$ represents hydrogen.

11. The compound or pharmaceutically acceptable solvate or salt thereof according to claim 1, wherein R$^5$ represents methyl.

12. The compound or pharmaceutically acceptable solvate or salt thereof according to claim 1, wherein R$^2$ represents amino.

13. The compound or pharmaceutically acceptable solvate or salt thereof according to claim 1, wherein R$^2$ represents hydrogen.

14. The compound or pharmaceutically acceptable solvate or salt thereof according to claim 1, wherein R$^2$ represents hydrogen; and R$^3$ represents hydrogen, methyl, trifluoromethyl or benzyl.

15. The compound or pharmaceutically acceptable solvate or salt thereof according to claim 1, wherein Z and E represent carbon;
Y, D, and A represent nitrogen;
L represents a bond or C$_2$ alkyl;
R$^2$ represents hydrogen;
R$^3$ represents hydrogen or methyl;
R$^4$ represents a heteroaryl selected from indolyl, indazolyl, benzimidazolyl, or indolinonyl, said heteroaryl optionally substituted with one or two substituents selected from the group consisting of halogen, hydroxy, amino, nitro, cyano, (C$_1$-C$_4$)alkyl, (C$_1$-C$_4$)alkyl(C$_2$-C$_9$)heterocyclyl, (C$_1$-C$_4$)alkyl(CO)OH, (C$_1$-C$_4$)alkyl(CO)O(C$_1$-C$_4$)alkyl, (C$_1$-C$_4$)alkyl(CO)NH$_2$, (C$_1$-C$_4$)alkyl(CO)NH(C$_1$-C$_4$)alkyl, (C$_1$-C$_4$)alkyl(CO)NH(C$_1$-C$_4$)alkyl(CO)OH, (C$_1$-C$_4$)alkyl-OH, (C$_1$-C$_4$)alkyl-O(C$_1$-C$_4$)alkyl, (C$_1$-C$_4$)alkyl-O(C$_6$-C$_{10}$)aryl, (C$_1$-C$_4$)alkyl-O(CO)(C$_1$-C$_4$)alkyl, (C$_1$-C$_4$)alkyl-O(CO)(C$_1$-C$_4$)alkyl-NH$_2$, (C$_1$-C$_4$)alkyl-O(CO)(C$_6$-C$_{10}$)aryl, (C$_1$-C$_4$)alkyl-NH$_2$, (C$_1$-C$_4$)alkyl-NH(C$_1$-C$_4$)alkyl, (C$_1$-C$_4$)alkyl-N[(C$_1$-C$_4$)alkyl][(C$_1$-C$_4$)-alkyl], (C$_1$-C$_4$)alkyl-NH(CO)(C$_1$-C$_4$)alkyl, (C$_1$-C$_4$)alkyl-NH(CO)(C$_1$-C$_4$)alkyl-NH$_2$, (C$_1$-C$_4$)alkyl-NH(CO)(C$_6$-C$_{10}$)aryl, (C$_1$-C$_4$)alkyl(CN), (C$_1$-C$_4$)alkyl(C$_6$-C$_{10}$)aryl, (CO)OH, (CO)O(C$_1$-C$_4$)alkyl, (CO)NH$_2$, (CO)NH(C$_1$-C$_4$)alkyl, (CO)NH(C$_1$-C$_4$)alkyl(CO)OH, (CO)(C$_1$-C$_4$)alkyl, (CO)(C$_1$-C$_4$)alkyl(C$_6$-C$_{10}$)aryl, (CO)(C$_1$-C$_4$)alkyl(C$_1$-C$_9$)heteroaryl, (CO)(C$_1$-C$_4$)alkyl(C$_2$-C$_9$)heterocyclyl, (CO)(C$_2$-C$_9$)heterocyclyl, (CO)(C$_6$-C$_{10}$)aryl, (CO)(C$_1$-C$_9$)heteroaryl, (C$_6$-C$_{10}$)aryl, (C$_6$-C$_{10}$)aryl-halogen, (C$_6$-C$_{10}$)aryl-OH, (C$_6$-C$_{10}$)aryl-NH$_2$, (C$_6$-C$_{10}$)aryl-O(C$_1$-C$_4$)alkyl, (C$_1$-C$_9$)heteroaryl, (C$_1$-C$_9$)heteroaryl-halogen, (C$_1$-C$_9$)heteroaryl-OH, (C$_1$-C$_9$)heteroaryl-NH$_2$, (C$_1$-C$_9$)heteroaryl(C$_1$-C$_4$)alkyl, (C$_1$-C$_9$)heteroaryl-O(C$_1$-C$_4$)alkyl, (C$_2$-C$_9$)heterocyclyl, (C$_2$-C$_9$)heterocyclyl(C$_1$-C$_4$)alkyl, (C$_2$-C$_9$)heterocyclyl(C$_1$-C$_4$)alkyl-OH, (C$_2$-C$_9$)heterocyclyl(C$_1$-C$_4$)alkyl-NH$_2$, O(C$_1$-C$_4$)alkyl, O(C$_1$-C$_4$)alkyl (C$_6$-C$_1$)aryl, O(C$_1$-C$_4$)alkyl(C$_6$-C$_{10}$)heteroaryl, O(C$_1$-C$_4$)alkyl(C$_2$-C$_9$)heterocyclyl, O(C$_1$-C$_4$)alkyl(C$_2$-C$_9$)heterocyclyl(C$_1$-C$_4$)alkyl, O(C$_1$-C$_4$)alkyl(C$_2$-C$_9$)heterocyclyl(C$_1$-C$_4$)alkyl-OH, O(EtO)$_{1-3}$H, O (EtO )$_{1-3}$(C$_1$-C$_4$)alkyl, O(C$_6$-C$_{10}$)aryl, O(CO)(C$_1$-C$_4$)alkyl, O(CO)(C$_1$-C$_4$)alkyl-NH$_2$, O(CO)(C$_6$-C$_{10}$)aryl, OCF$_3$, OSO$_2$(C$_1$-C$_4$)alkyl, OSO$_2$OH, NH(C$_1$-C$_4$)alkyl, N[C$_1$-C$_4$)alkyl][(C$_1$-C$_4$)alkyl], NH(CO)(C$_1$-C$_4$)alkyl, NH(CO)(C$_1$ -C$_4$)alkyl-NH$_2$, NH(CO)(C$_6$-C$_{10}$)aryl, NHSO$_2$(C$_1$-C$_4$)alkyl, SO$_2$NH$_2$, and CF$_3$; and R$^5$ represents hydrogen or methyl.

16. The compound or pharmaceutically acceptable solvate or salt thereof according to claim 1, wherein Z and D represent carbon;
Y, E and A represent nitrogen;
L represents a bond or C$_2$ alkyl;
R$^1$ represents hydrogen;
R$^2$ represents hydrogen;
R$^3$ represents hydrogen or methyl;
R$^4$ represents a heteroaryl selected from indolyl, indazolyl, benzimidazolyl, or indolinonyl, said heteroaryl optionally substituted with one or two substituents selected from the group consisting of halogen, hydroxy, amino, nitro, cyano, (C$_1$-C$_4$)alkyl, (C$_2$-C$_9$)heterocyclyl, (C$_1$-C$_4$)alkyl(CO)OH, (C$_1$-C$_4$)alkyl(CO)O(C$_1$-C$_4$)alkyl, (C$_1$-C$_4$)alkyl(CO)NH$_2$, (C$_1$-C$_4$)alkyl(CO)NH(C$_1$-C$_4$)alkyl, (C$_1$-C$_4$)alkyl(CO)NH(C$_1$-C$_4$)alkyl(CO)OH, (C$_1$-C$_4$)alkyl-OH, (C$_1$-C$_4$)alkyl-O(C$_1$-C$_4$)alkyl, (C$_1$-C$_4$)alkyl-O(C$_6$-C$_{10}$)aryl, (C$_1$-C$_4$)alkyl-O(CO)(C$_1$-C$_4$)alkyl, (C$_1$-C$_4$)alkyl-O(CO)(C$_1$-C$_4$)alkyl-NH$_2$, (C$_1$-C$_4$)alkyl-O(CO)(C$_6$-C$_{10}$)aryl, (C$_1$-C$_4$)alkyl-NH$_2$, (C$_1$-C$_4$)alkyl-NH((C$_1$-C$_4$)alkyl, (C$_1$C$_4$)alkyl-N[(C$_1$C$_4$)alkyl][(C$_1$-C$_4$)-alkyl], (C$_1$-C$_4$)alkyl-NH(CO)(C$_1$-C$_4$)alkyl, (C$_1$-C$_4$)alkyl-NH(CO)(C$_1$-C$_4$)alkyl-NH$_2$, (C$_1$-C$_4$)alkyl-NH(CO)(C$_6$-C$_{10}$)aryl, (C$_1$-C$_4$)alkyl(CN), (C$_1$-C$_4$)alkyl(C$_6$-C$_{10}$)aryl, (CO)OH, (CO)O(C$_1$-C$_4$)alkyl, (CO)NH$_2$, (CO)NH(C$_1$-C$_4$)alkyl, (CO)NH(C$_1$-C$_4$)alkyl(CO)OH, (CO)(C$_1$-C$_4$)alkyl, (CO)(C$_1$-C$_4$)alkyl(C$_6$-C$_{10}$)aryl, (CO)(C$_1$-C$_4$)alkyl(C$_1$-C$_9$)heteroaryl, (CO)(C$_1$-C$_4$)alkyl(C$_2$-C$_9$)heterocyclyl, (CO)(C$_2$-C$_9$)heterocyclyl, (CO)(C$_6$-C$_{10}$)aryl, (CO)(C$_1$-C$_9$)heteroaryl, (C$_6$-C$_{10}$)aryl, (C$_6$-C$_{10}$)aryl-halogen, (C$_6$-C$_{10}$)aryl-OH, (C$_6$-C$_{10}$)aryl-NH$_2$, (C$_6$-C$_{10}$)aryl-O (C$_1$-C$_4$)alkyl, (C$_1$-C$_9$)heteroaryl, (C$_1$-C$_9$)heteroaryl-halogen, (C$_1$-C$_9$)heteroaryl-OH, (C$_1$-C$_9$)heteroaryl-NH$_2$, (C$_1$-C$_9$)heteroaryl(C$_1$-C$_4$)alkyl, (C$_1$-C$_9$)heteroaryl-O(C$_1$-C$_4$)alkyl, (C$_2$-C$_9$)heterocyclyl, (C$_2$-C$_9$)heterocyclyl(C$_1$-C$_4$)alkyl, (C$_2$-C$_9$)heterocyclyl(C$_1$-C$_4$)alkyl-OH, (C$_2$-C$_9$)heterocyclyl(C$_1$-C$_4$)alkyl-NH$_2$, O(C$_1$-C$_4$)alkyl, O(C$_1$-C$_4$)alkyl(C$_6$-C$_{10}$)aryl, O(C$_1$-C$_4$)alkyl(C$_6$-C$_{10}$)heteroaryl, O(C$_1$-C$_4$)alkyl (C$_2$-C$_9$)heterocyclyl, O(C$_1$-C$_4$)alkyl(C$_2$-C$_9$)heterocyclyl(C$_1$-C$_4$)alkyl, O(C$_1$-C$_4$)alkyl(C$_2$-C$_9$)heterocyclyl(C$_1$-C$_4$)alkyl-OH, O (EtO )$_{1-3}$H, O (EtO )$_{1-3}$(C$_1$-C$_4$)alkyl, O(C$_6$-C$_{10}$)aryl, O(CO)(C$_1$-C$_4$)alkyl, O(CO)(C$_1$-C$_4$)alkyl-NH$_2$, O(CO)(C$_6$-C$_{10}$)aryl, OCF$_3$, OSO$_2$(C$_1$-C$_4$)alkyl, OSO$_2$OH, NH(C$_1$-C$_4$)alkyl, N[(C$_1$-C$_4$)alkyl][(C$_1$-C$_4$)alkyl], NH(CO)(C$_1$-C$_4$)alkyl, NH(CO)(C$_1$-C$_4$)alkyl-NH$_2$, NH(CO)(C$_6$-C$_{10}$)aryl, NHSO$_2$(C$_1$-C$_4$)alkyl, SO$_2$NH$_2$, and CF$_3$; and R$^5$ represents hydrogen or methyl.

17. The compound or pharmaceutically acceptable solvate or salt thereof according to claim 1, wherein Y and E represent carbon;
Z, D, and A represent nitrogen;
L represents a bond or C$_2$ alkyl;
R$^2$ represents hydrogen;

$R^3$ represents hydrogen or methyl;

$R^4$ represents a heteroaryl selected from indolyl, indazolyl, benzimidazolyl, or indolinonyl, said heteroaryl optionally substituted with one or two substituents selected from the group consisting of halogen, hydroxy, amino, nitro, cyano, $(C_1-C_4)$alkyl, $(C_1-C_4)$alkyl$(C_2-C_9)$heterocyclyl, $(C_1-C_4)$alkyl(CO)OH, $(C_1-C_4)$alkyl(CO)O$(C_1-C_4)$alkyl, $(C_1-C_4)$alkyl(CO)NH$_2$, $(C_1-C_4)$alkyl(CO)NH$(C_1-C_4)$alkyl, $(C_1-C_4)$alkyl(CO)NH$(C_1-C_4)$alkyl(CO)OH, $(C_1-C_4)$alkyl-OH, $(C_1-C_4)$alkyl-O$(C_1-C_4)$alkyl, $(C_1-C_4)$alkyl-O$(C_6-C_{10})$aryl, $(C_1-C_4)$alkyl-O(CO)$(C_1-C_4)$alkyl, $(C_1C_4)$alkyl-O(CO)$(C_1-C_4)$alkyl-NH$_2$, $(C_1-C_4)$alkyl-O(CO)$(C_6-C_{10})$aryl, $(C_1-C_4)$alkyl-NH$_2$, $(C_1-C_4)$alkyl-NH$(C_1-C_4)$alkyl, $(C_1-C_4)$alkyl-N[$(C_1-C_4)$alkyl][$(C_1-C_4)$-alkyl], $((C_1-C_4)$alkyl-NH(CO)$(C_1-C_4)$alkyl, $(C_1-C_4)$alkyl-NH(CO)$(C_1-C_4)$alkyl-NH$_2$, $(C_1-C_4)$alkyl-NH(CO)$(C_6-C_{10})$aryl, $(C_1-C_4)$alkyl(CN), $(C_1-C_4)$alkyl$(C_6-C_{10})$aryl, (CO)OH, (CO)O$(C_1-C_4)$alkyl, (CO)NH$_2$, (CO)NH$(C_1-C_4)$alkyl, (CO)NH$(C_1-C_4)$alkyl(CO)OH, (CO)$(C_1-C_4)$alkyl, (CO)$(C_1-C_4)$alkyl$(C_6-C_{10})$aryl, (CO)$(C_1-C_4)$alkyl$(C_1-C_9)$heteroaryl, (CO)$(C_1-C_4)$alkyl$(C_2-C_9)$heterocyclyl, (CO)$(C_2-C_9)$heterocyclyl, (CO)$(C_6-C_{10})$aryl, (CO)$(C_1-C_9)$heteroaryl, $(C_6-C_{10})$aryl, $(C_6-C_{10})$aryl-halogen, $(C_6-C_{10})$aryl-OH, $(C_6-C_{10})$aryl-NH$_2$, $(C_6-C_{10})$aryl-O$(C_1-C_4)$alkyl, $(C_1-C_9)$heteroaryl, $(C_1-C_9)$heteroaryl-halogen, $(C_1-C_9)$heteroaryl-OH, $(C_1-C_9)$heteroaryl-NH$_2$, $(C_1-C_9)$heteroaryl$(C_1-C_4)$alkyl, $(C_1-C_9)$heteroaryl-O$(C_1-C_4)$alkyl, $(C_2-C_9)$heterocyclyl, $(C_2-C_9)$heterocyclyl$(C_1-C_4)$alkyl, $(C_2-C_9)$heterocyclyl$(C_1-C_4)$alkyl-OH, $(C_2-C_9)$heterocyclyl$(C_1-C_4)$alkyl-NH$_2$, O$(C_1-C_4)$alkyl, O$(C_1-C_4)$alkyl$(C_6-C_{10})$aryl, O$(C_1-C_4)$alkyl $(C_6-C_{10})$heteroaryl, O$(C_1-C_4)$alkyl $(C_2-C_9)$heterocyclyl, O$(C_1-C_4)$alkyl$(C_2-C_9)$heterocyclyl$(C_1-C_4)$alkyl, O$(C_1-C_4)$alkyl$(C_2-C_9)$heterocyclyl$(C_1-C_4)$alkyl-OH, O(EtO)$_{1-3}$H, O(EtO)$_{1-3}$$(C_1-C_4)$alkyl, O$(C_6-C_{10})$aryl, O(CO)$(C_1-C_4)$alkyl, O(CO)$(C_1-C_4)$alkyl-NH$_2$, O(CO)$(C_6-C_{10})$aryl, OCF$_3$, OSO$_2$$(C_1-C_4)$alkyl, OSO$_2$OH, NH$(C_1-C_4)$alkyl, N[$(C_1-C_4)$alkyl][$(C_1-C_4)$alkyl], NH(CO)$(C_1-C_4)$alkyl, NH(CO)$(C_1-C_4)$alkyl-NH$_2$, NH(CO)$(C_6-C_{10})$aryl, NHSO$_2$$(C_1-C_4)$alkyl, SO$_2$NH$_2$, and CF$_3$; and $R^5$ represents hydrogen or methyl.

18. The compound or pharmaceutically acceptable solvate or salt thereof according to claim 1, wherein Y and D represent carbon;

Z, E and A represent nitrogen;

L represents a bond or $C_2$ alkyl;

$R^I$ represents hydrogen;

$R^2$ represents hydrogen;

$R^3$ represents hydrogen or methyl;

$R^4$ represents a heteroaryl selected from indolyl, indazolyl, benzimidazolyl, or indolinonyl, said heteroaryl optionally substituted with one or two substituents selected from the group consisting of halogen, hydroxy, amino, nitro, cyano, $(C_1-C_4)$alkyl, $(C_1-C_4)$alkyl$(C_2-C_9)$heterocyclyl, $(C_1-C_4)$alkyl(CO)OH, $(C_1-C_4)$alkyl(CO)O$(C_1-C_4)$alkyl, $(C_1-C_4)$alkyl(CO)NH$_2$, $(C_1-C_4)$alkyl (CO)NH$(C_1-C_4)$alkyl, $(C_1-C_4)$alkyl(CO)NH$(C_1-C_4)$alkyl(CO)OH, $(C_1-C_4)$alkyl-OH, $(C_1-C_4)$alkyl-O$(C_1-C_4)$alkyl, $(C_1-C_4)$alkyl-O$(C_6-C_{10})$aryl, $(C_1-C_4)$alkyl-O(CO)$(C_1-C_4)$alkyl, $(C_1-C_4)$alkyl-O(CO)$(C_1-C_4)$alkyl-NH$_2$, $(C_1-C_4)$alkyl-O(CO)$(C_6-C_{10})$aryl, $(C_1-C_4)$alkyl-NH$_2$, $(C_1-C_4)$alkyl-NH$(C_1-C_4)$alkyl, $(C_1-C_4)$alkyl-N[$(C_1-C_4)$alkyl][$(C_1-C_4)$alkyl], $(C_1C_4)$alkyl-NH(CO)$(C_1-C_4)$alkyl, $(C_1-C_4)$alkyl-NH(CO)$(C_1-C_4)$alkyl-NH$_2$, $(C_1-C_4)$alkyl-NH(CO)$(C_6-C_{10})$aryl, $(C_1-C_4)$alkyl(CN), $(C_1-C_4)$alkyl$(C_6-C_{10})$aryl, (CO)OH, (CO)O$(C_1-C_4)$alkyl, (CO)NH$_2$, (CO)NH$(C_1-C_4)$alkyl, (CO)NH$(C_1-C_4)$alkyl (CO)OH, (CO)$(C_1-C_4)$alkyl, (CO)$(C_1-C_4)$alkyl $(C_6-C_{10})$aryl, (CO)$(C_1-C_4)$alkyl$(C_1-C_9)$heteroaryl, (CO)$(C_1-C_4)$alkyl$(C_2-C_9)$heterocyclyl, (CO)$(C_2-C_9)$heterocyclyl, (CO)$(C_6-C_{10})$aryl, (CO)$(C_1-C_9)$heteroaryl, $(C_6-C_{10})$aryl, $(C_6-C_{10})$aryl-halogen, $(C_6-C_{10})$aryl-OH, $(C_6-C_{10})$aryl-NH$_2$, $(C_6-C_{10})$aryl-O$(C_1-C_4)$alkyl, $(C_1-C_9)$heteroaryl, $(C_1-C_9)$heteroaryl-halogen, $(C_1-C_9)$heteroaryl-OH, $(C_1-C_9)$heteroaryl-NH$_2$, $(C_1-C_9)$heteroaryl$(C_1-C_4)$alkyl, $(C_1-C_9)$heteroaryl-O$(C_1-C_4)$alkyl, $(C_2-C_9)$heterocyclyl, $(C_2-C_9)$heterocyclyl$(C_1-C_4)$alkyl, $(C_2-C_9)$heterocyclyl$(C_1-C_4)$alkyl-OH, $(C_2-C_9)$heterocyclyl$(C_1-C_4)$alkyl-NH$_2$, O$(C_1-C_4)$alkyl, O$(C_1-C_4)$alkyl$(C_6-C_{10})$aryl, O$(C_1-C_4)$alkyl$(C_6-C_{10})$heteroaryl, O$(C_1-C_4)$alkyl$(C_2-C_9)$heterocyclyl, O$(C_1-C_4)$alkyl$(C_2-C_9)$heterocyclyl$(C_1-C_4)$alkyl, O$(C_1-C_4)$alkyl$(C_2-C_9)$heterocyclyl$(C_1-C_4)$alkyl-OH, O(EtO)$_{1-3}$H, O(EtO)$_{1-3}$$(C_1-C_4)$alkyl, O$(C_6-C_{10})$aryl, O(CO)$(C_1-C_4)$alkyl, O(CO)$(C_1-C_4)$alkyl-NH$_2$, O(CO)$(C_6-C_{10})$aryl, OCF$_3$, OSO$_2$$(C_1-C_4)$alkyl, OSO$_2$OH, NH$(C_1-C_4)$alkyl, N[$(C_1-C_4)$alkyl][$(C_1-C_4)$alkyl], NH(CO)$(C_1-C_4)$alkyl, NH(CO)$(C_1-C_4)$alkyl-NH$_2$, NH(CO)$(C_6-C_{10})$aryl, NHSO$_2$$(C_1-C_4)$alkyl, SO$_2$NH$_2$, and CF$_3$; and $R^5$ represents hydrogen or methyl.

19. The compound or pharmaceutically acceptable solvate or salt thereof according to claim 1, wherein Z represents carbon or nitrogen;

Y represents carbon or nitrogen, wherein one of Z and Y represents nitrogen;

A, D and E is selected from carbon or nitrogen, wherein A and D represent nitrogen and E represents carbon; or A and E represent nitrogen and D represents carbon; or E represents nitrogen and A and D represent carbon;

$R^1$ represents hydrogen or methyl, when D represents carbon, and $R^1$ is absent when D represents nitrogen;

$R^2$ represents hydrogen or amino;

$R^3$ represents hydrogen, methyl, trifluoromethyl or $(C_0-C_1)$alkylaryl;

$R^5$ represents hydrogen or methyl;

L-$R^4$ is selected from the group consisting of:

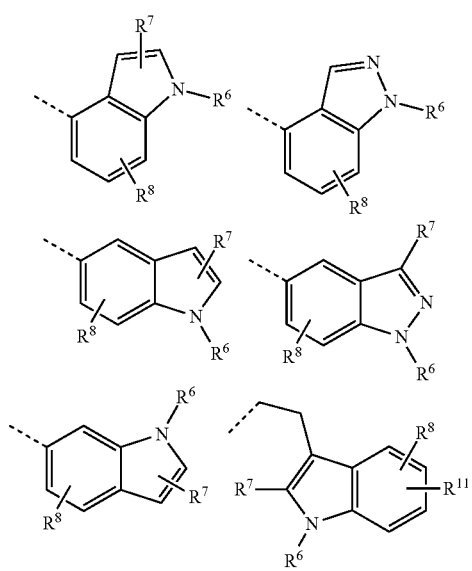

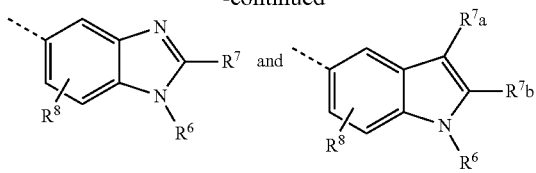

R⁶ is selected from hydrogen or methyl;
R⁷ is selected from hydrogen, methyl, ($C_1$-$C_4$)alkyl-OH, or (CO)OCH₃,
R⁷a and R⁷b are independently selected from hydrogen or methyl;
R⁸ is selected from halogen, hydrogen, hydroxy, (CO)OH, (CO)OCH₃, O($C_1$-$C_4$)alkyl, O($C_1$-$C_4$)alkyl($C_6$-$C_{10}$)aryl, O($C_1$-$C_4$)alkyl($C_2$-$C_9$)heterocyclyl, O(EtO)$_{1-3}$ ($C_1$-$C_4$)alkyl, or OCF₃; and
$R^H$ is selected from hydrogen, methyl, or O($C_1$-$C_4$)alkyl.

20. The compound or pharmaceutically acceptable solvate or salt thereof according to claim 1, wherein when A is nitrogen, L represents a bond or ($C_2$)alkyl.

21. The compound or pharmaceutically acceptable solvate or salt thereof according to claim 1, said compound being selected from the group consisting of:

$N^4$(1H-indol -5-ylmethyl)-$N^2$41H-indol-4-yppyrimidine-2,4-diamine;
$N^4$-(1H-indol -5-ylmethyl)-$N^2$-(1H-indol-4-yppyrimidine-2,4-diamine;
$N^4$-(1H-indol-5-ylmethyl)-$N^2$(methyl-1H-indol -5-yl)pyrimidine-2,4-diamine;
$N^4$-(1H-indol -5-ylmethyl)-$N^2$(1H-indazol-5yl-)pyrimidine-2,4-diamine;
$N^2$-[2(1H-indol -3yl)ethyl]-$N^4$(1H-indol-5-ylmethyl)pyrimidine-2,4-diamine;
3-{2[4-(1H-indol -5-ylmethylamino)-pyrimidin-2ylamino]ethyl}-1H-indol -5-ol;
$N^4$-(1H-indol -5-ylmethyl)-$N^2$[2(5-methyl-1H-indol -3yl)ethyl]pyrimidine-2,4-diamine;
$N^4$-(1H-indol -5-ylmethyl)-$N^2$[2(5-methoxy-1H-indol-3yl)ethyl]pyrimidine-2,4-diamine;
$N^2$-(1H-indol-4-yl)-$N^4$(2-methyl-1H-indol-5ylmethyl)pyrimidine-2,4-diamine;
$N^2$(1H-indol-3-yl)-ethyl)-$N^4$(2-methyl-1H-indol -5ylmethyl)pyrimidine-2,4-diamine;
$N^2$(1H-indol-4-yl)-$N^4$-(1H-indazol-5ylmethyl)pyrimidine-2,4-diamine;
$N^4$-(1H-benzo[d]imidazol-5-ylmethl)-$N^2$(1H-indol-4-yl)pyrimidine-2,4-diamine;
$N^4$(1H-indol -6-ylmethyl)-$N^2$(1H-indol-4-yl)pyrimidine-2,4-diamine;
$N^2$(1H-indol -5-ylmethyl)-$N^4$-(1H-indol-4-yl)pyrimidine-2,4-diamine;
$N^2$-(1H-indol -5-ylmethyl)-$N^4$(2methyl-1H-indol -5-yl)pyrimidine-2,4-diamine;
$N^4$[2-(1H-indol -3yl)ethyl]-$N^2$(1H-indol-5-ylmethyl)pyrimidine-2,4-diamine;
3-{2-[2-(1H-indol -5-ylmethylamino)-pyrimidin-4-ylamino]ethyl}-1H-indol -5-ol;
$N^2$(1H-indol -5-ylmethyl)-$N^4$-[2(5-methyl-1H-indol -3yl)ethyl]pyrimidine-2,4-diamine;
$N^2$(1H-indol -5-ylmethyl)-$N^4$-[2(5-methoxy-1H-indol-3-yl)ethyl]pyrimidine-2,4-diamine;
$N^2$-(1H-indazol-5 -ylmethyl)-$N^4$-(1H-indol-4-yl)pyrimidine-2,4-diamine;
$N^2$-(1H-indol -4-yl)-$N^4$-(1H-indol -5ylmethyl)-6-methylpyrimidine-2,4-diamine;
3-{2[4(1H-indol -5-ylmethylamino)-6-methyl-pyrimidin-2-ylamino]ethyl}-1H-indol -5-ol;
$N^4$-(1H-indol -5 -ylmethyl)-$N^2$-(2-methyl-1H-indol -5-yl)-6-trifluoromethylpyrimidine-2,4-diamine;
$N^2$-(2-(1H-indol -3yl)ethyl)-$N^4$-(1H-indol-5-ylmethyl)-6-trifluoromethylpyrimidine-2,4-diamine;
$N^4$-(1H-indazol-5-ylmethyl)-$N^2$-(1H-indol-4-yl)-6-methylpyrimidine-2,4-diamine;
$N^4$-(1H-indol -5-ylmethyl)-$N^2$-(1H-indol -4-yl)pyrimidine-2,4,5-triamine;
$N^4$-(1H-indol-5-ylmethyl)-$N^2$-(1H-indol-5-yl)pyrimidine-2,4,5-triamine;
$N^4$-(1H-indol -5-ylmethyl)-$N^2$-(1H-indol-6-yl)pyrimidine-2,4,5-triamine;
$N^4$-(2-methyl-1H-indol -5-yl)-$N^2$-(2-methyl-1H-indol -5-ylmethyl)pyrimidine-2,4-diamine;
$N^2$-[2-(5-methoxy- 1H-indol -3-ypethyl]-$N^4$-(2-methyl-1H-indol -5-ylmethyl)pyrimidine-2,4-diamine;
$N^2$-(1H-indazol-5-ylmethyl)-$N^4$-(2-methyl- 1H-indol -5-yl)pyrimidine-2,4-diamine;
$N^4$-(1H-indazol-5-ylmethyl)-$N^2$-[2-(5-methoxy-1H-indol-3-yl)ethyl]pyrimidine-2,4-diamine;
$N^2$-(1H-benzo[d]imidazol-5-ylmethyl)-$N^4$-(2-methyl-1H-indol -5-yl)pyrimidine-2,4-diamine;
$N^4$-(1H-benzo[d]imidazol-5-ylmethyl)-$N^2$-[2-(5-methoxy-1H-indol -3-Yl)ethyl]pyrimidine-2,4-diamine;
$N^2$-(1H-indol -6-ylmethyl)-$N^4$-(2-methyl-1H-indol -5-yl)pyrimidine-2,4-diamine;
$N^4$-(1H-indol -6-ylmethyl)-$N^2$-[2-(5-methoxy-1H-indol -3-yl)ethyl]pyrimidine-2,4-diamine;
$N^4$-(1H-indol -5-ylmethyl)-$N^2$-{2-[5-(benzyloxy)-1H-indol -3-yl]ethyl}pyrimidine-2,4-diamine;
$N^4$-(1H-indol -5-ylmethyl)-$N^2$-{2-[5-(2-morpholinoethoxy)-1H-indol -3-yl]ethyl}pyrimidine-2,4-diamine;
$N^4$-(1H-indol -5-ylmethyl)-$N^2$-{2-[5-(2-methoxyethoxy)-1H-indol -3-yl]ethyl}pyrimidine-2,4-diamine;
$N^4$-(1H-indol -5-ylmethyl)-$N^2$-(1-methyl-1H-indol -4-yl)pyrimidine-2,4-diamine;
$N^4$-(1H-indol -5-ylmethyl)-$N^2$-(1H-indazol-4-yl)pyrimidine-2,4-diamine;
Methyl 4-[4-(1H-indol -5-ylmethylamino)pyrimidin-2-ylamino]-1H-indole-6-carboxylate;
$N^2$-(1H-indol -5-ylmethyl)-$N^4$-(1H-indol-5-yl)pyrimidine-2,4-diamine;
$N^2$-(1H-indol -5-ylmethyl)-6-methyl-$N^4$-(2-methyl-1H-indol -5-yl)pyrimidine-2,4-diamine;
$N^4$-(1H-indol-5-ylmethyl)-$N^2$-[2-(5-methoxy-1H-indol-3yl)ethyl]-6-methylpyrimidine-2,4-diamine;
$N^4$-(1H-indol -5-ylmethyl)-6-benzyl-$N^2$-[2-(5-methoxy-1H-indol-3-yl)ethyl]pyrimidine-2,4-diamine;
$N^4$-(1H-indol -5-ylmethyl)-$N^2$-[2-(5-methoxy-7-methyl-1H-indol -3yl)ethyl]pyrimidine-2,4-diamine;
$N^4$-(1H-indol -5-ylmethyl)-$N^2$-[2-(5-ethoxy-1H-indol-3-yl)ethyl]pyrimidine-2,4-diamine;
$N^4$-(1H-indol -5-ylmethyl)-$N^2$-{[2-(trifluoromethoxy)-1H-indol -3yl]ethyl}pyrimidine-2,4-diamine;
$N^4$-(1H-indol -5-ylmethyl)-$N^2$[2-(5-fluoro-1H-indol-3-yl)ethyl]pyrimidine-2,4-diamine;
$N^4$-(1H-indol -5-ylmethyl)-$N^2$-[2-(6-methoxy-1H-indol-3-yl)ethyl]pyrimidine-2,4-diamine;
$N^4$-(1H-indol -5-ylmethyl)-$N^2$-[2-(7-methoxy-1H-indol-3-yl)ethyl]pyrimidine-2,4-diamine;
$N^2$-(1H-indol -5-ylmethyl)-$N^4$-(1,2-dimethyl-1H-indol -5-yl)pyrimidine-2,4-diamine;
methyl 5-[2-(1H-indol -5-ylmethylamino)pyrimidin-4-ylamino]-1H-indole-2-carboxylate;

$N^2$-(1H-indol-5-ylmethyl)-$N^4$-(2,3-dimethyl-1H-indol-5-yl)pyrimidine-2,4-diamine;

$N^2$-(1H-indol-5-ylmethyl)-$N^4$-(1H-benzo[d]imidazol-5yl)pyrimidine-2,4-diamine;

$N^2$-(1H-indol-5-ylmethyl)-$N^4$-(2-methyl-1H-benzo[d]imidazol-5-yl)pyrimidine-2,4-diamine;

$N^4$-(1H-indol-5-ylmethyl)-$N^2$-(1H-indazol-4-yl)-6-methylpyrimidine-2,4-diamine;

$N^2$-[2-(5-methoxy-1H-indol-3yl)ethyl]-6-methyl-$N^4$-[(2-methyl-1H-indol-5-yl)methyl]pyrimidine-2,4-diamine;

$N^4$-(1H-indazol-5-ylmethyl)-$N^2$-[2-(5-methoxy-1 H-indol-3yl)ethyl]-6-methylpyrimidine-2,4-diamine;

$N^4$-(1H-indol-5-ylmethyl)-$N^2$-[2-(5-methoxy-2-methyl-1H-indol-3yl)ethyl]-6-methylpyrimidine-2,4-diamine;

$N^4$-(1H-indol-5-ylmethyl)-$N^2$-[2-(4-methoxy-1H-indol-3yl)ethyl]pyrimidine-2,4-diamine;

4-[4-(1H-indol-5-ylmethylamino)pyrimidin-2-ylamino]-1 H-indole-6-carboxylic acid;

$N^2$-(1H-indol-4-yl)-6-methyl-$N^4$-[(2-methyl-1H-indol-5-yl)methyl]pyrimidine-2,4-diamine;

{5-[2-(1H-indol-5-ylmethylamino)pyrimidin-4-ylamino]-1H-indol-2-yl}methanol;

$N^2$-(1H-indol-5-ylmethyl)-$N^4$-methyl-$N^4$-(2-methyl-1H-indol-5-yl)pyrimidine-2,4-diamine;

$N^2$-(1H-indol-5-ylmethyl)-$N^4$-(1,2-dimethyl-1H-indol-5-yl)-$N^4$-methylpyrimidine-2,4-diamine;

$N^4$-(1H-indol-5-ylmethyl)-$N^2$-[2-(5-methoxy-1-methyl-1H-indol-3-yl)ethyl]pyrimidine-2,4-diamine;

$N^4$-(1H-indol-5-ylmethyl)-$N^2$-[2-(5-methoxy-1-methyl-1 H-indol-3-yl)ethyl]-$N^2$-methylpyrimidine-2,4-diamine; and $N^4$-(1H-indol-5-ylmethyl)-$N^2$-[2-(5-methoxy-1H-indol-3yl)ethyl]-$N^2$-methylpyrimidine-2,4-diamine.

22. A pharmaceutical composition comprising the compound or pharmaceutically acceptable solvate or salt thereof according to claim 1 together with a pharmaceutically acceptable diluent or carrier.

23. A method for treatment of colon cancer or breast cancer, which comprises administering to a subject in need thereof, a therapeutically effective amount of the compound or pharmaceutically acceptable solvate or salt thereof according to claim 1.

* * * * *